United States Patent
Gray et al.

(10) Patent No.: US 12,030,892 B2
(45) Date of Patent: Jul. 9, 2024

(54) CRBN MODULATORS

(71) Applicant: DANA-FARBER CANCER INSTITUTE, INC., Boston, MA (US)

(72) Inventors: Nathanael Gray, Boston, MA (US); Tinghu Zhang, Brookline, MA (US); Eric Fischer, Chestnut Hill, MA (US); Alyssa Verano, Allston, MA (US); Zhixiang He, Brookline, MA (US); Guangyan Du, Jamaica Plain, MA (US); Katherine Donovan, Boston, MA (US); Radoslaw Nowak, Boston, MA (US); Jing Ting Christine Yuan, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 792 days.

(21) Appl. No.: 17/255,750

(22) PCT Filed: Jun. 27, 2019

(86) PCT No.: PCT/US2019/039553
§ 371 (c)(1),
(2) Date: Dec. 23, 2020

(87) PCT Pub. No.: WO2020/006262
PCT Pub. Date: Jan. 2, 2020

(65) Prior Publication Data
US 2021/0277018 A1    Sep. 9, 2021

Related U.S. Application Data

(60) Provisional application No. 62/692,189, filed on Jun. 29, 2018.

(51) Int. Cl.
*C07D 495/14* (2006.01)
*A61K 47/54* (2017.01)
*C07D 401/04* (2006.01)

(52) U.S. Cl.
CPC .......... *C07D 495/14* (2013.01); *A61K 47/545* (2017.08); *C07D 401/04* (2013.01)

(58) Field of Classification Search
CPC C07D 401/14; C07D 495/14; A61K 31/4545; A61K 47/545
See application file for complete search history.

(56) References Cited

U.S. PATENT DOCUMENTS

| | | |
|---|---|---|
| 2014/0309436 A1 | 10/2014 | Greig et al. |
| 2016/0058872 A1 | 3/2016 | Crew et al. |
| 2016/0235730 A1 | 8/2016 | Bradner et al. |

FOREIGN PATENT DOCUMENTS

| | | |
|---|---|---|
| CN | 107382862 A | 11/2017 |
| WO | 2017/007612 A1 | 1/2017 |
| WO | 2017197051 A1 | 11/2017 |
| WO | 2019043214 A1 | 3/2019 |
| WO | 2019140387 A1 | 7/2019 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Acute Leukemia, Merck Manual (Online Edition) 6 pages, pp. 1-6 (2013).*
Burslem, G., et al. "Efficient Synthesis of Immunomodulatory Drug Analogues Enables Exploration of Structure-Degradation Relationships", ChemMedChem, 2018, 13:1508-1512.
El-Zanfally, S. et al. "Derivatives of Glutarimide Likely to Possess Therapeutic Activity", Journal of Pharmaceutical Sciences, 1965, 54(3):467-469.
Abruzzese et al., "Inhibition of bromodomain and extra-terminal (BET) proteins increases NKG2D ligand MICA expression and sensitivity to NK cell-mediated cytotoxicity in multiple myeloma cells: role of cMYC-IRF4-miR-125b interplay", J. Hematol. Oncol., 2016, vol. 9, No. 134, 19 pages.
Chaidos et al., "Inhibition of bromodomain and extra-terminal proteins (BET) as a potential therapeutic approach in haematological malignancies: emerging preclinical and clinical evidence", Ther. Avd. Hematol., 2015, vol. 6, No. 3, pp. 128-141.
Donati et al., "BRD4 and Cancer: going beyond transcriptional regulation", Mol. Cancer, 2018, vol. 17, No. 164, 13 pages.
Roe et al., "BET Bromodomain Inhibition Suppresses the Function and Hematopoietic Transcription Factors in Acute Myeloid Leukemia", Mol. Cell, vol. 58, pp. 1028-1039, (2015).
CAS RN 1333622-73-3—Created on PubChem Dec. 3, 2011 (PubChem CID 53592257).
CAS RN 1489856-35-0—Created on PubChem Oct. 24, 2012 (PubChem CID 65955101).

* cited by examiner

*Primary Examiner* — Deepak R Rao
(74) *Attorney, Agent, or Firm* — BURNS & LEVINSON, LLP; Daniel W. Clarke; Shawn P. Foley

(57) ABSTRACT

Disclosed are degraders, pharmaceutical compositions containing them, and methods of making and using the degraders to treat diseases and disorders characterized by dysregulated or dysfunctional protein activity that can be targeted by cereblon.

19 Claims, 9 Drawing Sheets

CRBN MODULATORS

RELATED APPLICATIONS

This application is a national stage application, filed under 35 U.S.C. § 371, of International Application No. PCT/US2019/039553, filed Jun. 27, 2019, which claims the benefit of priority under 35 U.S.C. § 119(e) to U.S. Provisional Application No. 62/692,189, filed on Jun. 29, 2018, each of which is incorporated herein by reference in its entirety.

GOVERNMENT LICENSE RIGHTS

This invention was made with government support under grant number R01CA214608 awarded by the National Institutes of Health. The government has certain rights in the invention.

BACKGROUND OF THE INVENTION

The gene that encodes cereblon (CRBN) was first identified in the course of a study of genes related to memory and learning; the gene was assigned the name CRBN based on its supposed role in the development of cerebral tissues and because its expression in the hippocampus among other areas, is associated with memory and learning processes. Higgins, et al., Neurol. 63(10):1927-31 (2004).

Cereblon is a 442-amino acid multifunctional protein located in the cytoplasm, nucleus and peripheral membrane of the human brain and other tissues (Wada et al., Biochem. & Biophys. Res. Comm. 477:388-94 (2016)). It interacts with the DNA damage-binding protein-1 (DDB1), Cullin 4 (Cul4A and Cul4B), and regulator of Cullins 1 (RoC1) to form the functional E3 ubiquitin ligase complex, which is known as the $CRL4^{CRBN}$ E3 ubiquitin ligase complex. Cereblon's role as part of this complex includes targeting proteins for proteolysis (degradation) via a ubiquitin-proteasome pathway. See, e.g., Chang et al., Int. J. Biochem. Mol. Biol. 2(3):287-94 (2011).

Cereblon is closely associated with the metabolism and proliferation of normal cells as well as tumor cells. On one hand, its existence ensures normal metabolic function and normal physiological function of ion channels, which are important to maintaining cell growth and proliferation. On the other hand, cereblon is also involved in the occurrence of many diseases, such as cancer. See, generally, Shi et al., J. Immunol. Res. Article ID 9130608 (2017).

Immunomodulatory drugs ("IMiDs"). are a new class of anti-cancer drugs that are derived from thalidomide, a drug which has been approved by the FDA for treatment of multiple myeloma. In addition to thalidomide itself, two thalidomide analogs, lenalidomide and pomalidomide, have been approved by the FDA (and are being marketed under the names REVLIMID® and POMALYST®, respectively) for treatment of multiple myeloma (among other diseases). As suggested by their nomenclature, one of the first known properties of IMiDs was their immunomodulatory capacity, including cytokine modulation and T cell co-stimulation (Schafer et al., J. Pharmacol. & Exper. Ther. 305:1222-32 (2003)), resulting in interleukin-2 production in T cells. Subsequently, IMiDs were shown to have pleiotropic effects on a wide range of immune cells including natural killer (NK) cell activation and B cell and monocyte inhibition (Corral et al., J. Immunol. 163:380-6 (1999)).

Cereblon has been identified as a common primary target for IMiDs. For example, it has been reported that members of the Ikaros family of transcription factors, Ikaros and Aiolos (encoded by the genes Ikaros family zinc finger protein 1 (IKZF1) and IKZF3 respectively) are recruited as protein substrates for $CRL4^{CRBN}$ in T cells in response to treatment with lenalidomide and pomalidomide, resulting in enhanced production of IL-2 and other cytokines that regulate T cell function. See, Gandhi et al., Br. J. Hematol. 164:811-21 (2014). It has also been reported that lenalidomide, but not pomalidomide, induces the degradation of the protein kinase, casein kinase 1α (CK1α), which exploits CK1α haploinsufficiency associated with 5q-deletion associated myelodysplastic syndrome. See, Krönke et al., Nature 523:183-8 (2015). Structural studies have shown that these IMiDs bind in a shallow hydrophobic pocket on the surface of cereblon, and that the binding is mediated by the glutarimide ring that is common to thalidomide, lenalidomide and pomalidomide.

More recently, CRBN-binding compounds named "cereblon modulators" have been developed. For example, CC-122, a new chemical entity termed 'pleiotropic pathway modifier', binds cereblon and promotes degradation of Aiolos and Ikaros in diffuse large B-cell lymphoma (DLBCL) and T cells in vitro, in vivo, and in patients, resulting in both cell autonomous as well as immunostimulatory effects. See, Hagner et al., Blood 126(6):779-89 (2016). CC-885, another new cereblon modulator, has been reported to possess anti-tumor activity which is broader than that of thalidomide, lenalidomide and pomalidomide. CC-885 is mediated by cereblon-dependent ubiquitination and degradation of the translation termination factor glutathione S-transferase pi gene 1 (GSTP1). See, Matyskiela et al., Nature 535:2'2-7 (2016).

The exploitation of cereblon as a mediator in disease treatment has also led to the development of hetero-bifunctional PROTACs (PROteolysis TArgeting Chimera) that recruit targeted proteins that are themselves disease mediators (e.g., bromodomain-containing protein 4 (BRD4)) to $CRL4^{CRBN}$ E3 ubiquitin ligase, leading to degradation of the targeted protein. See, e.g., Lu et al, Cell Cancer Bio. 22(6):755~63 (2015).

SUMMARY OF THE INVENTION

A first aspect of the present invention is directed to a bifunctional (or bispecific) compound (also referred to herein as a "degrader" or "PROTAC"), which has a structure represented by formula (I):

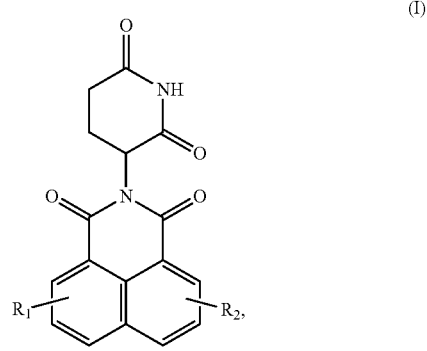

wherein $R_1$ and $R_2$ independently represent H, halo, hydroxyl, optionally substituted C1-C5 alkyl, optionally substituted C1-C5 alkoxy, optionally substituted amine, optionally substituted amide, acyl, or

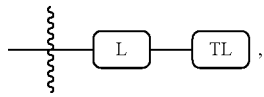

provided that one of $R_1$ and $R_2$ represent

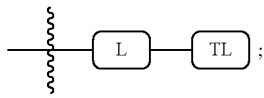

L represents a linker; and TL (targeting ligand) represents a moiety that binds a target protein; or a pharmaceutically acceptable salt or stereoisomer thereof.

In some embodiments, $R_1$ represents

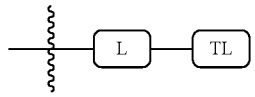

and $R_2$ represents H, halo, hydroxyl, optionally substituted C1-C5 alkyl, optionally substituted C1-C5 alkoxy, optionally substituted amine, optionally substituted amide, or acyl.

In some embodiments, $R_2$ represents

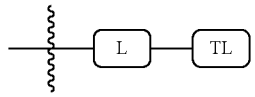

and $R_1$ represents H, halo, hydroxyl, optionally substituted C1-C5 alkyl, optionally substituted C1-C5 alkoxy, optionally substituted amine, optionally substituted amide, or acyl.

In some embodiments, $R_1$ and $R_2$ independently represent optionally substituted C1-C5 alkoxy, provided that one of $R_1$ and $R_2$ represents

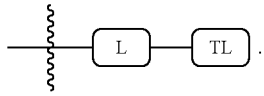

In some embodiments, the targeting ligand binds bromodomain and extra-terminal (BET) family proteins (e.g., BRD2, BRD3, BRD4, and bromodomain testis-specific protein (BRDT)

Another aspect of the present invention is directed to a pharmaceutical composition including a therapeutically effective amount of a bifunctional compound of formula (I), or a pharmaceutically acceptable salt or stereoisomer thereof, and a pharmaceutically acceptable carrier. Bifunctional compounds of the present invention may be water-soluble; hence, they may be advantageously and conveniently formulated for parenteral or oral administration, whereupon they permeate membranes of cells harboring proteins to which the bifunctional compounds bind (via the targeting ligand) and degrade them.

Yet another aspect of the present invention is directed to methods of making the bifunctional compounds.

Further aspects of the present invention are directed to methods of treating diseases or disorders characterized or mediated by aberrant activity of a protein, that entails administration of a therapeutically effective amount of a bifunctional compound of formula (I) or a pharmaceutically acceptable salt or stereoisomer thereof to a subject in need thereof.

In some embodiments, the disease or disorder is cancer.

In some embodiments, the cancer is selected from the group consisting of NUT midline carcinoma, treatment-refractory acute myeloid leukemia, myelodysplastic syndrome, multiple myeloma, a triple-negative breast cancer, an estrogen receptor-positive breast cancer, small cell lung cancer, non-small cell lung cancer, castration resistant prostate cancer, pancreatic ductal adenocarcinoma, colorectal cancer, neuroblastoma and an MYCN-driven solid tumor.

Without intending to be bound by any particular theory of operation, the bifunctional compounds of formula (I) are believed to cause degradation of dysfunctional proteins that are involved in the genesis and progression of disease via the cell's Ubiquitin/Proteasome System, whose function is to routinely identify and remove damaged proteins. The degron functionality recruits the $CRL4^{CRBN}$ E3 ubiquitin ligase to tag the target protein (which is bound by the targeting ligand functionality) for ubiquitination and degradation through the proteasome, which is a large complex that degrades the ubiquitinated protein into small peptide fragments. After destruction of the target protein, the degrader is released and continues to be active. Thus, by engaging and exploiting the body's own natural protein disposal system, the bifunctional compounds of the present invention may represent a potential improvement over traditional small molecule inhibitors of dysfunctional proteins in the treatment cancers and other disease that have proven difficult to treat.

BRIEF DESCRIPTION OF THE DRAWINGS

FIG. 1A shows the degradation of target protein IKZF1 (measured in relative abundance) as a function of concentration (expressed in Log (compound (CPD)) M) by compound 9. FIG. 1B shows the degradation of target protein IKZF1 (measured in relative abundance) as a function of concentration (expressed in Log (CPD) M) by compound 10. FIG. 1C shows the degradation of target protein IKZF1 (measured in relative abundance) as a function of concentration (expressed in Log (CPD) M) by compound 11. FIG. 1D shows the degradation of target protein IKZF1 (measured in relative abundance) as a function of concentration (expressed in Log (CPD) M) by lenalidomide.

FIG. 2A shows the degradation of subunits BD1 and BD2 of BRD2, BRD3, and BRD4 (expressed in units of relative abundance) as function of concentration (expressed in units of log [compound (Cmpd)][M]) of inventive bifunctional compound 2 (FIG. 2A). FIG. 2B shows the degradation of subunits BD1 and BD2 of BRD2, BRD3, and BRD4 (expressed in units of relative abundance) as function of concentration (expressed in units of log[Cmpd] [M]) of inventive bifunctional compounds 1 (FIG. 2A). FIG. 2C shows the degradation of subunits BD1 and BD2 of BRD2, BRD3, and BRD4 (expressed in units of relative abundance) as function of concentration (expressed in units of log[Cmpd] [M]) of known control dBET6.

FIG. 3A shows CRBN binding in an FP displacement assay (measured in mP) as a function of concentration (expressed in Log (CPD) M) by compound 9. FIG. 3B shows CRBN binding in an FP displacement assay (measured in mP) as a function of concentration (expressed in Log (CPD) M) by compound 10. FIG. 3C shows CRBN binding in an FP displacement assay (measured in mP) as a function of concentration (expressed in Log (CPD) M) by compound 11. FIG. 3D shows CRBN binding in an FP displacement assay (measured in mP) as a function of concentration (expressed in Log (CPD) M) by lenalidomide.

FIG. 4A shows the change in relative protein abundance with treatment of inventive bifunctional compound 1 (1 µM, 6 hrs), compared to DMSO control. FIG. 4B shows the change in relative protein abundance with treatment of inventive bifunctional compound 2 (1p M, 6 hrs), compared to DMSO control. Significant changes were assessed by moderated t-test and displayed with log 2 fold change on the y-axis and negative log 10 P values on the x-axis for one independent biological replicate of compound 1 or compound 2 and three independent biological replicates of DMSO.

DETAILED DESCRIPTION OF THE INVENTION

Figure 1A:
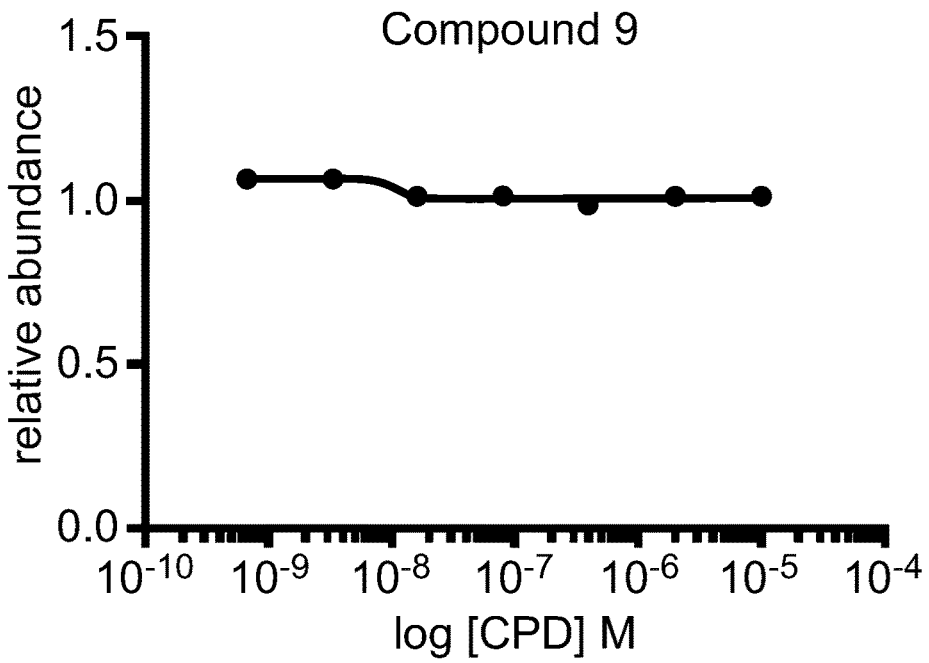
FIG. 1A-FIG. 1D are graphs that show degradation of target protein IKZF1 by thalidomide analogs 9, 10 and 11 and FDA-approved lenalidomide.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group.

In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

As used herein, the term "aldehyde" is represented by the formula —C(O)H. The terms "C(O)" and C=O are used interchangeably herein.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carboxylic acid" is represented by the formula —C(O)OH, and a "carboxylate" is represented by the formula —C(O)O—.

As used herein, the term "ester" is represented by the formula —OC(O)$Z^1$ or —C(O)O$Z^1$, where $Z^1$ may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ketone" is represented by the formula $Z^1C(O)Z^2$, where $A^1$ and $A^2$ independently represent alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonyl" refers to the sulfo-oxo group represented by the formula —S(O)$_2Z^1$, where $Z^1$ may be hydrogen, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonylamino" (or "sulfonamide") is represented by the formula —S(O)$_2$NH$_2$.

As used herein, the term "thiol" is represented by the formula —SH.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$.

Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., 0, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain.

The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R_c$ is an alkylene chain such as methylene or ethylene.

In some embodiments, the aralkyl group is an optionally substituted benzyl group. The term aryl also embraces aralkoxy groups which as used herein refer to a group bonded through an oxygen atom of the formula —O—$R_c$-aryl where $R_c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —R$^c$-heteroaryl, where R$^c$ is an alkylene chain as defined above. The term heteroaryl also embraces heteroaralkoxy (or heteroarylalkoxy) groups which as used herein refer to a group bonded through an oxygen atom of the formula —O—R$^c$-heteroaryl, where R$^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl, alkoxy, substituted alkoxy, alkenyl, substituted alkenyl, alkynyl, substituted alkynyl, cyclic, substituted cyclic, carbocyclic, substituted carbocyclic, heterocyclic, substituted heterocyclic, aryl (e.g., benzyl and phenyl), substituted aryl (e.g., substituted benzyl or phenyl), heteroaryl, substituted heteroaryl, aralkyl, substituted aralkyl, halo, hydroxyl, aryloxy, substituted aryloxy, alkylthio, substituted alkylthio, arylthio, substituted arylthio, cyano, carbonyl, substituted carbonyl, carboxyl, substituted carboxyl, amino, substituted amino, amido, substituted amido, sulfonyl, substituted sulfonyl, amino acid, and peptide groups.

The term "binding" as it relates to interaction between the targeting ligand and the targeted protein, typically refers to an inter-molecular interaction that is substantially specific in that binding of the targeting ligand with other proteinaceous entities present in the cell is functionally insignificant. In some embodiments, such as in the case of bromodomain-containing proteins, binding of the targeting ligand to the protein target may be selective with respect to BRD proteins. By way of example, JQ1, which as disclosed herein as a targeting ligand, selectively binds one or more members of the bromodomain and extra-terminal (BET) family (BRD2, BRD3, BRD4, and bromodomain testis-specific protein (BRDT)).

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, bifunctional (or bispecific) compounds of the present invention have a structure represented by formula (I):

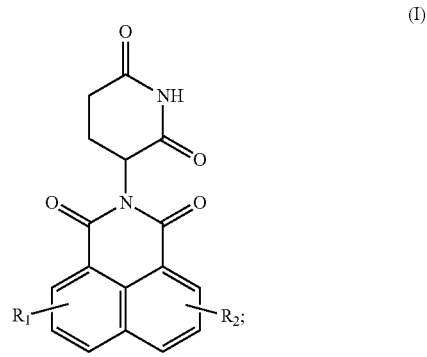

wherein $R_1$ and $R_2$ independently represent H, halo, hydroxyl, optionally substituted C1-C5 alkyl, optionally substituted C1-C5 alkoxy, optionally substituted amine, optionally substituted amide, acyl or

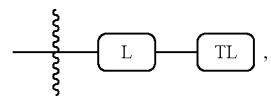

provided that one of $R_1$ and $R_2$ represents;

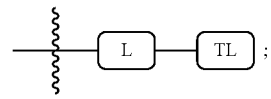

L represents a linker;
and TL (targeting ligand) represents a moiety that binds a target protein;
or a pharmaceutically acceptable salt or stereoisomer thereof.

In some embodiments, $R_1$ represents

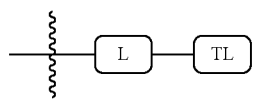

and $R_2$ represents H, halo, hydroxyl, optionally substituted C1-C5 alkyl, optionally substituted C1-C5 alkoxy, optionally substituted amine, optionally substituted amide, or acyl.

In some embodiments, $R_2$ represents

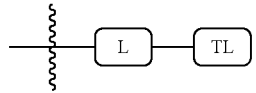

and $R_1$ represents H, halo hydroxyl, optionally substituted C1-C5 alkyl, optionally substituted C1-C5 alkoxy, optionally substituted amine, optionally substituted amide, or acyl.

In some embodiments, $R_1$ and $R_2$ independently represent optionally substituted C1-C5 alkoxy, provided that one of $R_1$ and $R_2$ represents

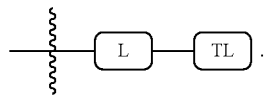

Targeting Ligands

Broadly, the bifunctional compounds of the present invention may be constructed to target any aberrant (e.g., dysregulated or dysfunctional) protein. Thus, the targeting ligand may bind target proteins, including for example, the expression products of Ikaros family zinc finger protein 1 (IKZF1) and IKZF3, and the following proteins: casein kinase 1 alpha (CK1α), family with sequence similarity 83 member F (FAM83F), DTW domain containing 1 (DTWD1), zinc finger protein 91 homolog (ZFP91), ZFP62, ZFP36 ring finger protein like (ZFP36L2), ring finger protein 166 (RNF166), Ikaros family zinc finger protein 2 (2), IKZF4, IKZF5, Ras-related protein Rab-28 (RAB28), glutathione S-transferase pi 1 (GSTP1), GSPT2, mitochondrial import inner membrane translocase subunit Tim10 (TIMM10), GDNF inducible zinc finger protein 1 (GZF1), early growth response 1 (EGR1), hypermethylated in cancer 1 (HIC1), HIC2, insulinoma-associated protein 2 (INSM2), odd-skipped related transcription factor 2 (OSR2), protein polybromo-1 (PB1), PR domain zinc finger protein 15 (PRD15), spalt-like transcription factor 1 (SALL1), SALL3, SALL4, WIZ, zinc finger and BTB domain-containing protein 17 (ZBT17), ZBT41, ZBT49, ZBT7A, ZBT7B, ZBTB2, ZBTB39, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483, SNF517, ZNF526, ZNF581, ZNF587, ZNF589, ZNF618, ZNF644, ZNF646, ZNF653, ZNF654, ZNF692, ZNF724, ZNF771, ZNF782, ZNF784, ZNF814, zinc finger and SCAN domain containing 10 (ZSC10), ZSC22, ZC827, and zinc finger with UFM1-specific peptidase domain (ZUFSP).

In some embodiments, the bifunctional compounds of the present invention directly target Interleukin 1 Receptor Associated Kinase 1 (IRAK 1) and/or IRAK 4, KRAS, HRAS and NRAS (particularly G12C mutants), and bromodomain-containing proteins, e.g., extra terminal (BET) protein family which includes BRD2, BRD3, BRD4, and BRDT, as further disclosed hereinbelow. Yet other aberrant proteins that may be targeted by the bifunctional compounds of the present invention include B7.1 and B7, TINFR1m, TNFR2, NADPH oxidase, BclIBax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, trypanosomal GAPDH, glycogen phosphorylase, Carbonic anhydrase, chemokine receptors, JAW STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-αR, ICAM1, Cat+ channels, VCAM, VLA-4 integrin, selectins, CD40/CD40L, neurokinins and receptors, inosine monophosphate dehydrogenase, p38 MAP Kinase, Ras-Raf-MEK-ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5-α reductase inhibitors, angiotensin 11, glycine receptor, noradrenaline reuptake receptor, endothelin receptors, neuropeptide Y and receptor, adenosine receptors, adenosine kinase and AMP deaminase, purinergic receptors (P2Y1, P2Y2, P2Y4, P2Y6, P2X1-7), farnesyltransferases, geranylgeranyl transferase, TrkA receptor for NGF, 0-amyloid, tyrosine kinase Flk-IIKDR, vitronectin receptor, integrin receptor, Her-21 neu, telomerase inhibition, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium release channel, chloride channels, acetyl-CoA carboxylase, adenylosuccinate synthetase, protoporphyrinogen oxidase and enolpyruvylshikimate-phosphate synthase. Targeting ligands that bind these proteins, e.g., small molecule inhibitors of the proteins, are known in the art.

In some embodiments, the compounds of formula (I) include a targeting ligand that binds Interleukin-1 receptor kinase 1 (IRAK1), interleukin-1 receptor kinase 4 (IRAK4) or both IRAK1 and IRAK4 (IRAK1/4). These kinase enzymes are immune modulators that are involved in the etiology of a variety and multitude of diseases and disorders, both cancerous and non-cancerous alike. Interleukin-1 receptor-associated kinases are a family of intracellular serine-threonine kinases, which consists of IRAK1, IRAK2, IRAK3 (also known as IRAKM), and IRAK4. See, Li et al., Proc. Nat'l. Acad. Sci. USA 99:5567-5572 (2002). IRAK4 signals downstream of the pathogen sensing toll-like receptors (TLRs), except for TLR3, and the innate/adaptive immune signaling IL-1 family (the IL-1, IL-18, and IL-33 receptors). See, Chaudhary et al., J. Med. Chem. 58:96-110 (2015). Upon binding to the IL-1 receptors or the TLRs, these receptors recruit the adaptor protein myeloid differentiation primary response gene 88 (MyD88) through the conserved Toll-IL-R (TIR) domain. MyD88 then utilizes the death domain (DD) homotypic interaction to recruit IRAK4. See, Lin, et al., Nature 465:885-890 (2010). IRAK4 activation leads to the recruitment and phosphorylation of IRAK1 or IRAK2, which then leads to MAP kinase/IKK activation and pro-inflammatory cytokine production. Activation of TLR downstream targets like cytokines TNF and IL-1 can result in a systemic disorder like sepsis or local, autoimmune and chronic inflammation disease like rheumatoid arthritis or inflammatory bowel syndrome. IRAK4 activation has also been implicated in cancer. For example, activating MyD88 mutations such as L265P in activated diffuse large B-cell lymphoma (DLBCL) and Waldenstrom's macroglobulinemia (WM) have established a role for IRAK family signaling in these and other cancers. See, Rhyasen et al., Brit. J Cancer 112:232-37 (2015). They are collectively referred to herein as "IRAK-mediated diseases and disorders."

In some embodiments, the compound of formula (I) includes a targeting ligand that binds G12C mutants of KRas, HRas and NRas (hereinafter collectively referred to as "KRas"). Ras proteins contain a so-called G domain which contains the enzymatically active domain of the protein, namely guanine nucleotide binding and hydrolysis. The C-terminal extension, known as the CAAX box, targets Ras to the cell membrane. The G domain contains a phosphate-binding loop, known as the P-loop, which represents a pocket where guanine nucleotides are bound. It has been determined that several conserved amino acid residues in the pocket of the P-loop, namely Glycine 12, Threonine 26 and Lysine 16, are essential for guanine nucleotide binding and hydrolysis. The G domain of Ras also contains the Switch I and II regions, also known as the spring-loaded mechanism, due to their ability to switch Ras between the active and inactive state.

Mutations in any one of HRas, KRas, and NRas are quite common in tumorigenesis. The majority of the mutations are found in the KRas gene. For instance, about 30% of all human tumors which have been found to carry a Ras mutation, and KRas mutations have been detected in about 25-30% of tumors. The most common KRas mutations are found at G12, G13 which are in the P-loop and at residue Q61, which is in the Switch II region. The G12C (glycine-12 to cysteine) mutation of KRas gene occurs frequently (about 13%) in cancer. It is even more prevalent (43%) in lung cancer, and has been found in almost 100% of MYH-associated polyposis (familial colon cancer syndrome). For purposes of comparison, mutations in the NRas and the HRas genes have been found to occur at a much lower frequency, i.e., about 8% and 3%, respectively.

In some embodiments, the compound of formula (I) includes a targeting ligand that targets KRASG12C for degradation, as follows:

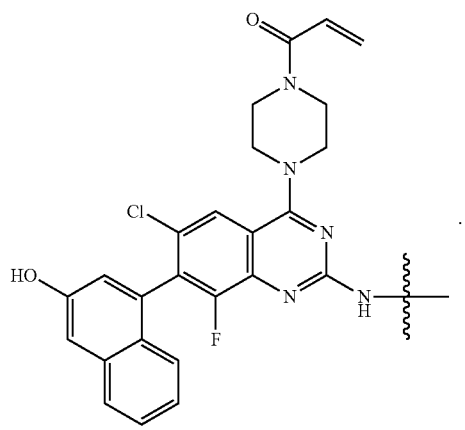

(TL1)

Other compounds that may be useful as KRASG12C-targeting ligands are known in the art. See, e.g., U.S. Patent Application Publication 2018/0015087 (e.g., formulae II and III, including IIIA-E); WO 2013/155223; WO 2016/168540; WO 2017/058728; WO 2017/058768; WO 2017/058805; WO 2017/058792; WO 2017/058807; WO 2017/058902; WO 2017/058915 and U.S. Pub. Nos. 2014/0288045; 2015/0239900; 2016/0031898; 2016/0108019; 2016/0297774; 20160159738; 20170247376; 2017/0022184 and 2017/0197945.

In some embodiments, the compound of formula (I) includes a targeting ligand that binds a bromodomain protein for degradation. Bromodomains, which are approximately 110 amino acids long, are found in a large number of chromatin-associated proteins including histones. They have been identified in approximately 70 human proteins. Interactions between bromodomains and modified histones may be an important mechanism underlying chromatin structural changes and gene regulation. Bromodomain-containing proteins have been implicated in the etiology and progression of diseases including cancer, inflammation and viral replication.

In some embodiments, the compounds of formula (I) of the present invention target a bromodomain-containing protein contained in the Switch/Sucrose Non-Fermentable (SWI/SNF) chromatin-remodeling complex. This complex is a nucleosome remodeling complex that includes a group of proteins that associate to remodel the way in which DNA is packaged inside the cell. The SWI/SNF chromatin-remodeling complex has been reported to be involved in gene regulation, cell linage specification and development and comprises a number of bromodomain containing subunits, including BRG1 (also known as SMARCA4), BRM (also known as SMARCA2) and PBRM1 (also known as PB1).

Representative examples of entities that may be suitable for use as PB1-targeting ligands in the compounds of the present invention are disclosed in U.S. Patent Application Publication 2018/0086720 A1, e.g., Paragraphs 71-83 therein.

In some embodiments, the compounds of formula (I) include a targeting ligand that binds proteins that are members of the bromodomain and extra-terminal (BET) family (e.g., BRD2, BRD3, BRD4, and bromodomain testis-specific protein (BRDT)). Inventive compounds containing JQ1 (or a deuterated form of same) as the targeting ligand will target BRD4, BRD3, and BRD2 for degradation. Thus, in some embodiments, the targeting ligands of the present invention may be based on the following structure:

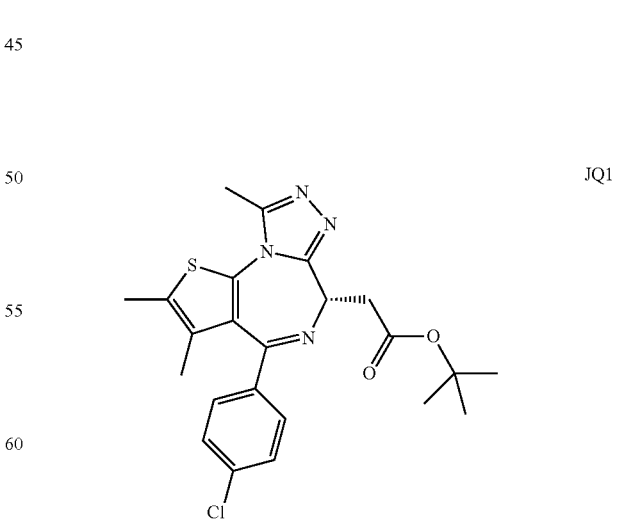

JQ1

Representative examples of targeting ligands based on JQ1 that target BRD4 may thus have the following structures:

(TL2-1)
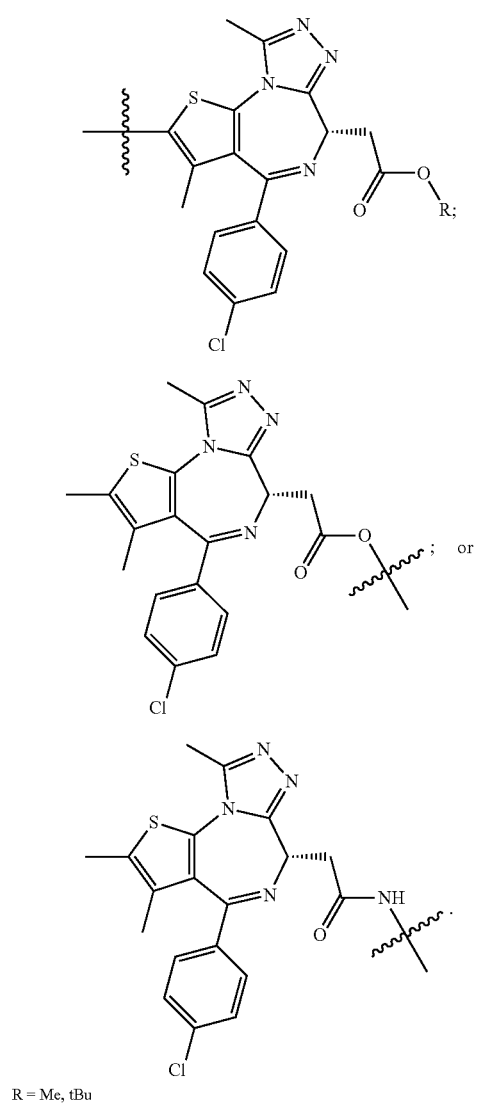
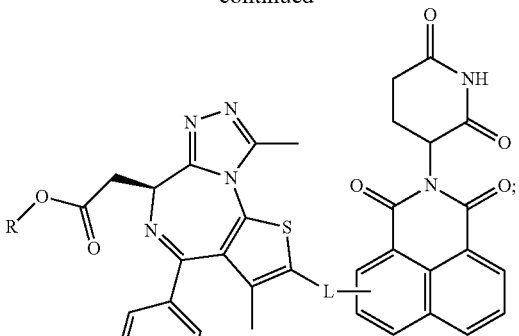
R = Me, tBu
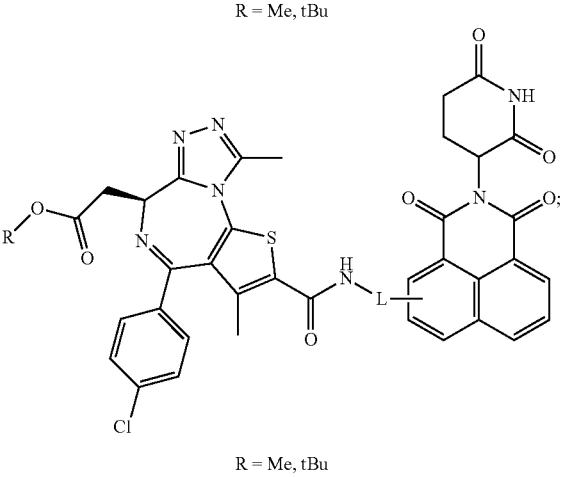
R = Me, tBu
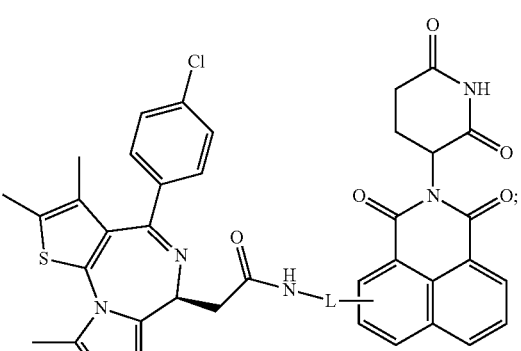
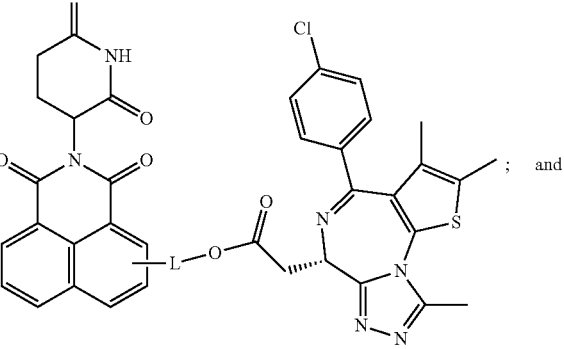
In some embodiments, the compounds of the present invention are represented by the following structures:
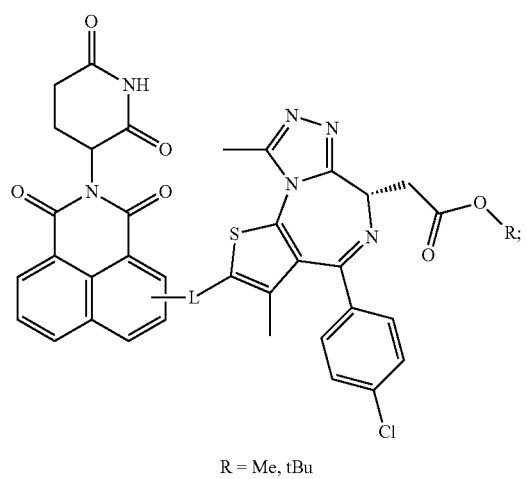
R = Me, tBu -continued

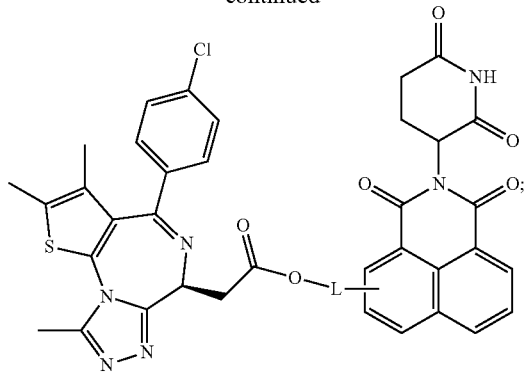

or a pharmaceutically acceptable salt or stereoisomer thereof.

Linkers

The linker ("L") provides a covalent attachment the targeting ligand and the moiety that binds cereblon. The structure of linker may not be critical, provided it does not substantially interfere with the activity of the targeting ligand or the degron. In some embodiments, the linker may be an alkylene chain or a bivalent alkylene chain, either of which may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker may be a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In certain embodiments, the linker is an alkylene chain having 1-10 alkylene units and interrupted by or terminating in

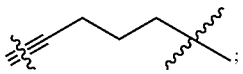

In other embodiments, the linker is a polyethylene glycol linker having 2-8 PEG units and terminating in

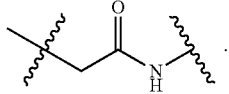 [SMILES: *CC(=O)N*]

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chain:

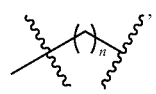

(L1)

wherein n is an integer of 1-10, inclusive, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10 examples of which include:

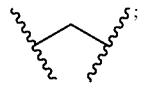

(L1-a)

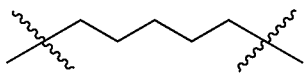

(L1-b)

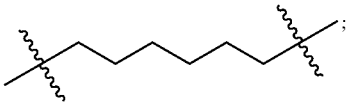

(L1-c)

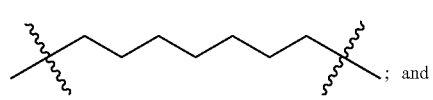

(L1-d)

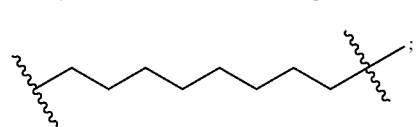

; and (L1-e)

alkylene chains terminating in various functional groups (as described above), examples of which are as follows:

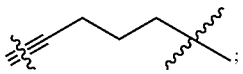

(L2-a)

-continued

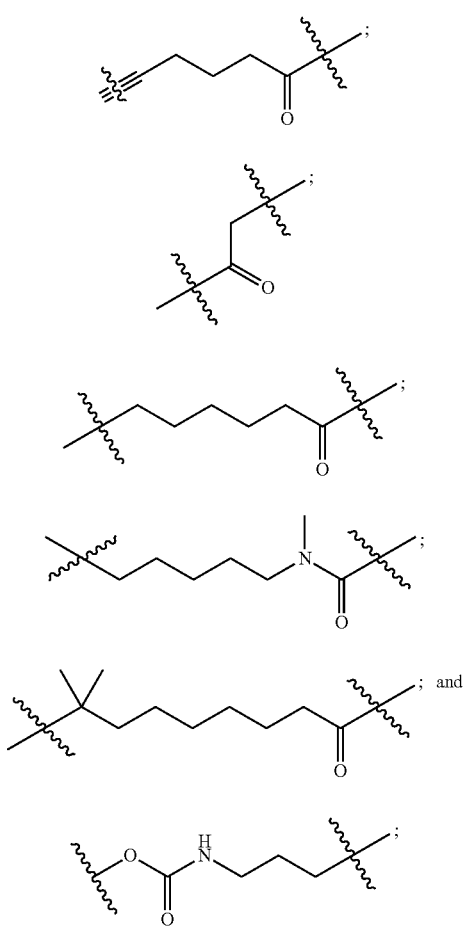

alkylene chains interrupted with various functional groups (as described above), examples of which are as follows:

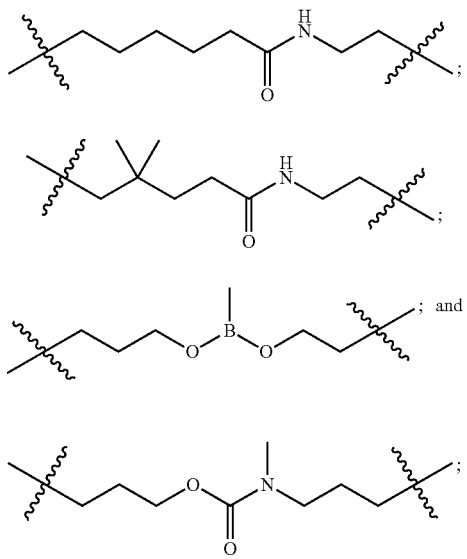

alkylene chains interrupted or terminating with heterocyclene groups, e.g.,

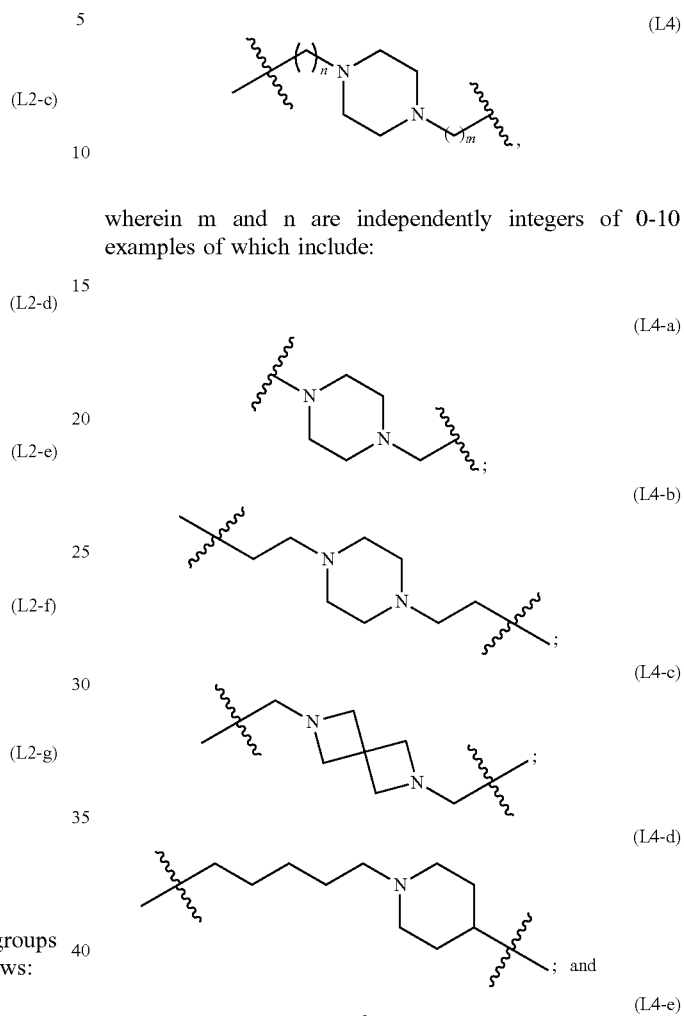

wherein m and n are independently integers of 0-10 examples of which include:

alkylene chains interrupted by amide, heterocyclene and/or aryl groups, examples of which include:

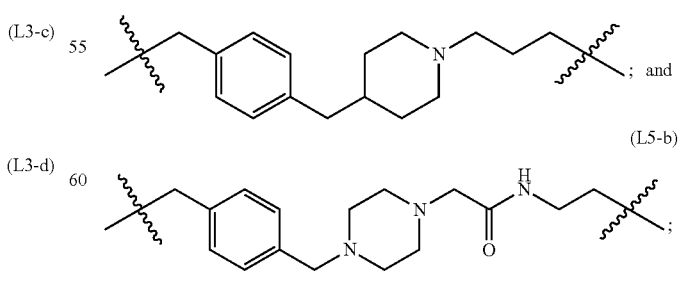

alkylene chains interrupted by heterocyclene and aryl groups, and a heteroatom, examples of which include:

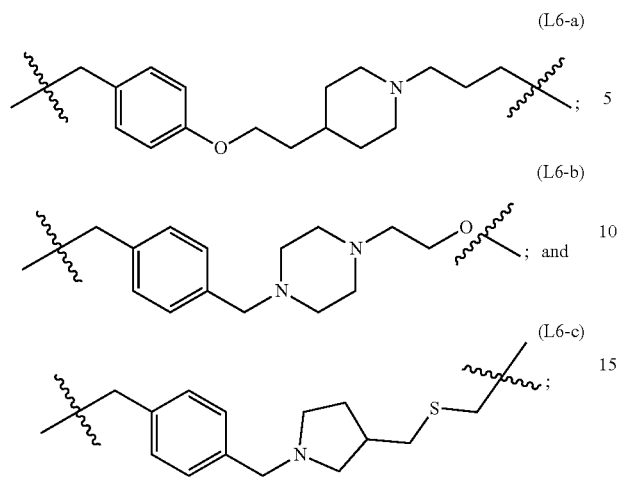

(L6-a)

(L6-b)

(L6-c)

and
alkylene chains interrupted by a heteroatom such as N, O or B, e.g.,

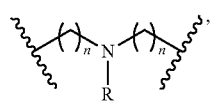

(L7)

wherein n is an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H, or $C_1$ to $C_4$ alkyl, an example of which is

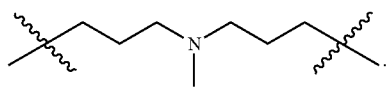

(L7-a)

In some embodiments, the linker is a polyethylene glycol chain, examples of which include:

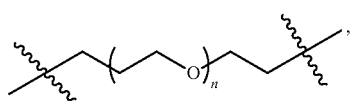

(L8)

wherein n is an integer of 2-10, examples of which include:

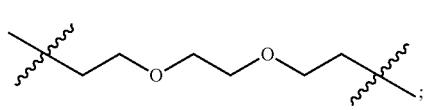

(L8-a)

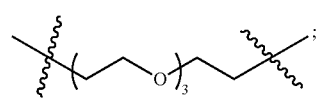

(L8-b)

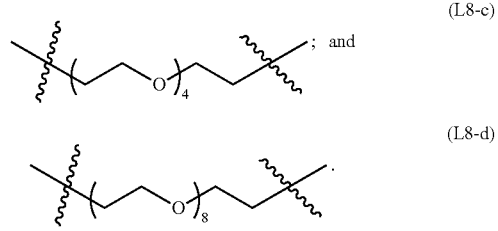

(L8-c)

(L8-d)

In some embodiments, the polyethylene glycol linker may terminate in a functional group, examples of which are as follows:

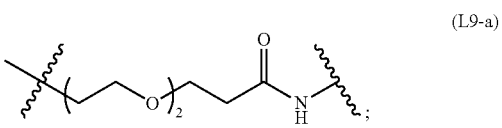

(L9-a)

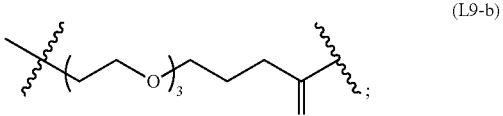

(L9-b)

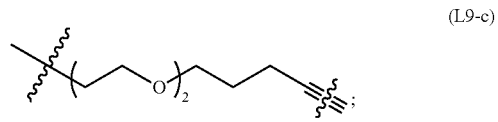

(L9-c)

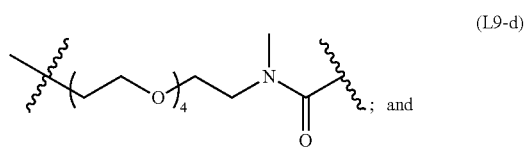

(L9-d)

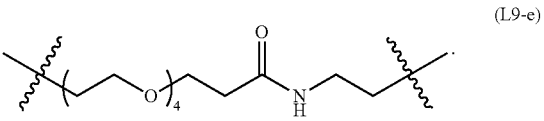

(L9-e)

In some embodiments, the linker has a structure represented by one of the following structures:

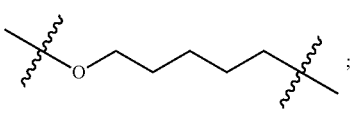

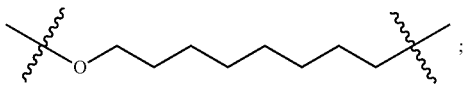

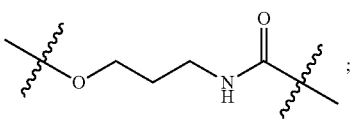

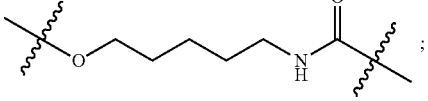

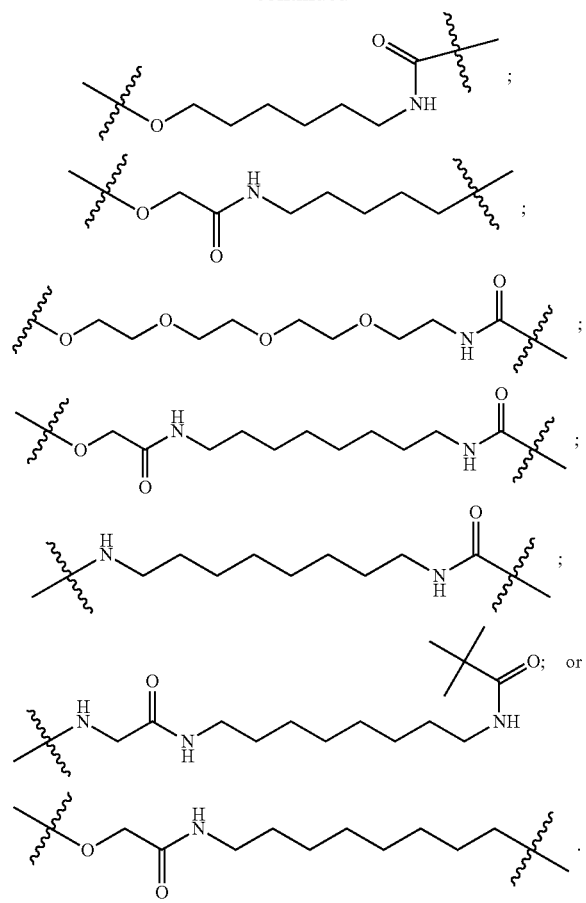
In some embodiments, the compounds of the present invention are represented by the following structures:
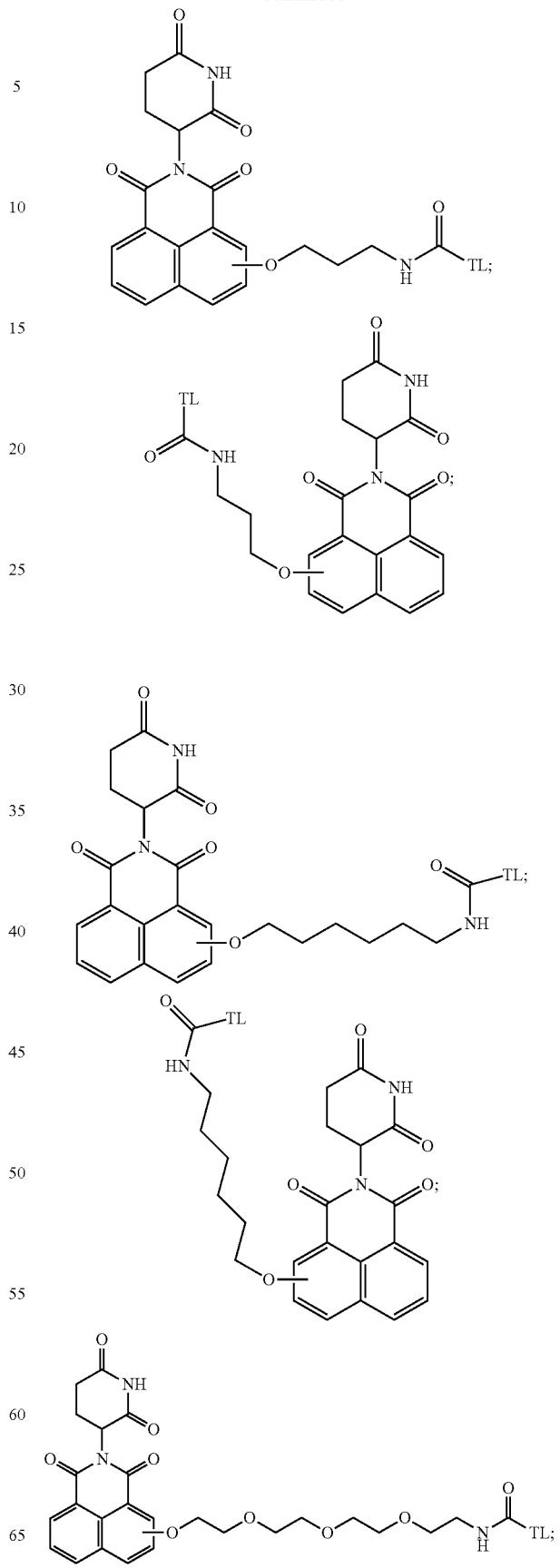

27
-continued
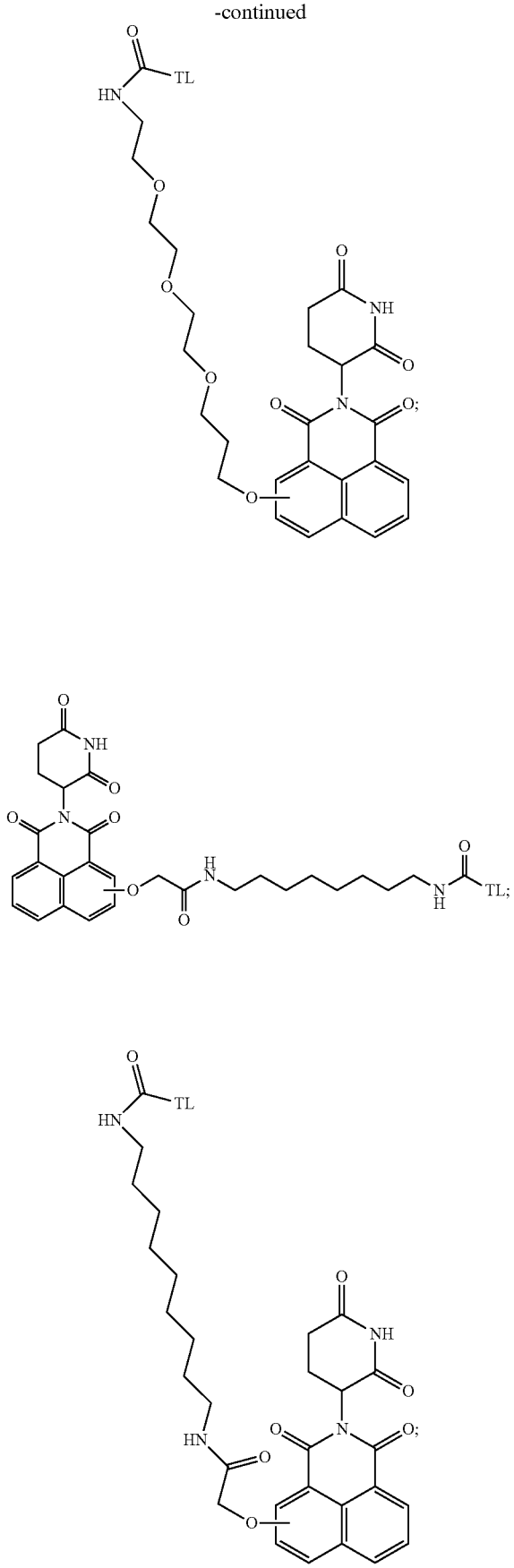
28
-continued
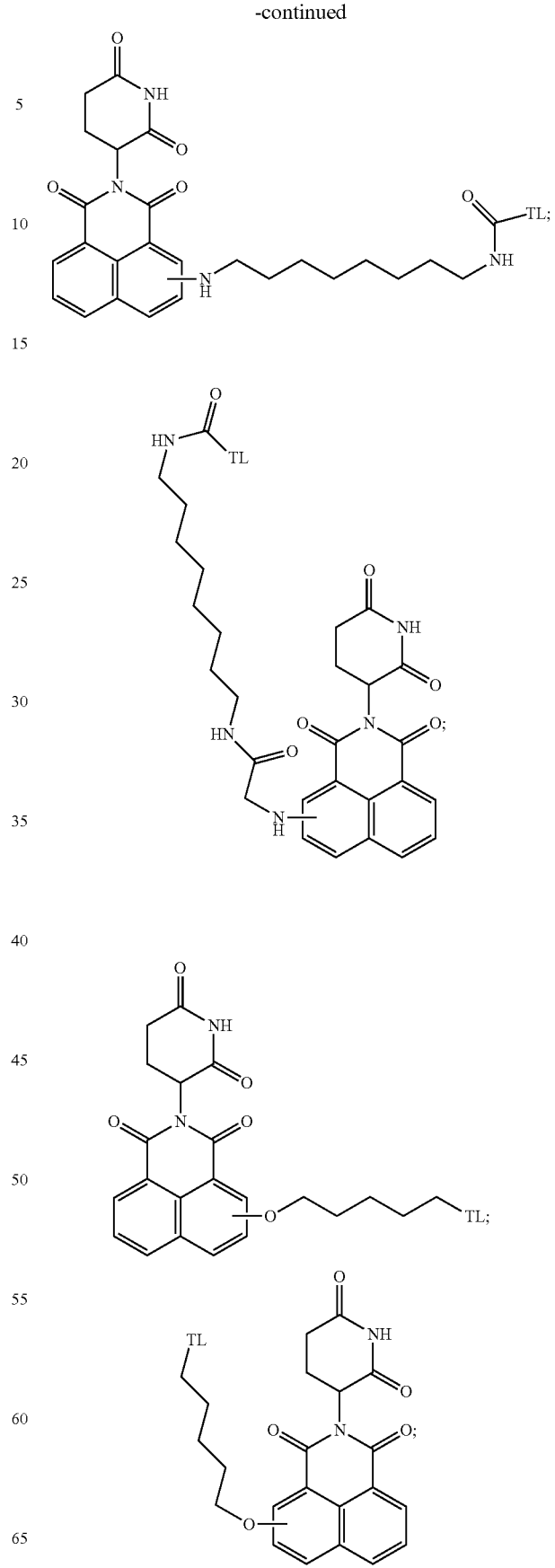

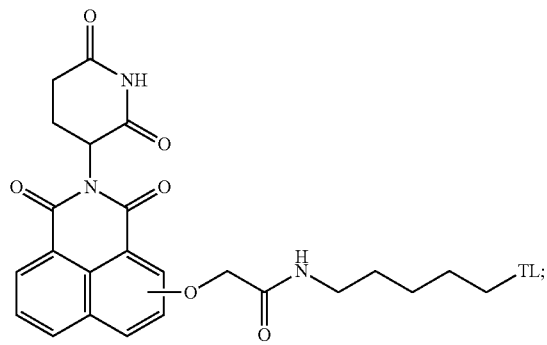
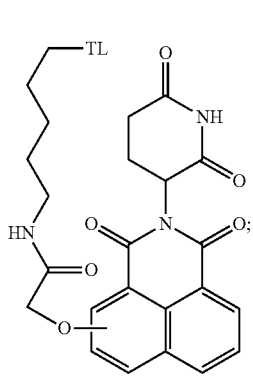
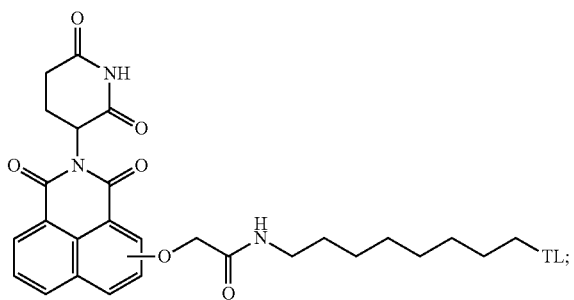
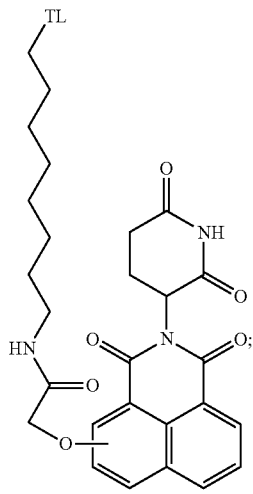
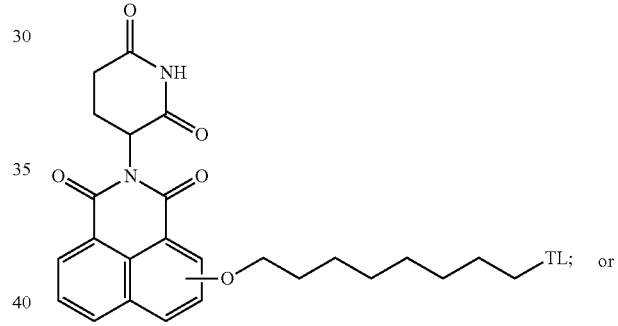
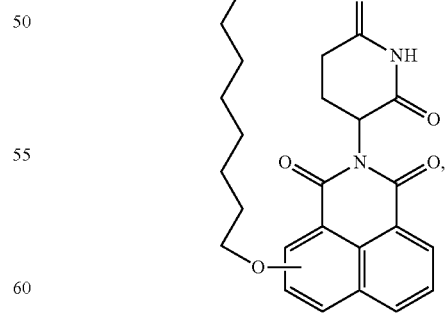
or a pharmaceutically acceptable salt or stereoisomer thereof.
In some embodiments, the compounds of the present invention are represented by the following structures:

(1)
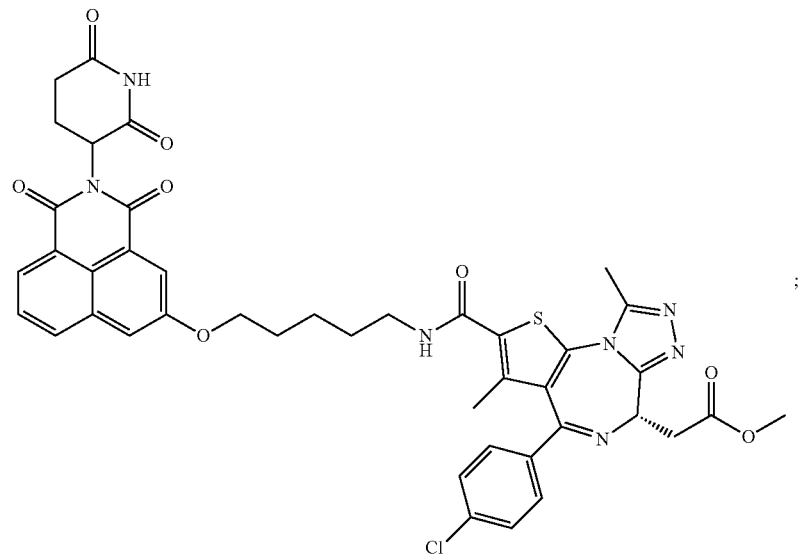
(2)
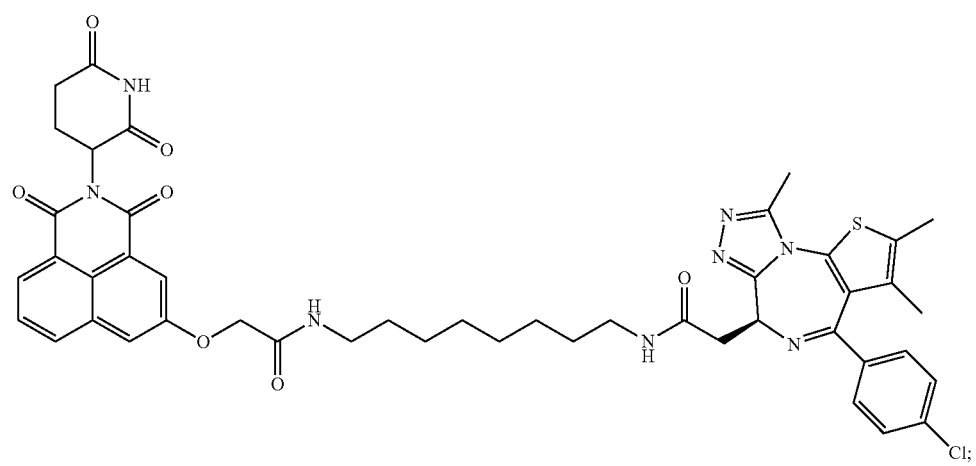
(3)
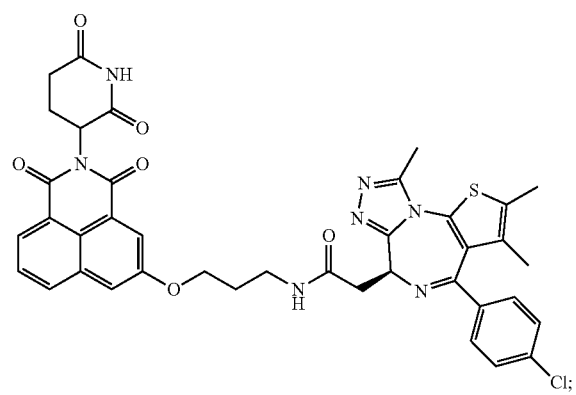
(4)

(5)
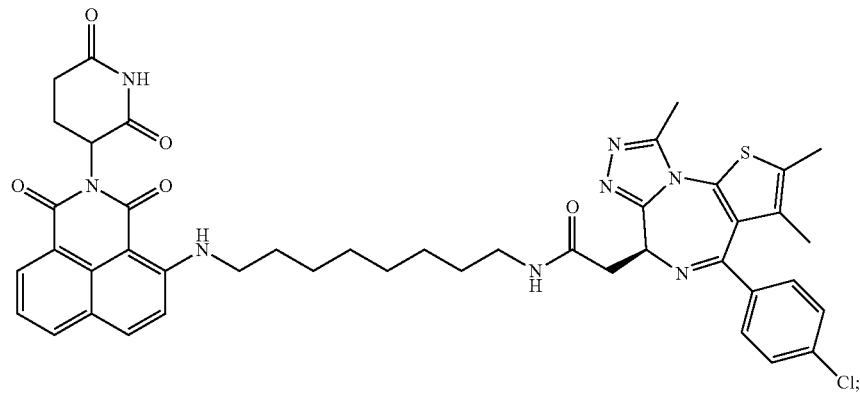
(6)
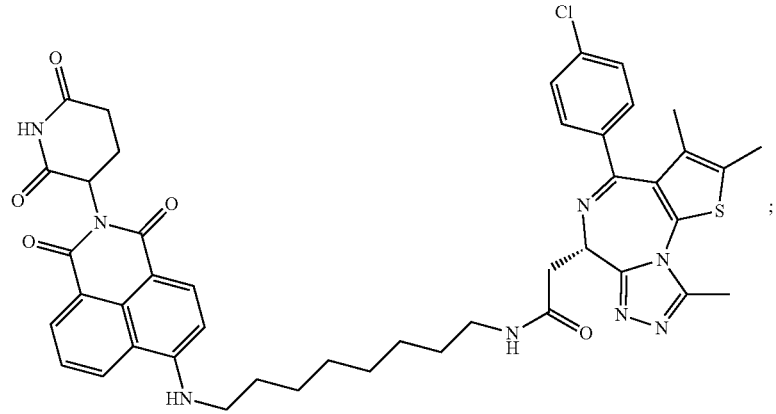
(7)
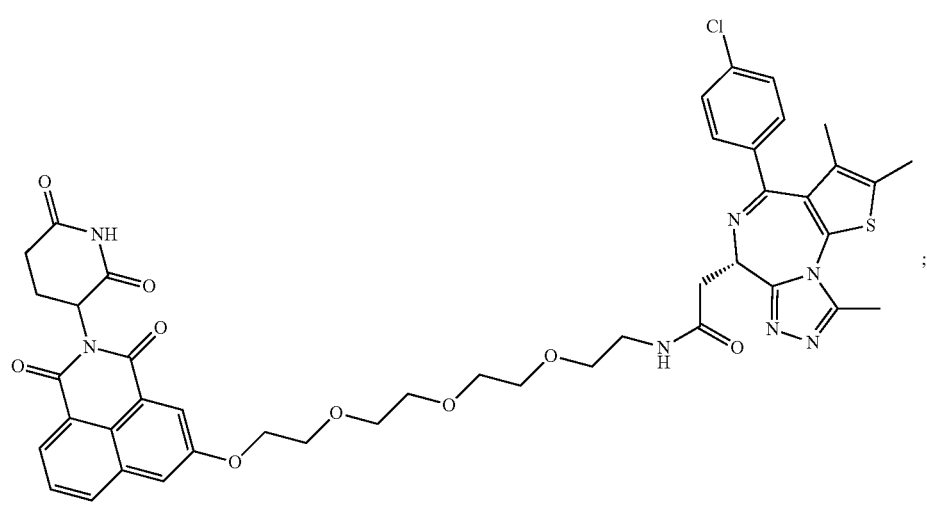

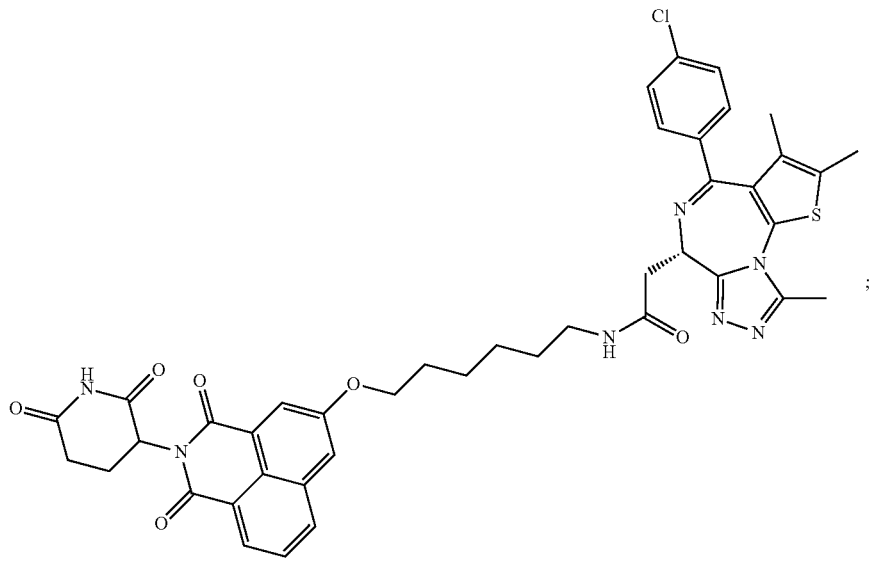

(8)

or a pharmaceutically acceptable salt or stereoisomer thereof.

Bifunctional compounds of the present invention may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the bifunctional compound of formula (I) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances. For example, in bifunctional compounds of formula (I) that target BRD4, a JQ1 moiety may be deuterated in order to increase half-life.

Bifunctional compounds of formula (I) may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In addition, bifunctional compounds of formula (I) embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In another aspect, the present invention is directed to a method for making a bifunctional compound of formula I, or a pharmaceutically acceptable salt or stereoisomer thereof. Broadly, the inventive compounds may be prepared by any process known to be applicable to the preparation of chemically related compounds. The bifunctional compounds of the present invention will be better understood in connection with the synthetic schemes that are described in various working examples and which illustrate non-limiting methods by which the compounds of the invention may be prepared.

Pharmaceutical Compositions

Another aspect of the present invention is directed to a pharmaceutical composition that includes a therapeutically effective amount of the bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bifunctional compounds of formula (I) may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the bifunctional compounds are formulated for oral or intravenous administration (e.g., systemic intravenous injection).

Accordingly, bifunctional compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bifunctional compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The inventive bifunctional compounds may be formulated for buccal or sublingual administration, examples of which include tablets, lozenges and gels.

The bifunctional compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bispecific compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the bifunctional compounds may be accomplished by means of an iontophoretic patch.

Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the bifunctional compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or a pharmaceutically acceptable salt or a stereoisomer thereof that is effective in producing the desired therapeutic response in a particular patient suffering from a disease or disorder mediated by aberrant protein (e.g., BRD2, BRD3, BRD4 and BRDT) activity. The term "therapeutically effective amount" thus includes the amount of a bifunctional compound of the present invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of aberrant protein in diseased cells.

The total daily dosage of the bifunctional compounds of formula (I) and usage thereof may be decided in accordance with standard medical practice, e.g., by the attending physician using sound medical judgment. The specific therapeutically effective dose for any particular patient will depend upon a variety of factors including the disease or disorder being treated and the severity thereof (e.g., its present status); the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", 10th Edition, A. Gilman, J. Hardman and L. Limbird, eds., McGraw-Hill Press, 155-173, 2001).

Bifunctional compounds of formula (I) and their pharmaceutically acceptable salts and stereoisomers may be effective over a wide dosage range. In some embodiments, the total daily dosage (e.g., for adult humans) may range from about 0.001 to about 1000 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving aberrant protein (that can be targeted for degradation by cereblon when bound to the bifunctional compound, participates in the inception, manifestation of one or more symptoms or markers, severity or progression of the disease or disorder) activity, that entails administration of a therapeutically effective amount of a bifunctional compound of formula (I) or a pharmaceutically acceptable salt or stereoisomer thereof, to a subject in need thereof. The diseases or disorders may be said to be characterized or mediated by aberrant protein activity (e.g., elevated protein levels compared to a non-pathological state). A "disease" is generally regarded as a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder.

Left untreated, a disorder does not necessarily cause a further decrease in the animal's state of health. In some embodiments, compounds of the application may be useful in the treatment of proliferative diseases and disorders (e.g., cancer or benign neoplasms). As used herein, the term "cell proliferative disease or disorder" refers to the conditions characterized by unregulated or abnormal cell growth, or both. Cell proliferative disorders include noncancerous conditions, precancerous conditions, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Bifunctional compounds of the present invention may be used to treat diseases or disorders characterized or mediated by aberrant activity of many different proteins, representative examples of which include the expression products of Ikaros family zinc finger protein 1 (IKZF1) and IKZF3, and the following proteins: casein kinase 1 alpha (CK1α), family with sequence similarity 83 member F (FAM83F), DTW domain containing 1 (DTWD1), zinc finger protein 91 homolog (ZFP91), ZFP62, ZFP36 ring finger protein like (ZFP36L2), ring finger protein 166 (RNF166), Ikaros family zinc finger protein 2 (IKZF2), IKZF4, IKZF5, Ras-related protein Rab-28 (RAB28), glutathione S-transferase pi 1 (GSTP1), GSPT2, mitochondrial import inner membrane translocase subunit Tim10 (TIMM10), GDNF inducible zinc finger protein 1 (GZF1), early growth response 1 (EGR1), hyper-methylated in cancer 1 (HIC1), HIC2, insulinoma-associated protein 2 (INSM2), odd-skipped related transcription factor 2 (OSR2), protein polybromo-1 (PB1), PR domain zinc finger protein 15 (PRD15), spalt-like transcription factor 1 (SALL1), SALL3, SALL4, WIZ, zinc finger and BTB domain-containing protein 17 (ZBT17), ZBT41, ZBT49, ZBT7A, ZBT7B, ZBTB2, ZBTB39, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483, SNF517, ZNF526, ZNF581, ZNF587, ZNF589, ZNF618, ZNF644, ZNF646, ZNF653, ZNF654, ZNF692, ZNF724, ZNF771, ZNF782, ZNF784, ZNF814, zinc finger and SCAN domain containing 10 (ZSC10), ZSC22, ZC827, and zinc finger with UFM1-specific peptidase domain (ZUFSP). In some embodiments, the disease or disorder is mediated by aberrant activity of IKZF2.

In some embodiments, the bifunctional compounds of the present invention may be used to treat diseases or disorders characterized or mediated by aberrant activity of Interleukin 1 Receptor Associated Kinase 1 (IRAK 1) and/or IRAK 4, KRAS, HRAS and NRAS (particularly G12C mutants), and bromodomain-containing proteins, e.g., extra terminal (BET) protein family which includes BRD2, BRD3, BRD4, and BRDT, as further disclosed hereinbelow. Yet other dysregulated or dysfunctional proteins that may be targeted by the bifunctional compounds of the present invention include B7.1 and B7, TINFR1m, TNFR2, NADPH oxidase, BclIBax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, trypanosomal GAPDH, glycogen phosphorylase, Carbonic anhydrase, chemokine receptors, JAW STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-αR, ICAM1, Cat+ channels, VCAM, VLA-4 integrin, selectins, CD40/CD40L, neurokinins and receptors, inosine monophosphate dehydrogenase, p38 MAP Kinase, Ras-Raf-MEK-ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5-α reductase inhibitors, angiotensin 11, glycine receptor, noradrenaline reuptake receptor, endothelin receptors, neuropeptide Y and receptor, adenosine receptors, adenosine kinase and AMP deaminase, purinergic receptors (P2Y1, P2Y2, P2Y4, P2Y6, P2X1-7), farnesyltransferases, geranylgeranyl transferase, TrkA receptor for NGF, β-amyloid, tyrosine kinase Flk-IIKDR, vitronectin receptor, integrin receptor, Her-21 neu, telomerase inhibition, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium release channel, chloride channels, acetyl-CoA carboxylase, adenylosuccinate synthetase, protoporphyrinogen oxidase and enolpyruvylshikimate-phosphate synthase.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, autoimmune thyroiditis or Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cerebral malaria, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, graft-versus-host reaction, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefelter's syndrome, neurofibromatosis, phenylketonuria, Prader-Willi syndrome, sudden infant death syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, cystic fibrosis, uveitis, polymyositis, proctitis, interstitial lung fibrosis, dermatomyositis, arteriosclerosis, amyotrophic lateral sclerosis, asocality, immune response, varicosis, vaginitis, including chronic recurrent yeast vaginitis, depression, and Sudden Infant Death Syndrome.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) including leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, gestational trophoblastic tumor glioma, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinemia, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver (hepatocellular), brain, lung, colorectal (e.g., colon), pancreas, prostate, skin, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, primary CNS lymphoma (PCNSL), marginal zone lymphoma (MZL), leukemia, including chronic lymphocytic leukemia (CLL), childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver (hepatocellular)" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the brain may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, a precancer or precancerous condition of the lung, benign growths or lesions of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioloalveolar carcinoma, giant cell carcinoma, spindle cell carcinoma, and large cell neuroendocrine carcinoma. Lung cancer includes lung neoplasms having histologic and ultrastructural heterogeneity (e.g., mixed cell types).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer. Colon cancer includes malignant colon neoplasms, carcinoma in situ, typical carcinoid tumors, and atypical carcinoid tumors. Colon cancer includes adenocarcinoma, squamous cell carcinoma, and squamous cell carcinoma. Colon cancer can be associated with a hereditary syndrome such as hereditary nonpolyposis colorectal cancer, familiar adenomatous polyposis, MYH-associated polyposis, Gardner's syndrome, Peutz-Jeghers syndrome, Turcot's syndrome and juvenile polyposis. Cell proliferative disorders of the colon can be characterized by hyperplasia, metaplasia, and dysplasia of the colon.

As used herein, "cell proliferative diseases or disorders of the pancreas" include all forms of cell proliferative disorders affecting pancreatic cells. Cell proliferative disorders of the pancreas may include pancreatic cancer, an precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting the endometrium. Cell proliferative disorders of the endometrium may include endometrial cancer, a precancer or precancerous condition of the endometrium, benign growths or lesions of the endometrium, and malignant growths or lesions of the endometrium, and metastatic lesions in tissue and organs in the body other than the endometrium. Cell proliferative disorders of the endometrium may include hyperplasia, metaplasia, and dysplasia of the endometrium.

In some embodiments, wherein the method entails use of a bifunctional compound of formula (I) that targets a BRD protein, the subject may have a cancer e.g., NUT midline carcinoma, treatment-refractory acute myeloid leukemia, myelodysplastic syndrome, multiple myeloma, triple negative- and estrogen receptor-positive breast cancers, small cell and non-small cell lung cancers, castration resistant prostate cancer, pancreatic ductal adenocarcinoma, colorectal cancer, neuroblastoma and N-Myc Proto-Oncogene Protein (MYCN)-driven solid tumors.

Bifunctional compounds of formula (I) may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present application may entail administration of compounds of the invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks.

In some embodiments, the frequency of administration ranges from about once a day for 1, 2, 3, 4, 5 or 6 weeks, and in other embodiments entails a 28-day cycle which includes daily administration for 3 weeks (21 days).

Combination Therapy

Bifunctional compounds of formula (I) may be used in combination with at least one other active agent, e.g., anti-cancer agent or regimen, in treating diseases and disorders. The term "in combination" in this context means that the agents are co-administered, which includes substantially contemporaneous administration, by the same or separate dosage forms, or sequentially, e.g., as part of the same treatment regimen or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bifunctional compound of formula (I) in combination with one or more therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics*, 10th ed., McGraw-Hill, New York, 2001; Physician's Desk Reference 60th ed., 2006. Anti-cancer agents that may be used in combination with the inventive compounds are known in the art. See, e.g., U.S. Pat. No. 9,101,622 (Section 5.2 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the bifunctional compound of formula (I) and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anti-cancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the bifunctional compound of formula (I) or a pharmaceutical composition. The kits or pharmaceutical systems of the invention may also include printed instructions for using the compounds and compositions.

These and other aspects of the present application will be further appreciated upon consideration of the following Examples, which are intended to illustrate certain particular embodiments of the application but are not intended to limit its scope, as defined by the claims.

EXAMPLES

Example 1: Synthesis of 2-(2,6-dioxopiperidin-3-yl)-1H-benzo[de]isoquinoline-1,3(2H)-dione (9)

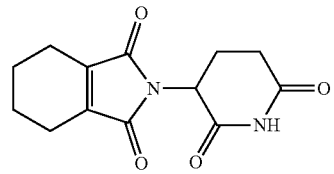

2-(2,6-Dioxopiperidin-3-yl)-4,5,6,7-tetrahydro-1H-isoindole-1,3(2H)-dione

Aminoglutarimide (56.1 mg, 0.44 mmol) and NaOAc (43.2 mg, 0.53 mmol) were added to a solution of tetrahydrophthalic anhydride (100 mg, 0.66 mmol) in acetic acid (2 mL) at room temperature (rt). The resulting mixture was heated at reflux for 5 hours (h). The solvent was removed under reduced pressure, and the crude product was purified with HPLC to yield the title compound.

$^1$H NMR (500 MHz, DMSO-$d_6$) δ 11.04 (s, 1H), 4.92 (dd, J=13.0, 5.4 Hz, 1H), 2.92-2.76 (m, 1H), 2.56 (dt, J=17.6, 3.2 Hz, 1H), 2.47-2.35 (m, 1H), 2.28 (s, 4H), 2.01-1.87 (m, 1H), 1.70 (s, 4H).

LC/MS m/z calculated for [M+H]$^+$ 263.1, found 262.9.

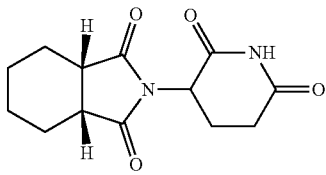

Cis-2-(2,6-dioxopiperidin-3-yl)hexahydro-1H-isoindole-1,3(2H)-dione

Aminoglutarimide (56.1 mg, 0.44 mmol) and NaOAc (43.2 mg, 0.53 mmol) were added to the solution of tetrahydrophthalic anhydride (100 mg, 0.66 mmol) in acetic acid (2 mL) at room temperature. The resulting mixture was heated at reflux for 5 h. The solvent was evaporated, and the crude product was purified with HPLC to yield the title compound.

$^1$H NMR (500 MHz, DMSO-$d_6$) δ 11.03 (s, 1H), 4.91 (dd, J=12.8, 5.5 Hz, 1H), 3.13-2.90 (m, 2H), 2.91-2.70 (m, 1H), 2.56-2.53 (m, 1H), 2.50-2.25 (m, 1H), 1.98-1.82 (m, 1H), 1.80-1.52 (m, 4H), 1.53-1.10 (m, 4H).

LC/MS m/z calculated for [M+H]$^+$ 265.1, found for [M+H]$^+$ 264.9.

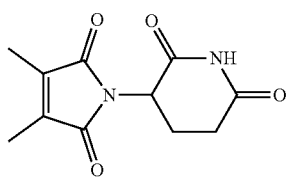

3-(3,4-Dimethyl-2-5-dio-2,5-dihydro-1H-pyrrol-1-yl)piperidine-2,6-dione

Aminoglutarimide (87 mg, 0.53 mmol) and NaOAc (52 mg, 0.63 mmol) were added to a solution of 3,4-dimethylfuran-2,5-dione (100 mg, 0.79 mmol) in acetic acid (2 mL) at room temperature. The resulting mixture was heated at reflux for 5 h. The solvent was evaporated, and the crude product was purified with HPLC to yield the title compound.

$^1$H NMR (500 MHz, DMSO-$d_6$) δ 11.05 (s, 1H), 4.92 (dd, J=13.0, 5.4 Hz, 1H), 2.84 (ddd, J=17.2, 13.9, 5.5 Hz, 1H), 2.67-2.53 (m, 1H), 2.51 (s, 1H), 2.42 (qd, J=13.3, 4.6 Hz, 1H), 1.93 (s, 6H).

LC/MS m/z calculated for [M+H]$^+$ 237.1, found for [M+H]$^+$ 237.1.

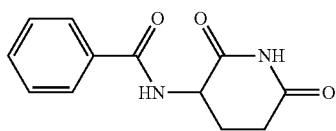

N-(2,6-Dioxopiperidin-3-yl)benzamide

1-[Bis(dimethylamino)methylene]-1H-1,2,3-triazolo[4,5-b]pyridinium-3-oxid hexafluorophosphate (HATU) (2.31 g, 6.08 mmol), 1-Hydroxy-7-azabenzotriazole (HOAt) (83 mg, 0.61 mmol) and N,N-Diisopropylethylamine (DIPEA) (1.96 g, 15.2 mmol) were added to a solution of benzoic acid (371 mg, 3.04 mmol) and 3-aminopiperidine-2,6-dione HCl salt (500 mg, 3.04 mmol) in DCM (12 mL) at 0° C. The resulting mixture was stirred at room temperature for 1 h. The solvent was evaporated, and the crude product was purified with HPLC to yield the title compound.

$^1$H NMR (500 MHz, DMSO-$d_6$) δ 10.86 (s, 1H), 8.76 (d, J=8.3 Hz, 1H), 7.87 (d, J=7.6 Hz, 2H), 7.56 (t, J=7.3 Hz, 1H), 7.49 (t, J=7.5 Hz, 2H), 4.79 (ddd, J=13.0, 8.3, 5.4 Hz, 1H), 2.80 (ddd, J=18.1, 13.3, 5.5 Hz, 1H), 2.55 (dt, J=17.5, 3.7 Hz, 1H), 2.13 (qd, J=12.9, 4.5 Hz, 1H), 2.04-1.93 (m, 1H).

LC/MS m/z calculated for [M+H]$^+$ 233.1, found 233.1.

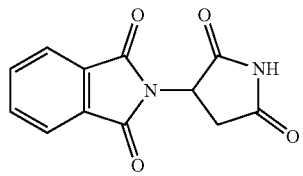

2-(2,5-Dioxopyrrolidin-3-yl)isoindole-1,3-dione 3-aminopyrrolidine-2,5-dione (229 mg, 2.01 mmol) and NaOAc (197 mg, 2.41 mmol) were added to a solution of phthalic anhydride (447 mg, 3.02 mmol) in AcOH (8 mL). The resulting mixture was heated at 90° C. for 12 h. The solvent was evaporated, and the crude product was purified with HPLC to yield the title compound.

$^1$H NMR (500 MHz, CDCl$_3$) δ 8.10 (s, 1H), 7.92 (dd, J=5.5, 3.1 Hz, 2H), 7.81 (dd, J=5.5, 3.0 Hz, 2H), 5.31 (dd, J=9.6, 6.4 Hz, 1H), 3.36-2.89 (m, 2H).

LC/MS m/z calculated for [M+H]$^+$ 245.0, found 245.0.

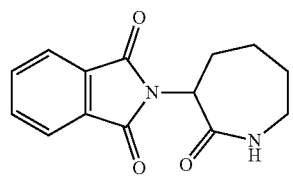

2-(2-Oxoazepan-3-yl)isoindoline-1,3-dione 3-aminoazepan-2-one HCl salt (950 mg, 4.73 mmol) and phthalic anhydride (1.05 g, 7.09 mmol) were added to a solution of NaOAc (465 mg, 5.68 mmol) in AcOH (20 mL). The resulting mixture was heated at 90° C. for 2 h. The solvent was evaporated, and the crude product was purified with silica flash chromatography (0-100% Hexane/EtOAc) to yield the title compound.

$^1$H NMR (500 MHz, DMSO-$d_6$) δ 8.01-7.64 (m, 5H), 4.83 (d, J=11.6 Hz, 1H), 3.28-3.16 (m, 1H), 3.18-3.01 (m, 1H), 2.41 (q, J=12.3, 11.3 Hz, 1H), 2.23-1.92 (m, 2H), 1.81 (dd, J=14.4, 4.4 Hz, 1H), 1.66 (q, J=13.7, 13.3 Hz, 1H), 1.33 (q, J=12.7 Hz, 1H). LC/MS m/z calculated for [M+H]$^+$ 259.1, found 259.1.

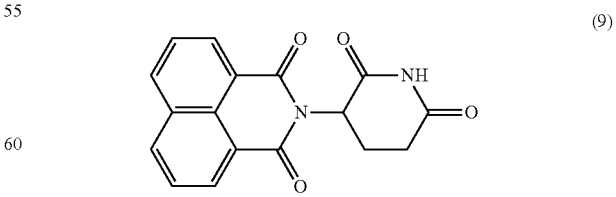

(9)

Aminoglutarimide (415 mg, 2.52 mmol) and triethylamine (521 mg, 4.03 mmol) were added to a solution of naphthalic anhydride (500 mg, 2.52 mmol) in THF (10 mL). The resulting mixture was heated at 75° C. for 2 days. The solvent was evaporated, and the crude product was purified with prep-HPLC to yield compound 9.

¹H NMR (500 MHz, DMSO-d₆) δ 11.01 (s, 1H), 8.84-8.29 (m, 4H), 7.92 (q, J=8.6 Hz, 2H), 5.85 (dd, J=11.6, 5.8 Hz, 1H), 2.94 (ddd, J=18.1, 15.2, 5.5 Hz, 1H), 2.77-2.44 (m, 2H), 2.30-1.83 (m, 1H).

LC/MS m/z calculated for [M+H]⁺ 309.1, found 309.1.

Example 2: Synthesis of 5-amino-2-(2,6-dioxopiperidin-3-yl)-1H-benzo[de]isoquinoline-1,3(2H)-dione (11)

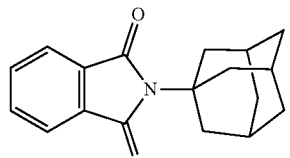

2-(Amantadine-yl)isoindoline-1,3-dione

Amantadine (500 mg, 3.31 mmol) and triethylamine (684 mg, 5.30 mmol) were added to a solution of phthalic anhydride (490.2 mg, 3.31 mmol) in THF (12 mL). The resulting mixture was heated at 75° C. for three days. The solvent was evaporated, and the crude product was purified with prep-HPLC to yield the title compound.

¹H NMR (500 MHz, DMSO-d₆): δ 7.81-7.76 (m, 4H), 2.44 (d, J=2.8 Hz, 6H), 2.14-2.09 (m, 3H), 1.73-1.66 (m, 6H).

LC/MS m/z calculated for [M+H]⁺ 282.1, found 282.0.

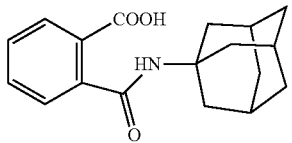

2-(amantadine-ylcarbamoyl)benzoic acid

Amantadine (500 mg, 3.31 mmol) and triethylamine (684 mg, 5.30 mmol) were added to a solution of phthalic anhydride (490.2 mg, 3.31 mmol) in THF (12 mL). The resulting mixture was heated at 75° C. for one day. The solvent was evaporated, and the crude product was purified with prep-HPLC to yield the title compound.

¹H NMR (500 MHz, DMSO-d₆): δ 7.74-7.72 (m, 1H), 7.54-7.43 (m, 2H), 7.34-7.32 (m, 1H), 2.03 (s, 9H), 1.64 (s, 6H), 1.73-1.66 (m, 6H).

LC/MS m/z calculated for [M+H]⁺ 300.2, found 300.2.

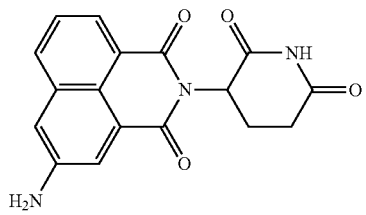

Aminoglutarimide (135 mg, 0.82 mmol) and triethylamine (248 mg, 2.46 mmol) were added to a solution of 5-hydroxybenzo[de]isochromene-1,3-dione (200 mg, 0.82 mmol) in THF (3 mL). The resulting mixture was heated at 75° C. for 1 h. The solvent was evaporated to afford a grey (MASS g, 0.80 mmol). The crude product was redissolved in EtOH/H₂O (5 mL/1 mL) in a 100 mL flask. NH₄Cl (342 mg, 6.4 mmol) and iron powder (90 mg, 1.6 mmol) were added to the solution at room temperature before heating the mixture at 80° C. for 2 h. Additional iron powder (180 mg, 3.2 mmol) was added to the reaction mixture. After 3 h, the reaction was filtered and the obtained solid washed with ethyl acetate. The pooled filtrate was evaporated, and the crude product was purified with prep-HPLC to yield compound 11.

¹H NMR (500 MHz, DMSO-d₆) δ 10.91 (d, J=3.5 Hz, 1H), 8.16-7.80 (m, 3H), 7.58 (dt, J=10.1, 7.8 Hz, 1H), 7.26 (t, J=2.8 Hz, 1H), 5.73 (dd, J=12.0, 5.8 Hz, 1H), 2.86 (ddd, J=17.7, 14.7, 5.6 Hz, 1H), 2.58-2.46 (m, 2H), 2.01-1.89 (m, 1H).

LC/MS m/z calculated for [M+H]⁺ 324.1, found 324.1.

Example 3: Synthesis of 2-(2,6-dioxopiperidin-3-yl)-5-hydroxy-1H-benzo[de]isoquinoline-1,3(2H)-dione (10)

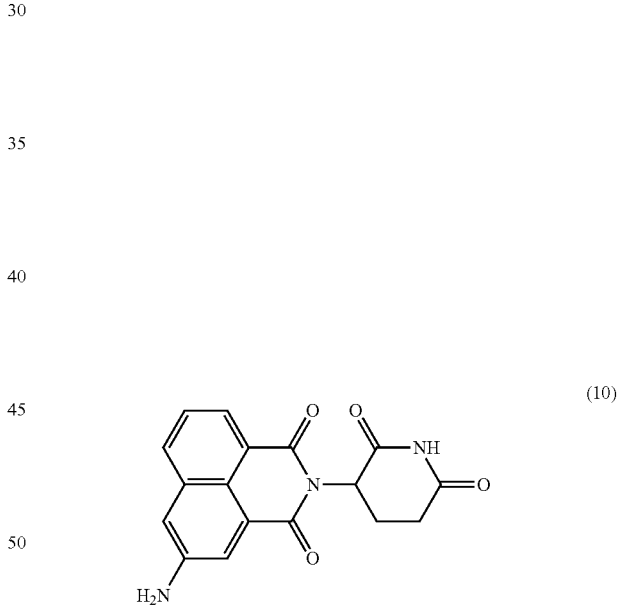

Aminoglutarimide (165 mg, 1.0 mmol) and triethylamine (202 mg, 2.0 mmol) were added to a solution of 5-hydroxy-benzo[de]isochromene-1,3-dione (214 mg, 1.0 mmol) in THF (5 mL). The resulting mixture was heated at 75° C. for 1 h. The solvent was evaporated, and the crude product was purified with prep-HPLC to yield compound 10.

¹H NMR (500 MHz, DMSO-d₆) δ 10.93 (s, 1H), 8.36-8.12 (m, 2H), 7.98 (dd, J=55.8, 2.5 Hz, 1H), 7.71 (dt, J=9.9, 7.7 Hz, 1H), 7.65 (dd, J=4.6, 2.4 Hz, 1H), 5.92-5.56 (m, 1H), 2.95-2.78 (m, 1H), 2.60-2.46 (m, 2H), 1.97 (dd, J=11.8, 5.9 Hz, 1H).

LC/MS m/z calculated for [M+H]⁺ 325.1, found 325.1.

Example 4: Synthesis of methyl 2-((6S)-4-(4-chlorophenyl)-2-((5-((2-(2,6-dioxopiperidin-3-yl)-1,3-dioxo-2,3-dihydro-1H-benzo[de]isoquinolin-5-yl)oxy)pentyl)carbamoyl)-3,9-dimethyl-6H-thieno[3,2-f][1,2,4]triazolo[4,3-a][1,4]diazepin-6-yl)acetate (1)

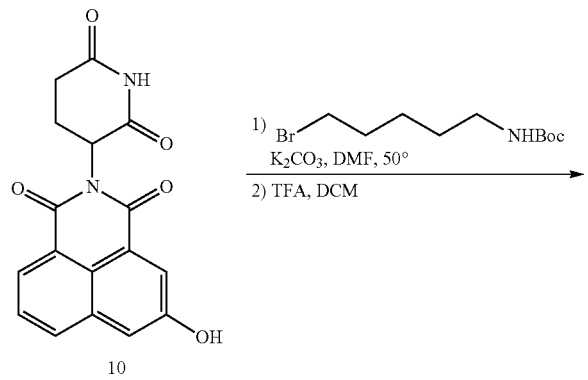

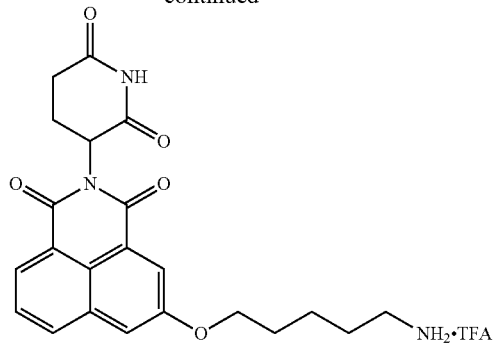

To a solution of 10 (100 mg, 0.31 mmol) and tert-butyl 5-bromopentylcarbamate (82 mg, 0.31 mmol) in DMF (2 mL), $K_2CO_3$ (64 mg, 0.46 mmol) was added at room temperature. The mixture was heated to 50° C. overnight. The reaction was allowed to cool to room temperature before quenching with ice water. The mixture was stirred at 0° C. for 1 hour. The suspension was filtered, and the precipitate was washed with ice water to yield the crude product. To a suspension of the crude product in DCM (2 mL), TFA (1 mL) was slowly added at room temperature. The mixture was stirred for 1 hour. The solvent was removed under reduced pressure to obtain the titled crude product without any purification.

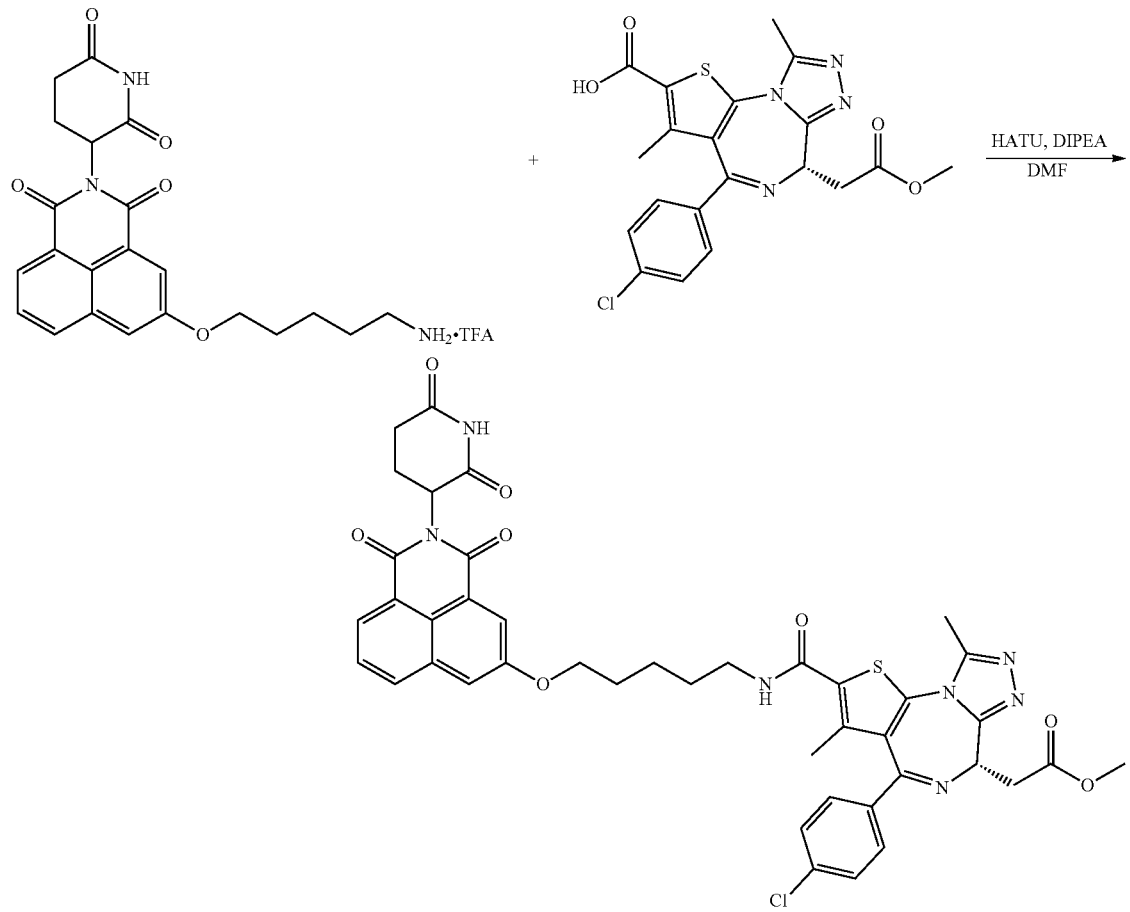

To a solution of 5-(5-aminopentyloxy)-2-(2,6-dioxopiperidin-3-yl)-1H-benzo[de]isoquinoline-1,3(2H)-dione TFA salt (20.4 mg, 0.039 mmol) and (6S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (17 mg, 0.039 mmol) in DMF (1 mL) at 0° C. was added HATU (30 mg, 0.078 mmol) and DIEA (25 mg, 0.195 mmol) The solution was allowed to warm up to room temperature. The mixture was stirred for 10 mins before removing the solvent under reduced pressure. The residue was purified with HPLC to yield compound 1.

¹H NMR (500 MHz, DMSO-d₆) δ 10.94 (d, J=3.9 Hz, 1H), 8.39-8.15 (m, 3H), 8.05-7.87 (m, 2H), 7.77 (dt, J=10.0, 7.7 Hz, 1H), 7.49-7.32 (m, 4H), 5.83-5.63 (m, 1H), 4.50 (t, J=7.2 Hz, 1H), 4.16 (d, J=5.9 Hz, 2H), 3.60 (s, 3H), 3.39 (qd, J=16.6, 7.2 Hz, 2H), 3.24 (d, J=7.3 Hz, 2H), 2.87 (ddd, J=17.8, 14.6, 5.7 Hz, 1H), 2.61-2.45 (m, 5H), 1.97 (d, J=9.9 Hz, 1H), 1.85 (s, 3H), 1.83-1.75 (2H), 1.63-1.39 (m, 4H).

LC/MS m/z calculated for [M+H]⁺ 836.2, found 836.2.

Example 5: Synthesis of 2-((S)-4-(4-chlorophenyl)-2,3,9-trimethyl-6H-thieno[3,2-f][1,2,4]triazolo[4,3-a][1,4]diazepin-6-yl)-N-(8-((2-(2,6-dioxopiperidin-3-yl)-1,3-dioxo-2,3-dihydro-1H-benzo[de]isoquinolin-6-yl)amino)octyl)acetamide (6)

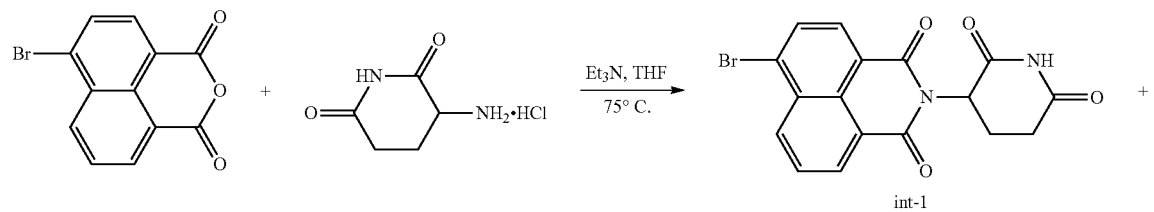

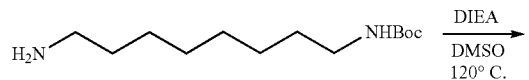

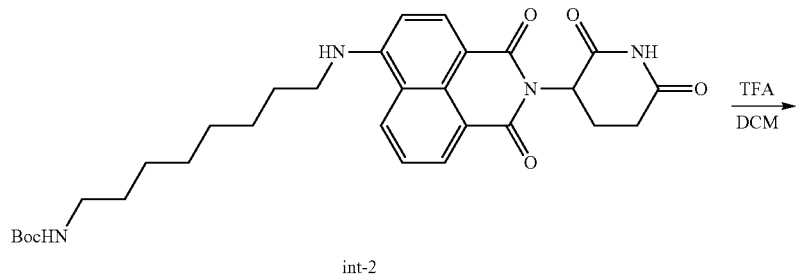

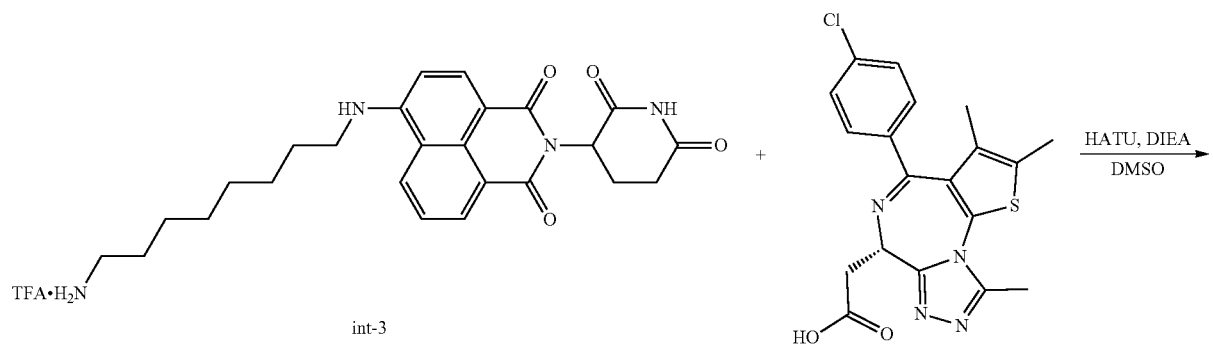

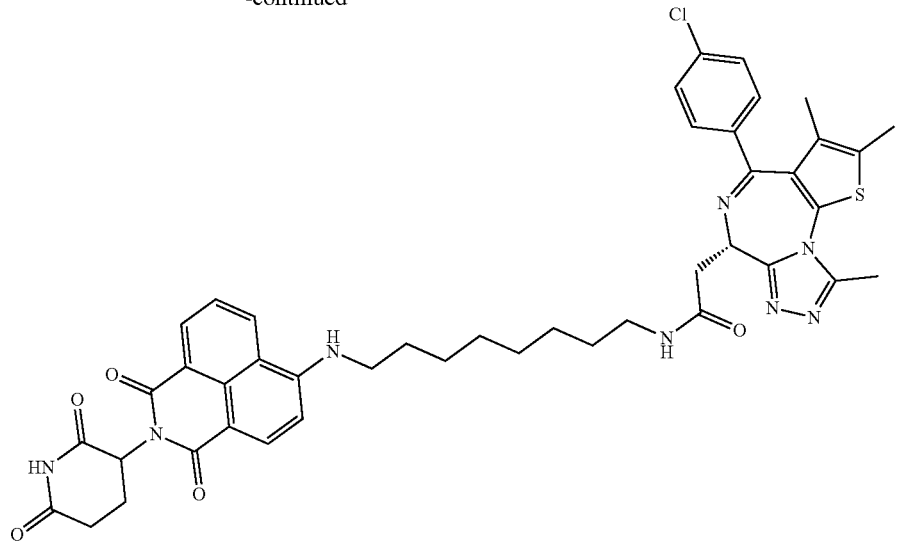

6

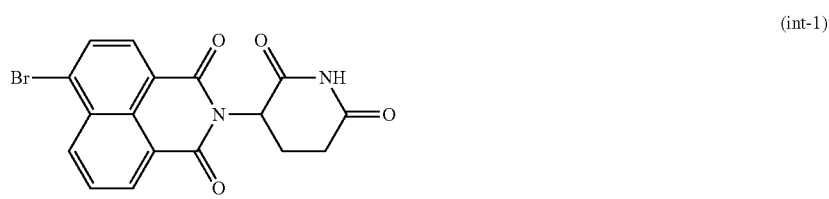
(int-1)

To a solution of 6-bromo-1H,3H-benzo[de]isochromene-1,3-dione (277 mg, 1 mmol) and 3-aminopiperidine-2,6-dione hydrochloride (165 mg, 1 mmol) in 10 mL THF was added Et$_3$N (415 µL, 3 mmol), the mixture was stirred at 75° C. overnight. After finished, the mixture was concentrated in vacuo to get the crude product int-1 without any purification.

LCMS (m/z): 386 [M+H]$^+$.

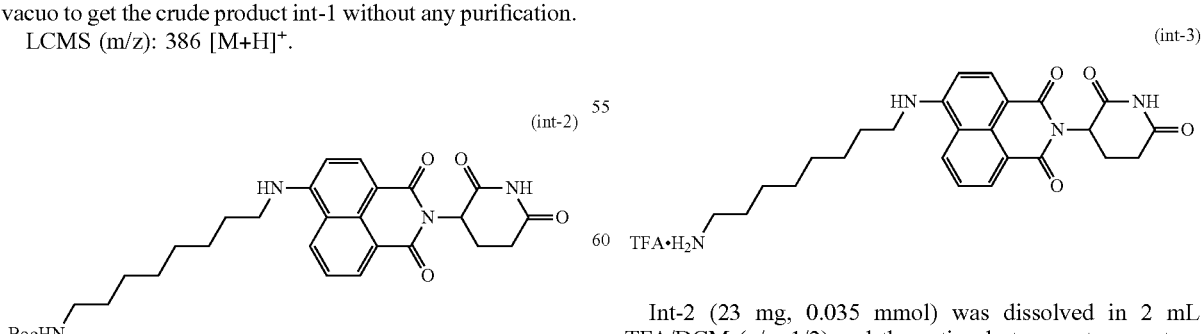
(int-2)

(int-3)

To a solution of int-1 (38 mg, 0.1 mmol) and tert-butyl (8-aminooctyl)carbamate (24 mg, 0.1 mmol) in 1 mL DMSO was added DIEA (33 µL, 0.2 mmol), the mixture was stirred at 120° C. for 1 h, then purified by prep-HPLC (MeOH/H$_2$O, 0.05% TFA) to obtain int-2 (23 mg, 35%).

LCMS (m/z): 551 [M+H]$^+$.

Int-2 (23 mg, 0.035 mmol) was dissolved in 2 mL TFA/DCM (v/v=1/2) and then stirred at room temperature for 1 h, then concentrated in vacuo to get the product int-3, which was used to next step without any purification.

LCMS (m/z): 451 [M+H]$^+$.

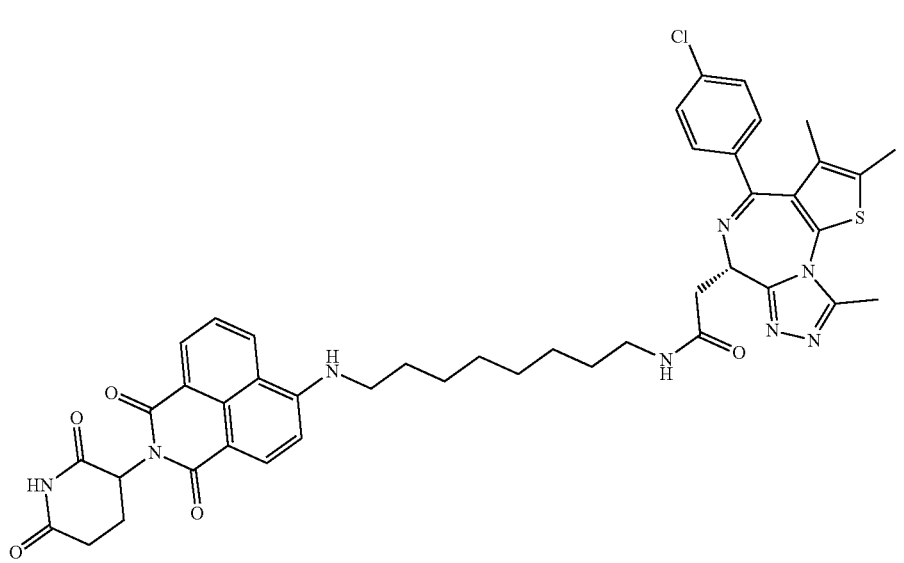

(6)

To a solution of int-3 (0.035 mmol) and (S)-2-(4-(4-chlorophenyl)-2,3,9-trimethyl-6H-thieno[3,2-f][1,2,4]triazolo[4,3-a][1,4]diazepin-6-yl)acetic acid (14 mg, 0.035 mmol) in 2 mL DMSO were added HATU (16 mg, 0.042 mmol) and DIEA (17 μL, 0.105 mmol), the mixture was stirred at room temperature for 30 min and then purified by prep-HPLC (MeOH/H$_2$O, 0.05% TFA) to obtain 6 (10.3 mg, 31%).

$^1$H NMR (500 MHz, DMSO-d$_6$) δ 10.93 (d, J=10.9 Hz, 1H), 8.75 (dd, J=8.5, 3.8 Hz, 1H), 8.35 (dd, J=29.3, 7.9 Hz, 1H), 8.18 (q, J=5.8, 4.0 Hz, 1H), 7.88 (s, 1H), 7.70 (dt, J=10.1, 7.8 Hz, 1H), 7.47 (d, J=8.4 Hz, 2H), 7.42 (d, J=8.4 Hz, 2H), 6.79 (t, J=9.1 Hz, OH), 5.79 (ddd, J=24.9, 11.7, 5.8 Hz, 1H), 4.51 (dd, J=8.2, 5.9 Hz, 1H), 3.37 (d, J=7.8 Hz, 2H), 3.30-3.05 (m, 5H), 2.97-2.87 (m, 1H), 2.65-2.55 (m, 5H), 2.38 (s, 3H), 1.98 (dt, J=11.6, 5.7 Hz, 1H), 1.70 (q, J=6.6, 6.0 Hz, 2H), 1.60 (s, 3H), 1.43 (dt, J=22.3, 6.9 Hz, 4H), 1.31 (s, 6H).

LCMS (m/z): 833 [M+H]$^+$.

Example 6: Synthesis of 2-((S)-4-(4-chlorophenyl)-2,3,9-trimethyl-6H-thieno[3,2-f][1,2,4]triazolo[4,3-a][1,4]diazepin-6-yl)-N-(2-(2-(2-(2-((2-(2,6-dioxopiperidin-3-yl)-1,3-dioxo-2,3-dihydro-1H-benzo[de]isoquinolin-5-yl)oxy)ethoxy)ethoxy)ethoxy)ethyl)acetamide (7)

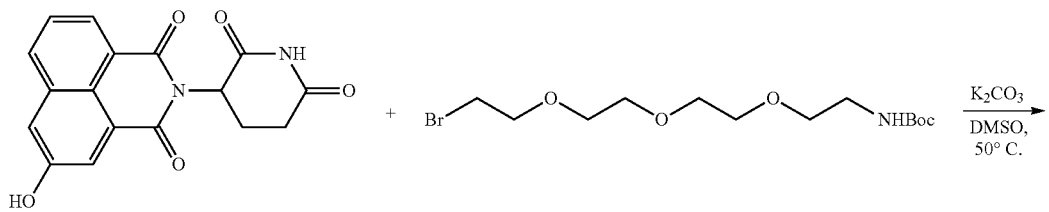

63
64
-continued
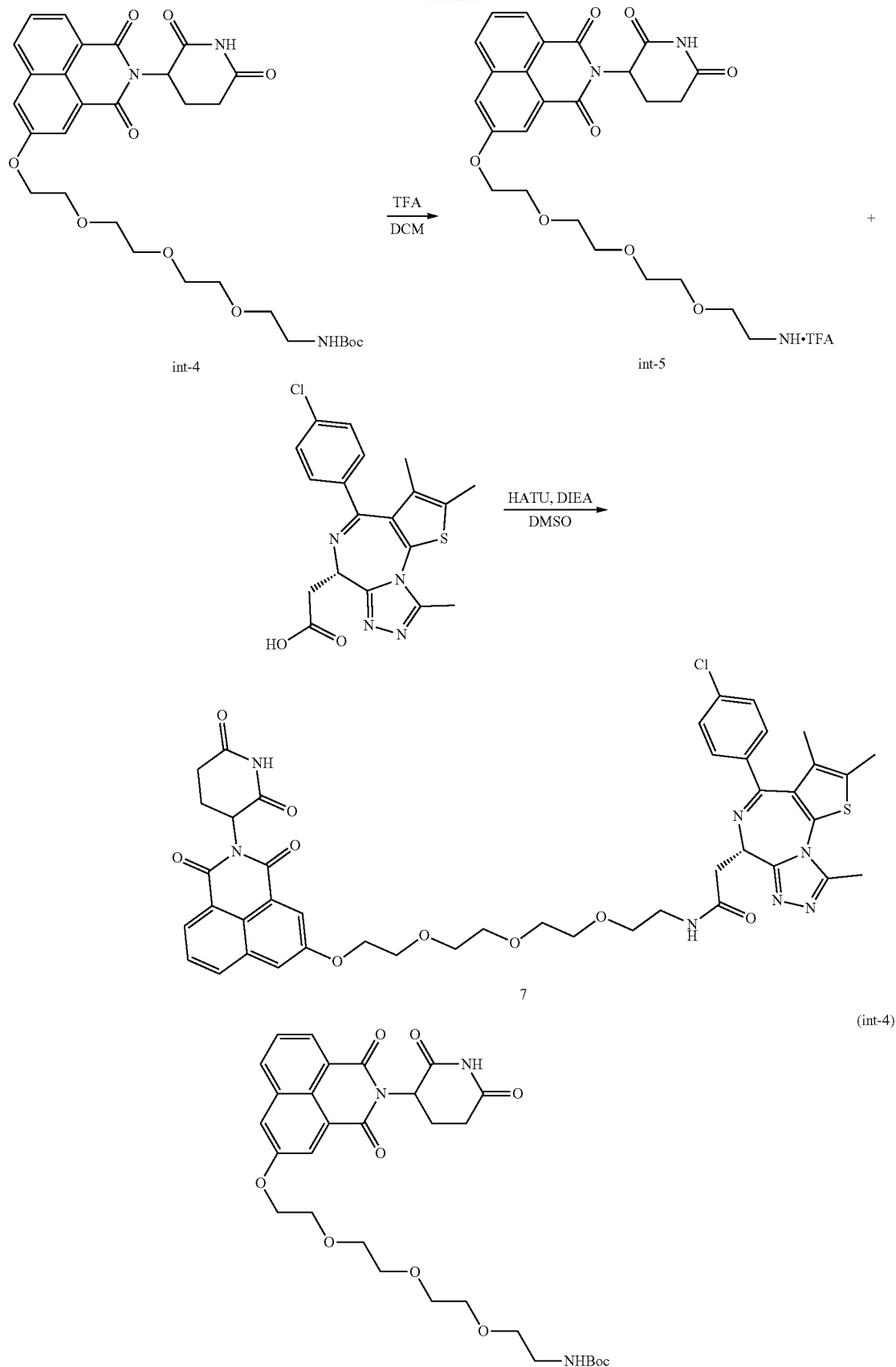

To a solution of 10 (65 mg, 0.2 mmol) and tert-butyl (2-(2-(2-(2-bromoethoxy)ethoxy)ethoxy)ethyl)carbamate (71 mg, 0.2 mmol) in 2 mL DMSO was added K$_2$CO$_3$ (83 mg, 0.6 mmol), the mixture was stirred at 50° C. overnight. The mixture was filtered, and then purified by prep-HPLC (MeOH/H$_2$O, 0.05% TFA) to obtain int-4 (32 mg, 22%).

LCMS (m/z): 600 [M+H]$^+$.

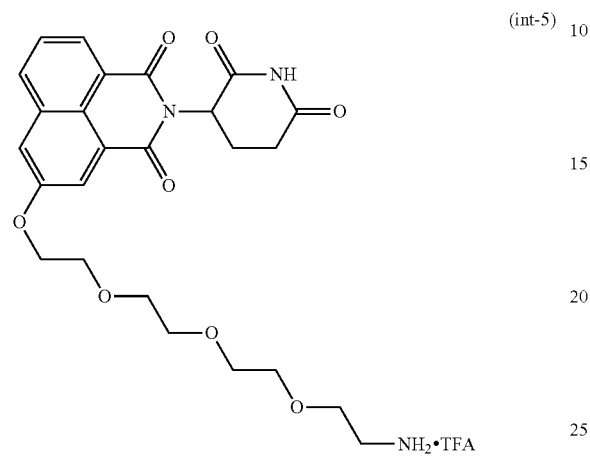

(int-5)

Int-4 (32 mg, 0.045 mmol) was dissolved in 2 mL TFA/DCM (v/v=1/2) and then stirred at room temperature for 1 h, then concentrated in vacuo to get the product int-5 (20 mg, 74%).

LCMS (m/z): 500 [M+H]$^+$.

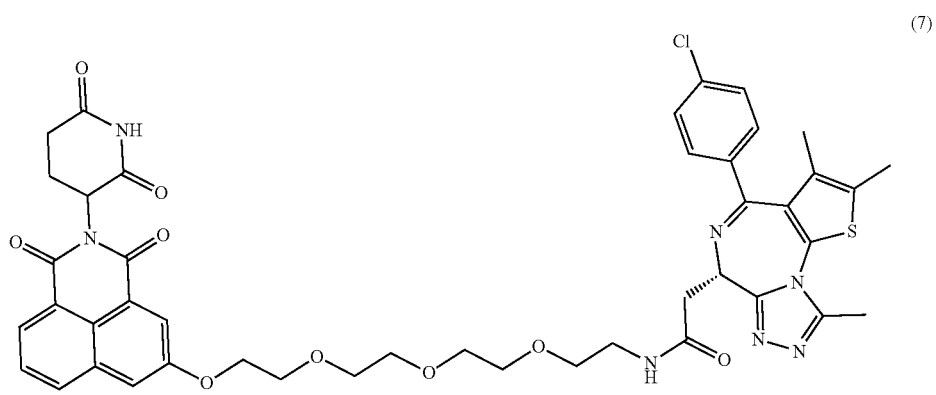 [SMILES: Cc1sc2c(c1C)C(c1ccc(Cl)cc1)=N[C@@H](CC(=O)NCCOCCOCCOCCOc1cc3c4c(cccc4c1)C(=O)N(C1CCC(=O)NC1=O)C3=O)c1nnc(C)n1-2]

(7)

To a solution of int-5 (15 mg, 0.025 mmol) and (S)-2-(4-(4-chlorophenyl)-2,3,9-trimethyl-6H-thieno[3,2-f][1,2,4]triazolo[4,3-a][1,4]diazepin-6-yl)acetic acid (10 mg, 0.025 mmol) in 1 mL DMSO were added HATU (11 mg, 0.03 mmol) and DIEA (12 µL, 0.075 mmol), the mixture was stirred at room temperature for 30 min and then purified by prep-HPLC (MeOH/H$_2$O, 0.05% TFA) to obtain 7 (13 mg, 52%).

$^1$H NMR (500 MHz, DMSO-d$_6$) δ 11.02 (s, 1H), 8.26 (t, J=6.3 Hz, 1H), 8.00 (s, 1H), 7.83 (q, J=8.4 Hz, 1H), 7.47 (d, J=8.5 Hz, 2H), 7.41 (d, J=8.2 Hz, 2H), 5.83 (dt, J=11.6, 5.9 Hz, 1H), 5.76 (d, J=1.1 Hz, 2H), 4.50 (t, J=7.0 Hz, 1H), 4.35 (q, J=5.0, 4.5 Hz, 2H), 4.10 (q, J=5.2 Hz, 1H), 3.86 (d, J=4.8 Hz, 2H), 3.65 (d, J=4.1 Hz, 2H), 3.61-3.50 (m, 8H), 3.45 (d, J=5.5 Hz, 2H), 3.18 (d, J=5.1 Hz, 2H), 2.99-2.87 (m, 1H), 2.59 (s, 5H), 2.39 (s, 3H), 2.08-2.03 (m, 1H), 1.60 (s, 3H).

LCMS (m/z): 882 [M+H]$^+$.

Example 7: Synthesis of 2-((S)-4-(4-chlorophenyl)-2,3,9-trimethyl-6H-thieno[3,2-f][1,2,4]triazolo[4,3-a][1,4]diazepin-6-yl)-N-(6-((2-(2,6-dioxopiperidin-3-yl)-1,3-dioxo-2,3-dihydro-1H-benzo[de]isoquinolin-5-yl)oxy)hexyl)acetamide (8)
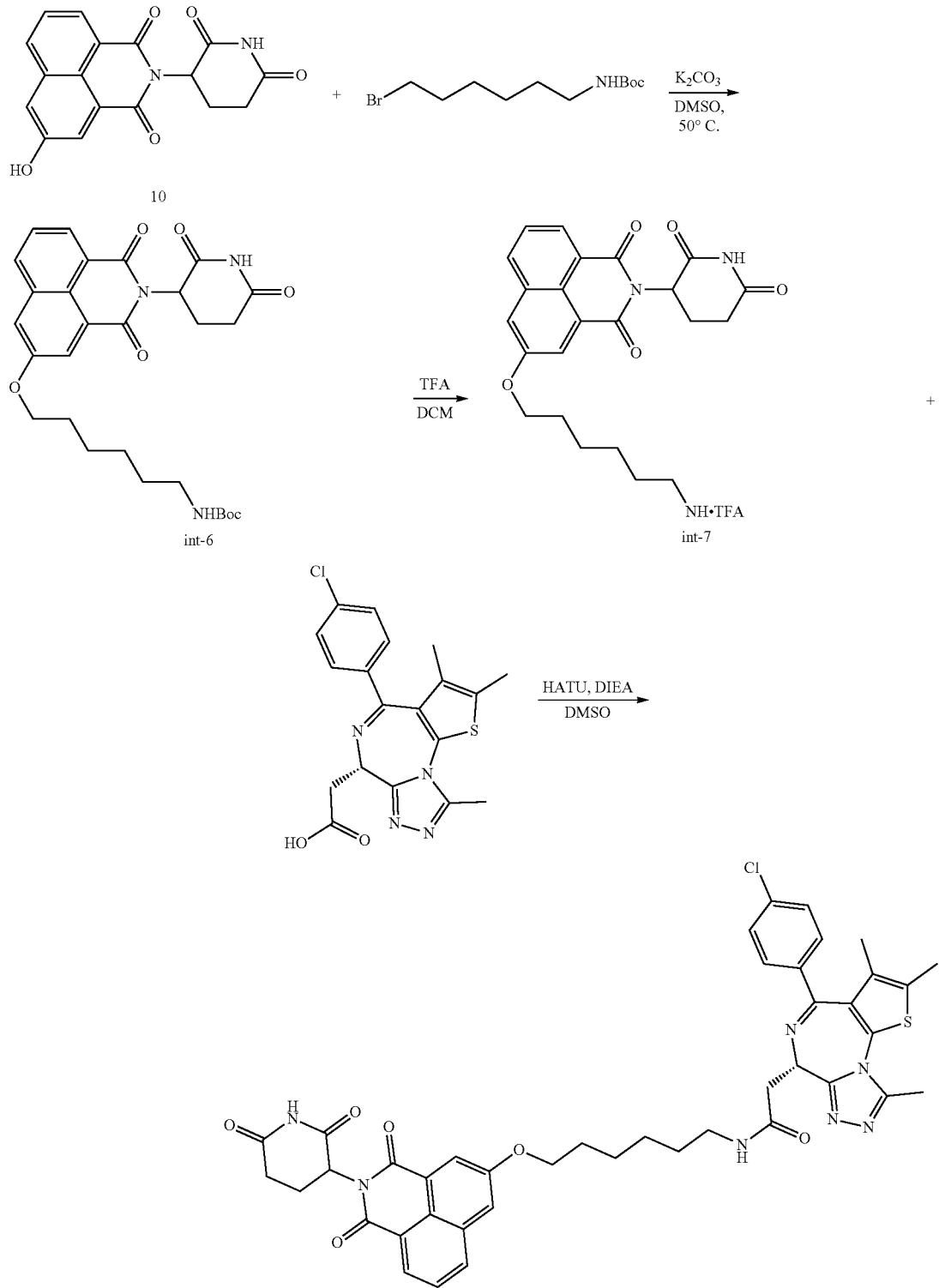

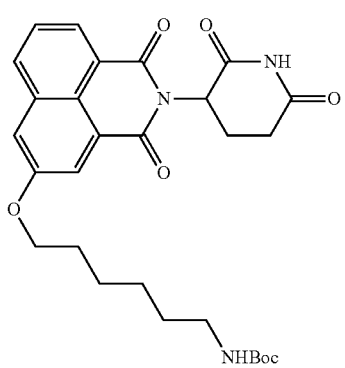
(int-6)

To a solution of 10 (100 mg, 0.3 mmol) and tert-butyl (6-bromohexyl)carbamate (84 mg, 0.3 mmol) in 3 mL DMSO was added $K_2CO_3$ (124 mg, 0.9 mmol), the mixture was stirred at 50° C. overnight. The mixture was filtered, and then purified by prep-HPLC (MeOH/$H_2O$, 0.05% TFA) to obtain int-6 (47 mg, 25%).

LCMS (m/z): 524 $[M+H]^+$.

(int-7)

Int-6 (47 mg, 0.07 mmol) was dissolved in 2 mL TFA/DCM (v/v=1/2) and then stirred at 50° C. for 2 days, then concentrated in vacuo to get the product int-7 (30 mg, 80%).

LCMS (m/z): 424 $[M+H]^+$

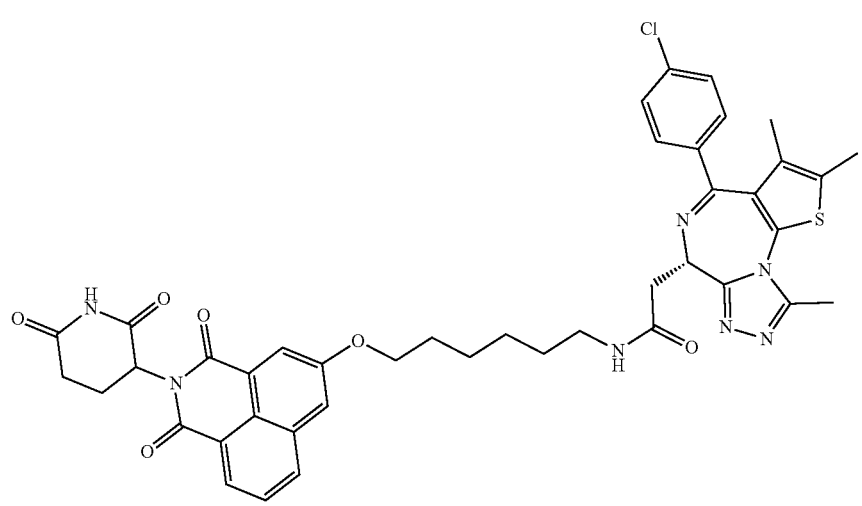
(8)

To a solution of int-7 (13 mg, 0.025 mmol) and (S)-2-(4-(4-chlorophenyl)-2,3,9-trimethyl-6H-thieno[3,2-f][1,2,4]triazolo[4,3-a][1,4]diazepin-6-yl)acetic acid (10 mg, 0.025 mmol) in 1 mL DMSO were added HATU (11 mg, 0.03 mmol) and DIEA (12 μL, 0.075 mmol), the mixture was stirred at room temperature for 30 min and then purified by prep-HPLC (MeOH/H$_2$O, 0.05% TFA) to obtain 8 (10.9 mg, 47%).

$^1$H NMR (500 MHz, DMSO-d$_6$) δ 11.01 (s, 1H), 8.35 (d, J=8.0 Hz, 1H), 8.20 (s, 1H), 8.11 (s, 1H), 7.98 (s, 1H), 7.82 (q, J=8.5, 6.4 Hz, 1H), 7.47 (d, J=8.3 Hz, 2H), 7.42 (d, J=8.2 Hz, 2H), 5.87-5.80 (m, 1H), 4.52 (dd, J=8.3, 5.7 Hz, 1H), 4.22 (d, J=6.4 Hz, 2H), 3.20 (tt, J=33.0, 12.2 Hz, 5H), 3.00-2.88 (m, 1H), 2.59 (s, 5H), 2.38 (s, 3H), 2.09-2.02 (m, 1H), 1.82 (q, J=6.9 Hz, 2H), 1.60 (d, J=4.3 Hz, 3H), 1.51 (d, J=10.1 Hz, 4H), 1.42 (dd, J=9.5, 5.3 Hz, 2H).

LCMS (m/z): 806 [M+H]$^+$.

Example 8: 2-((S)-4-(4-chlorophenyl)-2,3,9-trimethyl-6H-thieno[3,2-f][1,2,4]triazolo[4,3-a][1,4]diazepin-6-yl)-N-(8-(2-(2,6-dioxopiperidin-3-yl)-1,3-dioxo-2,3-dihydro-1H-benzo[de]isoquinolin-4-ylamino)octyl)acetamide (5)

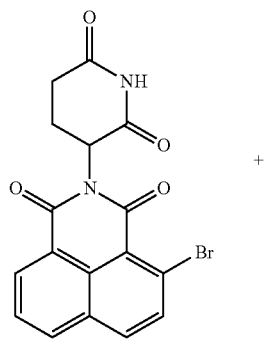

+

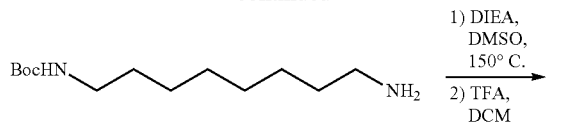

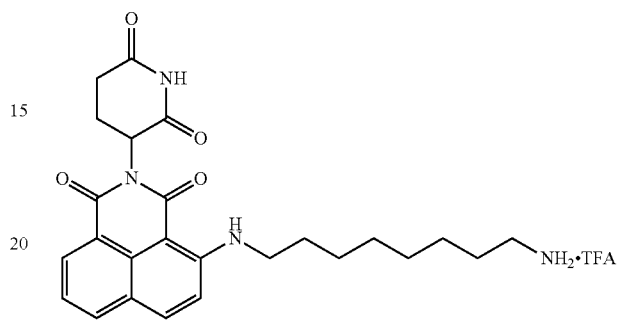

To the solution of 4-bromo-2-(2,6-dioxopiperidin-3-yl)-1H-benzo[de]isoquinoline-1,3(2H)-dione (100 mg, 0.26 mmol) and tert-butyl 8-aminooctylcarbamate (63 mg, 0.26 mmol) in DMSO (1.5 mL), DIEA (67 mg, 0.52 mmol) was added at room temperature. Then the reaction mixture was heated up to 150° C. for 1 hour. After the reaction mixture was cooled down, added DCM (1 mL) and TFA (0.5 mL) at room temperature. After 1 hour, the reaction mixture was purified with HPLC to yield 4-(8-aminooctylamino)-2-(2,6-dioxopiperidin-3-yl)-1H-benzo[de]isoquinoline-1,3(2H)-dione (78.3 mg, 0.14 mmol, 55%) as a TFA salt.

LC/MS m/z calculated for [M+H]$^+$ 451.2, found 451.2.

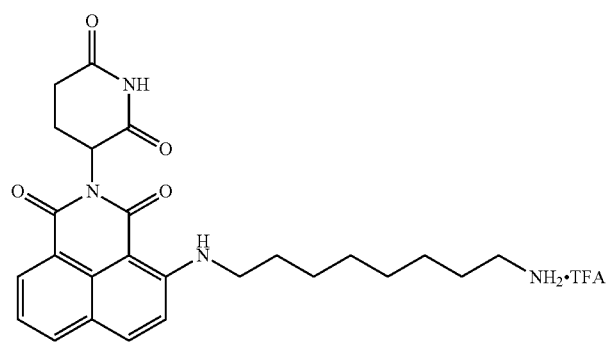

+

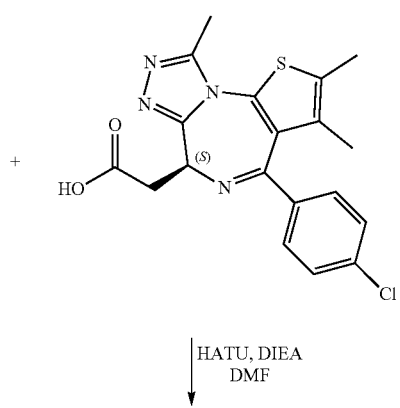

HATU, DIEA
DMF

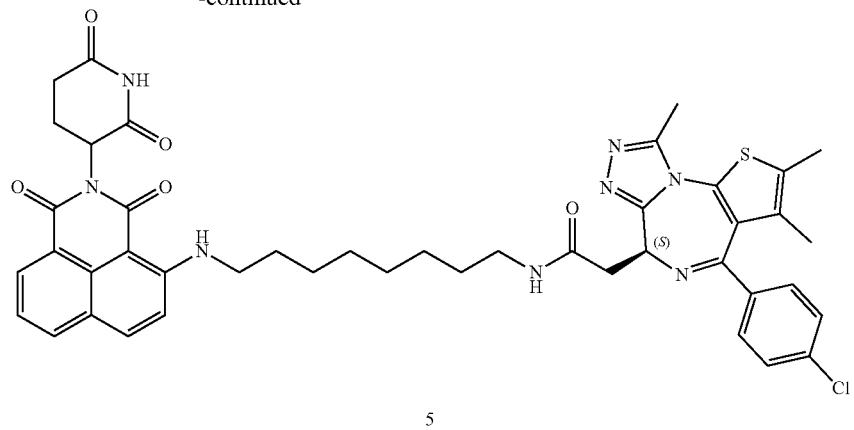

To the solution of 4-(8-aminooctylamino)-2-(2,6-dioxopiperidin-3-yl)-1H-benzo[de]isoquinoline-1,3(2H)-dione TFA salt (28.2 mg, 0.050 mmol) and (S)-2-(4-(4-chlorophenyl)-2,3,9-trimethyl-6H-thieno[3,2-f][1,2,4]triazolo[4,3-a][1,4]diazepin-6-yl)acetic acid (20 mg, 0.050 mmol) in DMF (1 mL), HATU (38 mg, 0.10 mmol) and DIEA (32 mg, 0.25 mmol) were added under ice bath, then warmed up to room temperature. After 10 mins, the mixture was purified with HPLC to yield 2-((S)-4-(4-chlorophenyl)-2,3,9-trimethyl-6H-thieno[3,2-f][1,2,4]triazolo[4,3-a][1,4]diazepin-6-yl)-N-(8-(2-(2,6-dioxopiperidin-3-yl)-1,3-dioxo-2,3-dihydro-1H-benzo[de]isoquinolin-4-ylamino)octyl)acetamide (5) (37 mg, 0.044 mmol, 89%).

LC/MS m/z calculated for [M+H]$^+$ 833.3, found 833.3.

Example 9: 2-((S)-4-(4-chlorophenyl)-2,3,9-trimethyl-6H-thieno[3,2-f][1,2,4]triazolo[4,3-a][1,4]diazepin-6-yl)-N-(5-(2-(2,6-dioxopiperidin-3-yl)-1,3-dioxo-2,3-dihydro-1H-benzo[de]isoquinolin-5-yloxy)pentyl)acetamide (4)

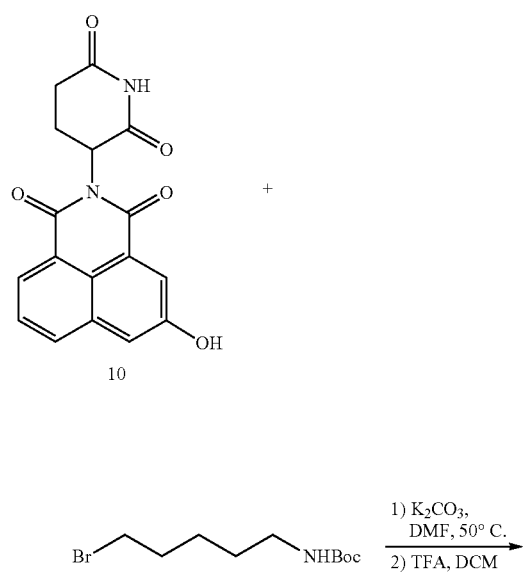

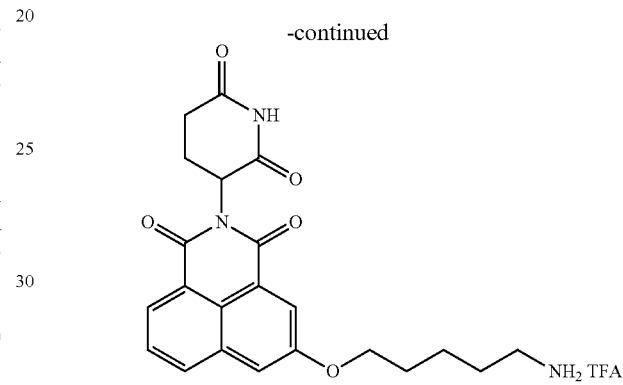

To the solution of 10 (100 mg, 0.31 mmol) and tert-butyl 5-bromopentylcarbamate (82 mg, 0.31 mmol) in DMF (2 mL), K$_2$CO$_3$ (128 mg, 0.93 mmol) was added at room temperature. Then the mixture was heated up to 50° C. overnight. After the mixture was cooled down, it was filtered and the filtrate was concentrated under vacuum. The residue was dissolved in DCM (1 mL), then TFA (0.5 mL) was added at room temperature. After 1 hour, the reaction was evaporated under vacuum and the residue was purified with HPLC to yield 5-(5-aminopentyloxy)-2-(2,6-dioxopiperidin-3-yl)-1H-benzo[de]isoquinoline-1,3(2H)-dione (81 mg, 0.16 mmol, 52%) as TFA salt.

LC/MS m/z calculated for [M+H]$^+$ 410.2, found 410.2.

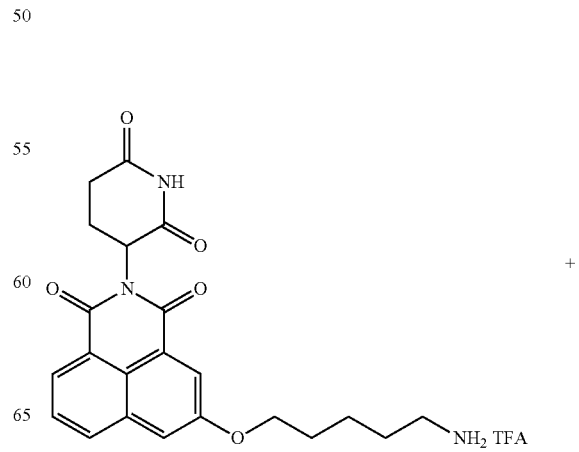

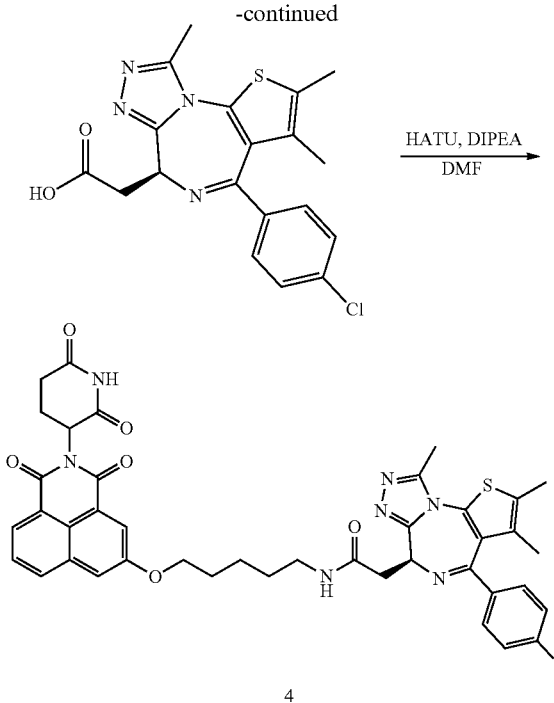

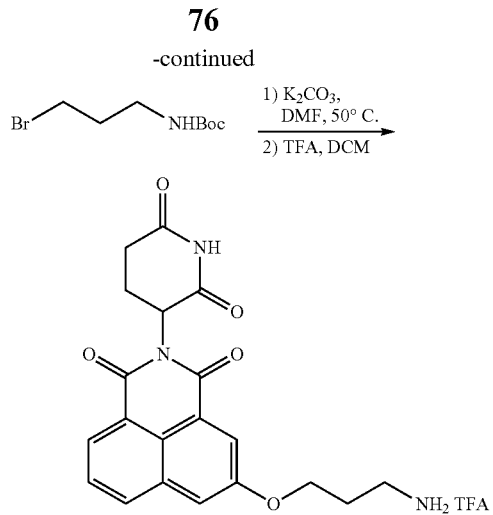

To the solution of 5-(5-aminopentyloxy)-2-(2,6-dioxopiperidin-3-yl)-1H-benzo[de]isoquinoline-1,3(2H)-dione (26 mg, 0.05 mmol) and (S)-2-(4-(4-chlorophenyl)-2,3,9-trimethyl-6H-thieno[3,2-f][1,2,4]triazolo[4,3-a][1,4]diazepin-6-yl)acetic acid (20 mg, 0.050 mmol) in DMF (1 mL), HATU (38 mg, 0.10 mmol) and DIEA (32 mg, 0.25 mmol) were added under ice bath, then warmed up to room temperature. After 10 mins, the mixture was purified with HPLC to yield 2-((S)-4-(4-chlorophenyl)-2,3,9-trimethyl-6H-thieno[3,2-f][1,2,4]triazolo[4,3-a][1,4]diazepin-6-yl)-N-(5-(2-(2,6-dioxopiperidin-3-yl)-1,3-dioxo-2,3-dihydro-1H-benzo[de]isoquinolin-5-yloxy)pentyl)acetamide (4) (34 mg, 0.0435 mmol, 87%).

LC/MS m/z calculated for [M+H]$^+$ 792.2, found 792.2.

Example 10: 2-((S)-4-(4-chlorophenyl)-2,3,9-trimethyl-6H-thieno[3,2-f][1,2,4]triazolo[4,3-a][1,4]diazepin-6-yl)-N-(3-(2-(2,6-dioxopiperidin-3-yl)-1,3-dioxo-2,3-dihydro-1H-benzo[de]isoquinolin-5-yloxy)propyl)acetamide (3)

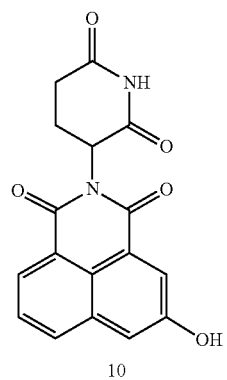

To the solution of 10 (100 mg, 0.31 mmol) and tert-butyl 3-bromopropylcarbamate (74 mg, 0.31 mmol) in DMF (2 mL), K$_2$CO$_3$ (128 mg, 0.93 mmol) was added at room temperature. Then the mixture was heated up to 50° C. overnight. After the mixture was cooled down, it was filtered and the filtrate was concentrated under vacuum. The residue was dissolved in DCM (1 mL), then TFA (0.5 mL) was added at room temperature. After 1 hour, the reaction was evaporated under vacuum and the residue was purified with HPLC to yield 5-(3-aminopropoxy)-2-(2,6-dioxopiperidin-3-yl)-1H-benzo[de]isoquinoline-1,3(2H)-dione (144 mg, 0.30 mmol, 97%) as TFA salt.

LC/MS m/z calculated for [M+H]$^+$ 382.1, found 382.1.

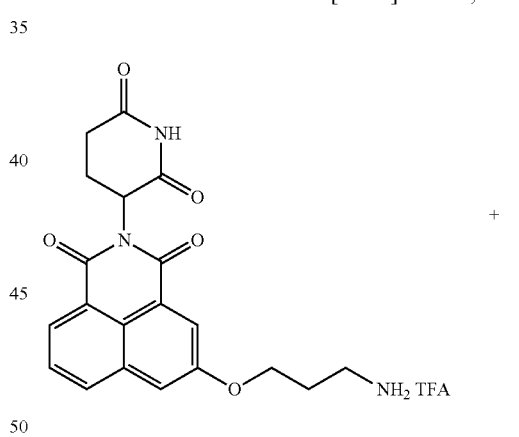

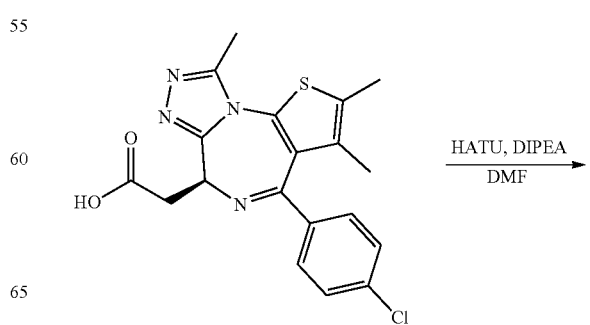

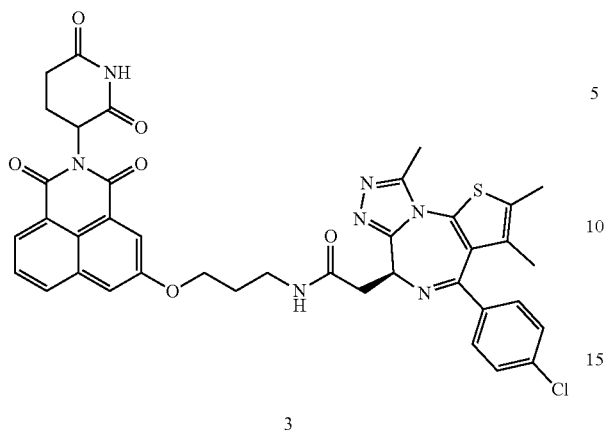

3

To a solution of 5-(3-aminopropoxy)-2-(2,6-dioxopiperidin-3-yl)-1H-benzo[de]isoquinoline-1,3(2H)-dione (18.6 mg, 0.0375 mmol) and (S)-2-(4-(4-chlorophenyl)-2,3,9-trimethyl-6H-thieno[3,2-f][1,2,4]triazolo[4,3-a][1,4]diazepin-6-yl)acetic acid (15 mg, 0.0375 mmol) in DMF (1 mL), HATU (28 mg, 0.075 mmol) and DIEA (24 mg, 0.19 mmol) were added under ice bath, then warmed up to room temperature. After 10 mins, the mixture was purified with HPLC to yield 2-((S)-4-(4-chlorophenyl)-2,3,9-trimethyl-6H-thieno[3,2-f][1,2,4]triazolo[4,3-a][1,4]diazepin-6-yl)-N-(3-(2-(2,6-dioxopiperidin-3-yl)-1,3-dioxo-2,3-dihydro-1H-benzo[de]isoquinolin-5-yloxy)propyl)acetamide (3) (23 mg, 0.030 mmol, 81%).

LC/MS m/z calculated for [M+H]$^+$ 764.2, found 764.2.

Example 11: 2-((S)-4-(4-chlorophenyl)-2,3,9-trimethyl-6H-thieno[3,2-f][1,2,4]triazolo [4,3-a][1,4] diazepin-6-yl)-N-(8-(2-(2-(2,6-dioxopiperidin-3-yl)-1,3-dioxo-2,3-dihydro-1H-benzo[de]isoquinolin-5-yloxy)acetamido)octyl)acetamide (2)

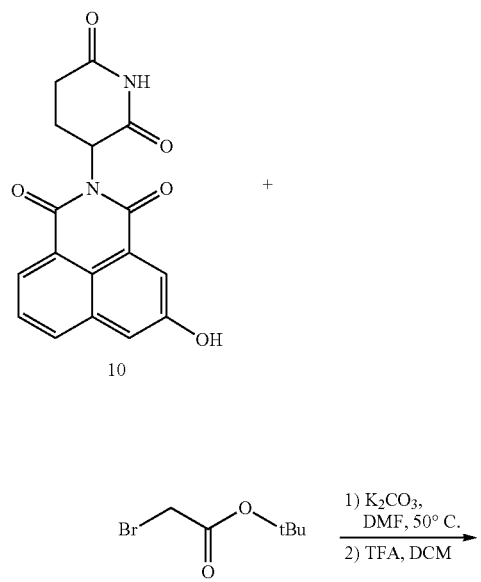

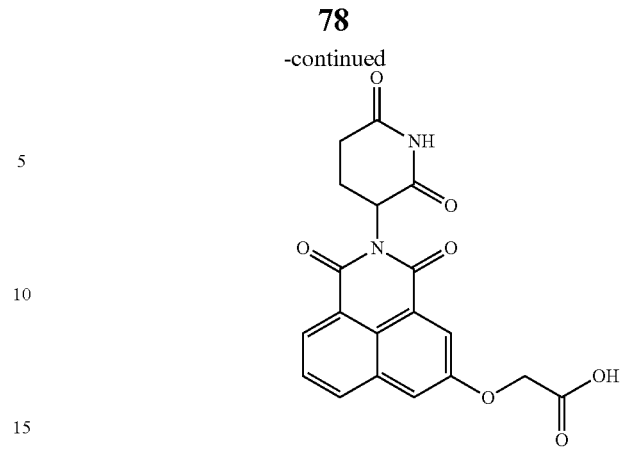

To a solution of 10 (100 mg, 0.31 mmol) and tert-butyl 2-bromoacetate (60 mg, 0.31 mmol) in DMF (2 mL), K$_2$CO$_3$ (128 mg, 0.93 mmol) was added at room temperature. Then the mixture was heated up to 50° C. overnight. After the mixture was cooled down, it was filtered and the filtrate was concentrated under vacuum. The residue was dissolved in DCM (1 mL), then TFA (0.5 mL) was added at room temperature. After 1 hour, the reaction was evaporated under vacuum and the residue was purified with HPLC to yield 2-(2-(2,6-dioxopiperidin-3-yl)-1,3-dioxo-2,3-dihydro-1H-benzo[de]isoquinolin-5-yloxy)acetic acid (81 mg, 0.21 mmol, 68%).

LC/MS m/z calculated for [M+H]$^+$ 383.1, found 383.1.

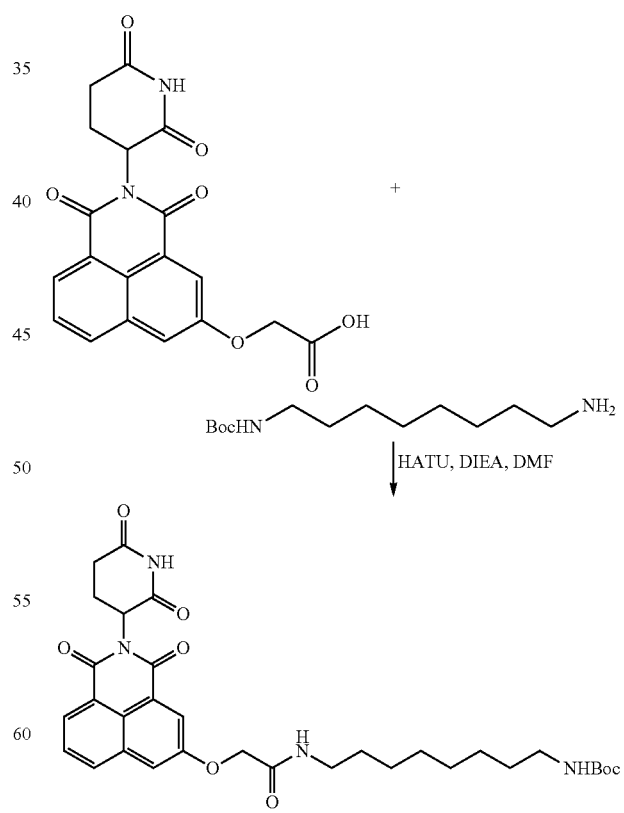

To a solution of 2-(2-(2,6-dioxopiperidin-3-yl)-1,3-dioxo-2,3-dihydro-1H-benzo[de]isoquinolin-5-yloxy)acetic acid (80 mg, 0.21 mmol) and tert-butyl 8-aminooctylcarbamate (51 mg, 0.21 mmol) in DMF (1 mL), DIEA (136 mg, 1.05 mmol) and HATU (160 mg, 0.42 mmol) were added at room temperature. After 10 mins, the reaction mixture was quenched with water, extracted with EtOAc (5 mL*3). The organic layer was concentrated under vacuum. The resulted residue was purified with flash chromatography to yield tert-butyl 8-(2-(2-(2,6-dioxopiperidin-3-yl)-1,3-dioxo-2,3-dihydro-1H-benzo[de]isoquinolin-5-yloxy)acetamido)octylcarbamate (109 mg, 0.18 mmol, 88%).

LC/MS m/z calculated for [M+H]½609.3, found 609.3.

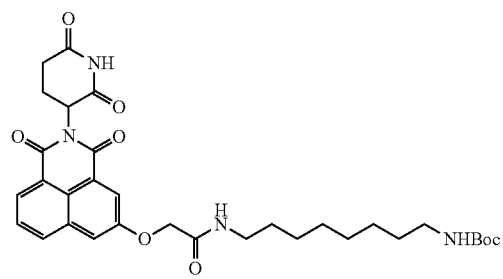

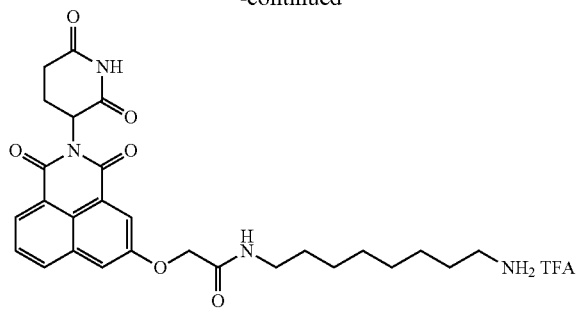

To a solution of tert-butyl 8-(2-(2-(2,6-dioxopiperidin-3-yl)-1,3-dioxo-2,3-dihydro-1H-benzo[de]isoquinolin-5-yloxy)acetamido)octylcarbamate (109 mg, 0.18 mmol) in DCM (2 mL), TFA (1 mL) was added at room temperature. After 1 hour, the mixture was evaporated under vacuum to yield the crude product N-(8-aminooctyl)-2-(2-(2,6-dioxopiperidin-3-yl)-1,3-dioxo-2,3-dihydro-1H-benzo[de]isoquinolin-5-yloxy)acetamide as a TFA salt.

LC/MS m/z calculated for [M+H]⁺ 509.2, found 509.2.

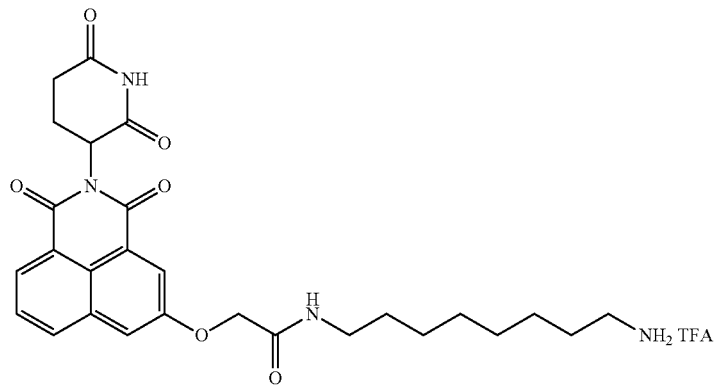

+

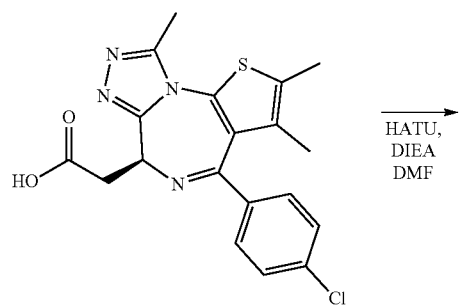

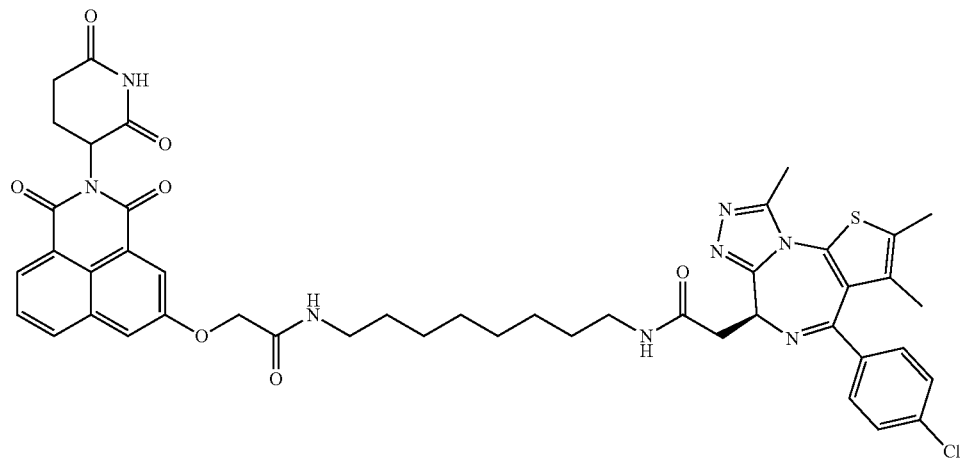

2

To a solution of N-(8-aminooctyl)-2-(2-(2,6-dioxopiperidin-3-yl)-1,3-dioxo-2,3-dihydro-1H-benzo[de]isoquinolin-5-yloxy)acetamide TFA salt (10 mg, 0.016 mmol) and (S)-2-(4-(4-chlorophenyl)-2,3,9-trimethyl-6H-thieno[3,2-f][1,2,4]triazolo[4,3-a][1,4]diazepin-6-yl)acetic acid (6.4 mg, 0.016 mmol) in DMF (1 mL), HATU (12 mg, 0.032 mmol) and DIEA (10 mg, 0.08 mmol) were added under ice bath, then warmed up to room temperature. After 10 mins, the mixture was purified with HPLC to yield 2-((S)-4-(4-chlorophenyl)-2,3,9-trimethyl-6H-thieno[3,2-f][1,2,4]triazolo[4,3-a][1,4]diazepin-6-yl)-N-(8-(2-(2-(2,6-dioxopiperidin-3-yl)-1,3-dioxo-2,3-dihydro-1H-benzo[de]isoquinolin-5-yloxy)acetamido)octyl)acetamide (2) (9 mg, 0.010 mmol, 63%).

LC/MS m/z calculated for [M+H]$^+$ 891.3, found 891.3.

Example 12: Cellular Degradation Assays

IKZF1 (construct IKZF1$^{\Delta1-82/\Delta197-238/\Delta256-519}$) BRD2BD1, BRD2BD2, BRD3BD1, BRD3BD2, BRD4BD1, and BRD4BD2 were subcloned into mammalian pcDNA5/FRT Vector (Ampicillin and Hygromycin B resistant) modified to contain MCS-eGFP-P2A-mCherry. Stable cell lines expressing eGFP-protein fusion and mCherry reporter were generated using Flip-In 293 system. Plasmid (0.3 μg) and pOG44 (4.7 μg) DNA were preincubated in 100 μL of Opti-MEM I (Gibco™ Life Technologies™) media containing 0.05 mg/ml Lipofectamine 2000 (Invitrogen™) for 20 min and added to Flip-In 293 cells containing 1.9 ml of DMEM media (Gibco™, Life Technologies™) per well in a 6-well plate format (Falcon®, 353046). Cells were propagated after 48 h and transferred into a 10 cm$^2$ plate (Corning, 430165) in DMEM media containing 50 μg/ml of Hygromycin B (REF 10687010, Invitrogen™) as a selection marker. Following 2-3 passage cycle FACS (FACSAria™ II, BD) was used to enrich for cells expressing eGFP and mCherry. Cells were seeded at 30-50% confluency in either 24, 48 or 96 well plates (3524, 3548, 3596 respectively, Costar®) a day before compound treatment. Titrated compounds were incubated with cells for 5 h following trypsinisation and resuspension in DMEM media, transferred into 96-well plates (353910, Falcon®) and analyzed by flow cytometer (Guava© easyCyte HT, Millipore™) Signal from 5000 cells per well was acquired in singlicate or duplicate and the eGFP and mCherry florescence monitored. Data was analyzed using FlowJo® (FlowJo®, LCC). Forward and side scatter outliers, frequently associated with cell debris, were removed leaving >90% of total cells, followed by removal of eGFP and mCherry signal outliers, leaving 88-90% of total cells creating the set used for quantification. The eGFP protein abundance relative to mCherry was then quantified as a ten-fold amplified ratio for each individual cell using the formula: 10×eGFP/mCherry. The median of the ratio was then calculated per set, normalized to the median of the DMSO ratio, and is denoted as relative abundance.

Figure 1B:
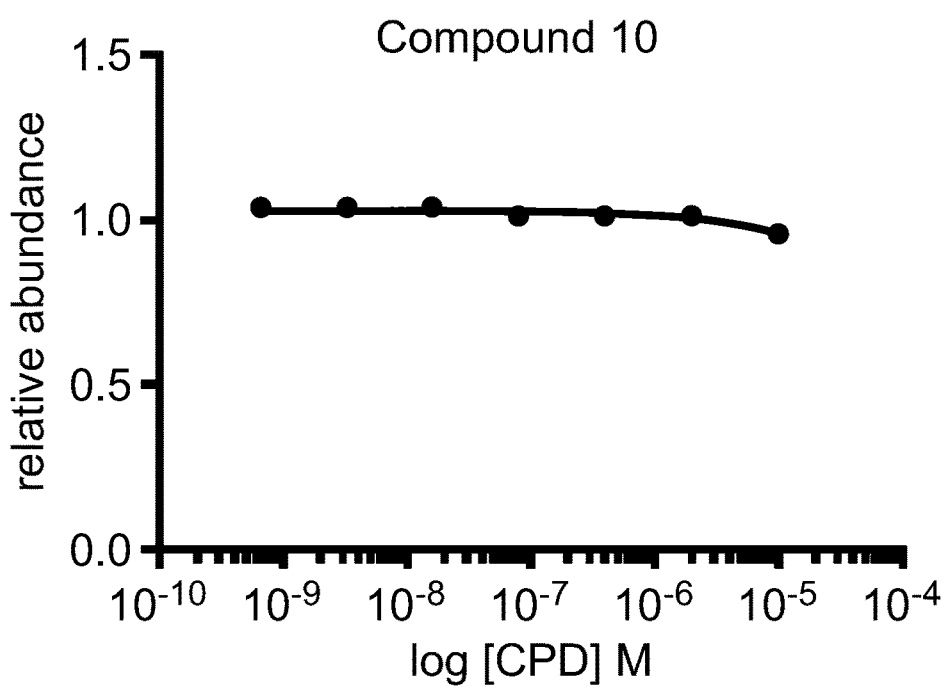
Figure 1C:
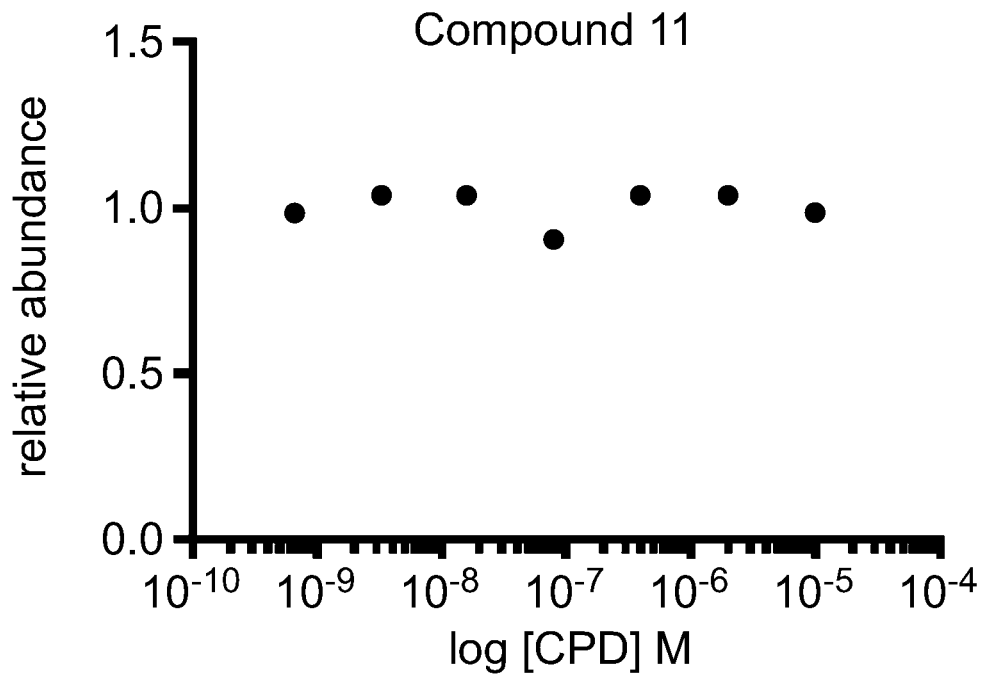
Figure 1D:
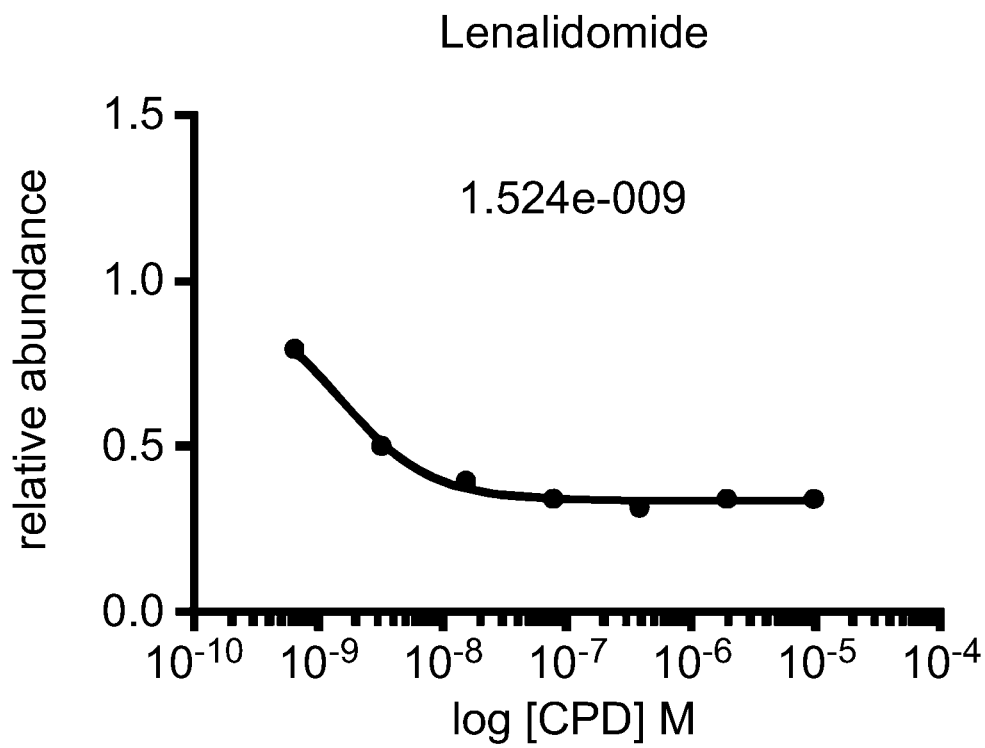
Figure 2A:
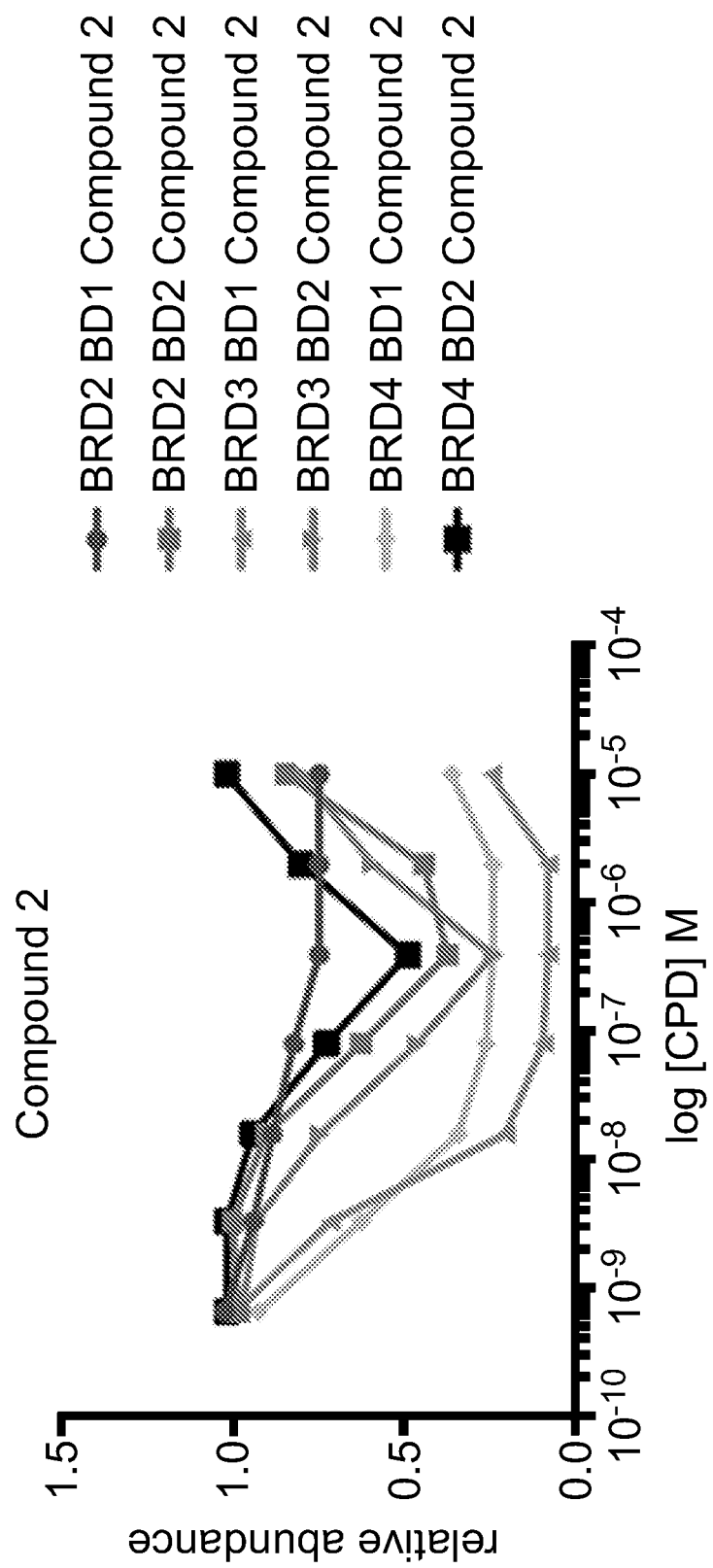
FIG. 2A-FIG. 2C shows degradation of subunits BD1 and BD2 of BRD2, BRD3, and BRD4 by inventive bifunctional compounds 1 and 2 and known control dBET6.
Figure 2B:
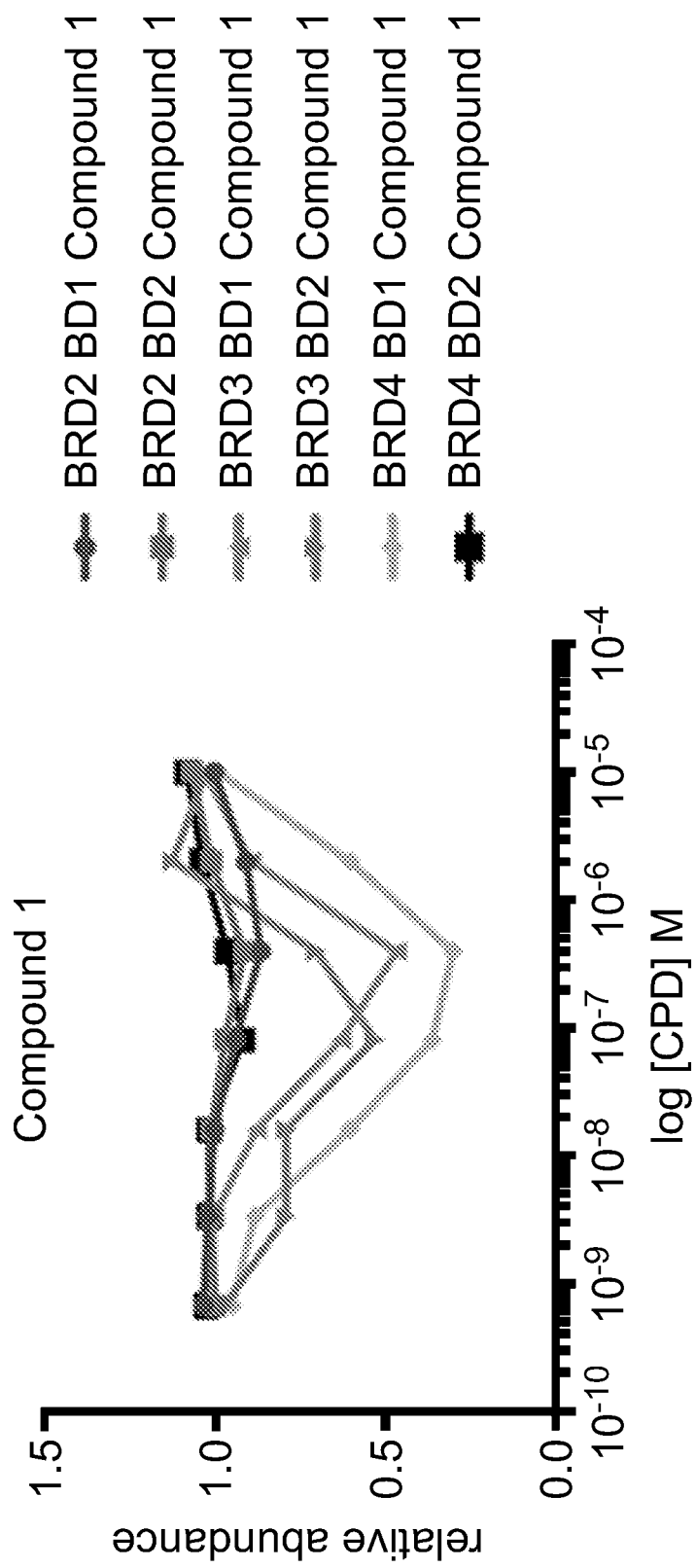
Figure 2C:
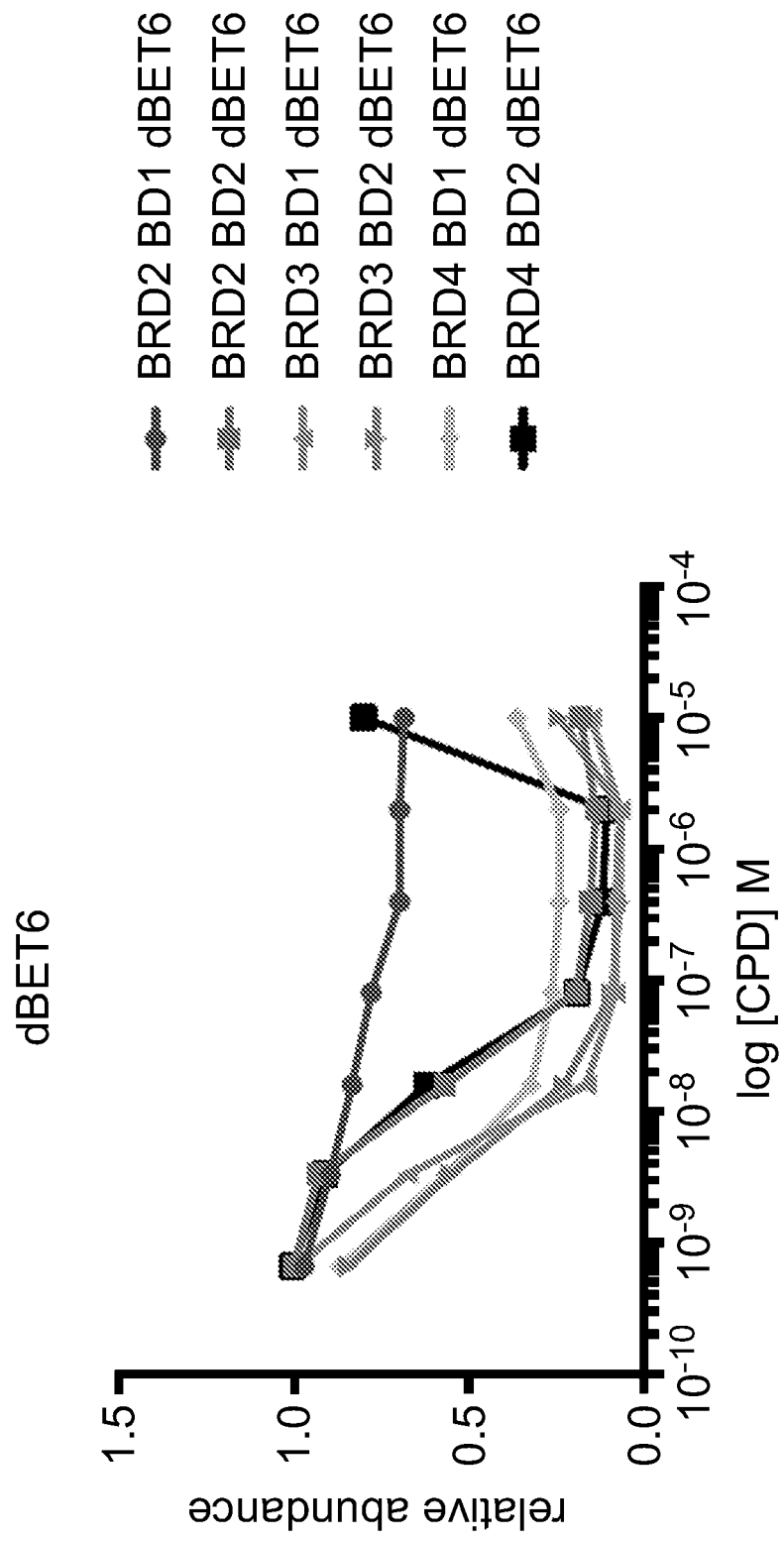
Figure 3A:
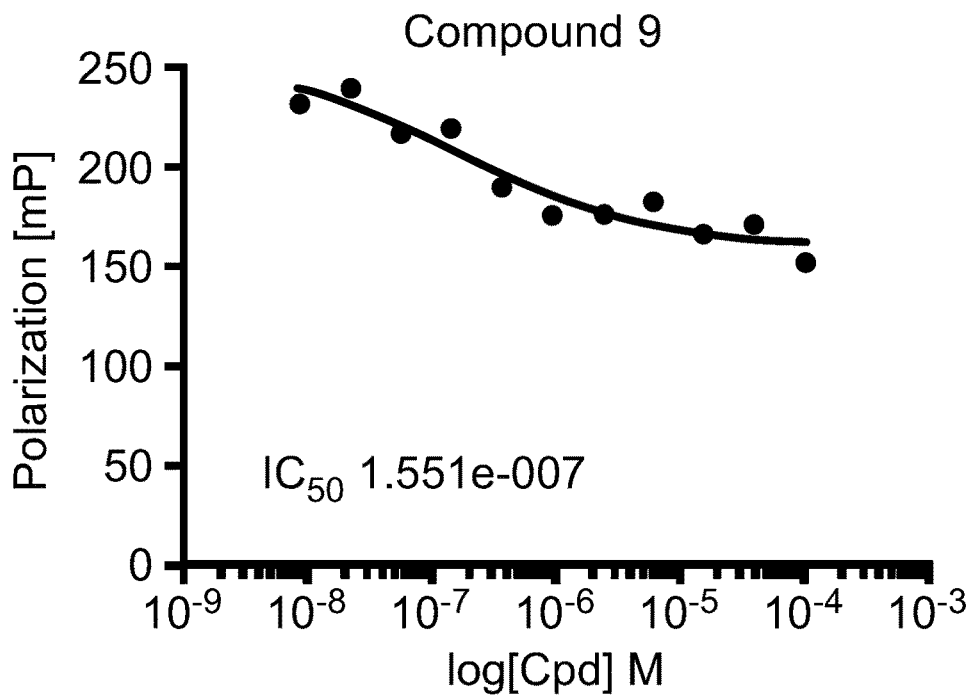
FIG. 3A-FIG. 3D are graphs that show CRBN binding in an FP displacement assay by thalidomide analogs 9, 10 and 11 and FDA-approved lenalidomide.
Figure 3B:
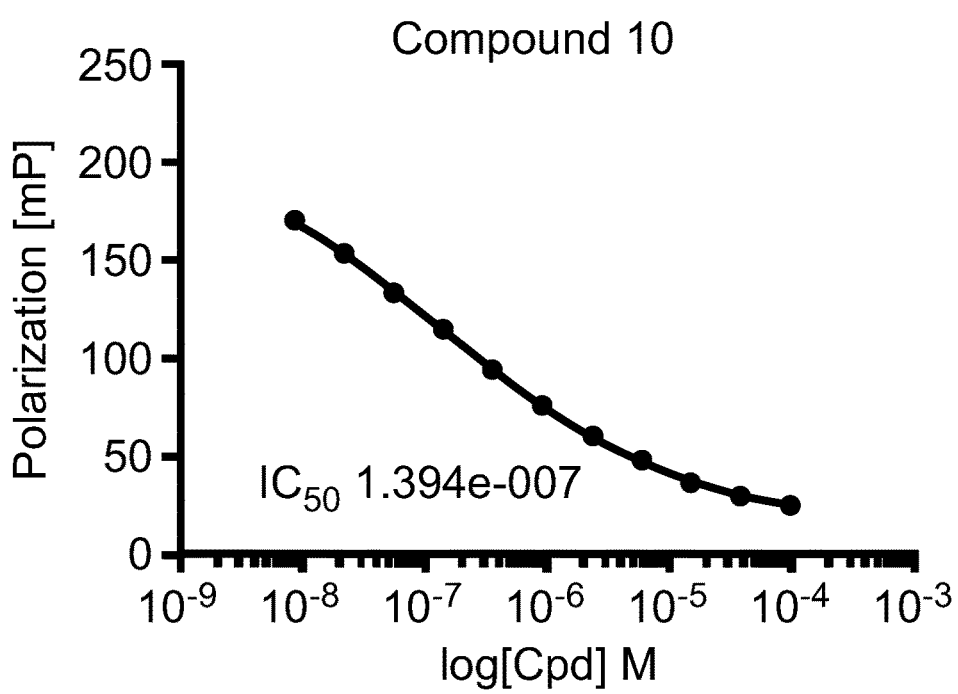
Figure 3C:
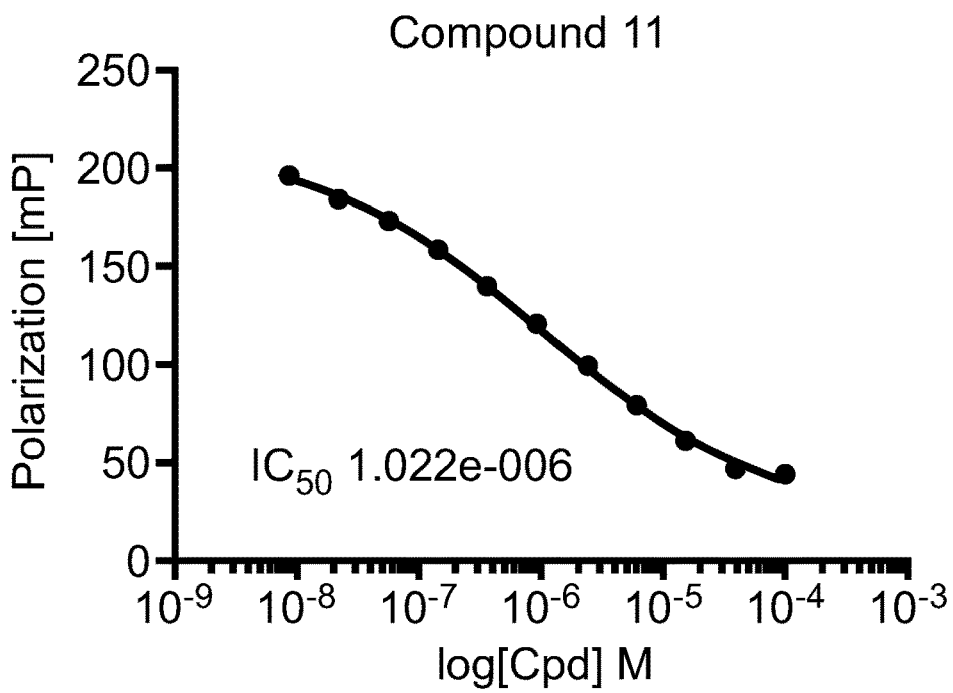
Figure 3D:
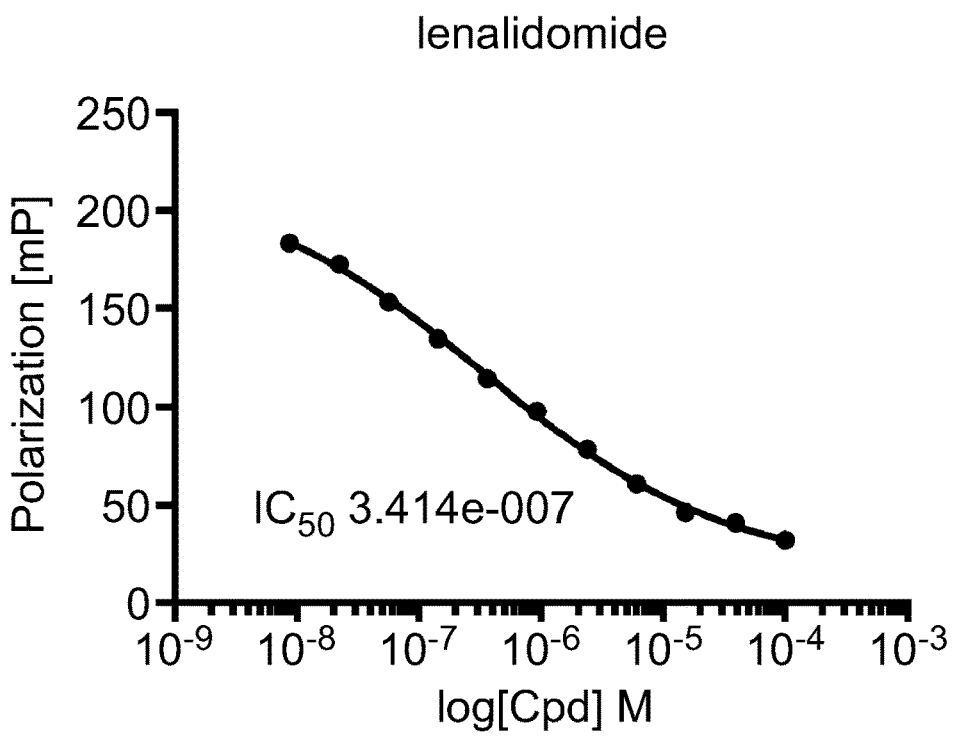

The results are shown in FIG. 1A-FIG. 1D and FIG. 2A-FIG. 2C. FIG. 1A-FIG. 1C show that compounds 9, 10, and 11, which are non-inventive thalidomide analogs, were inactive against the target IKZF1, as compared to FDA-approved lenalidomide (DC$_{50}$=1.524e-009) (shown in FIG. 1D). In sharp contrast, FIG. 2A-FIG. 2C show that inventive bifunctional compound 2 was active against BRD2 (via BRD2BD2), BRD3 (via BRD3BD1 and BRD3BD2) and BRD4 (via BRD4BD1 and BRD4BD2), while inventive compound 1 was active against BRD3 (via BRD3BD1 and BRD3BD2) and BRD4 (via BRD4BD1) and inactive against BRD2, indicating that bromodomain selectivity can be achieved with these scaffolds. The known compound "dBET6" was used as a control.

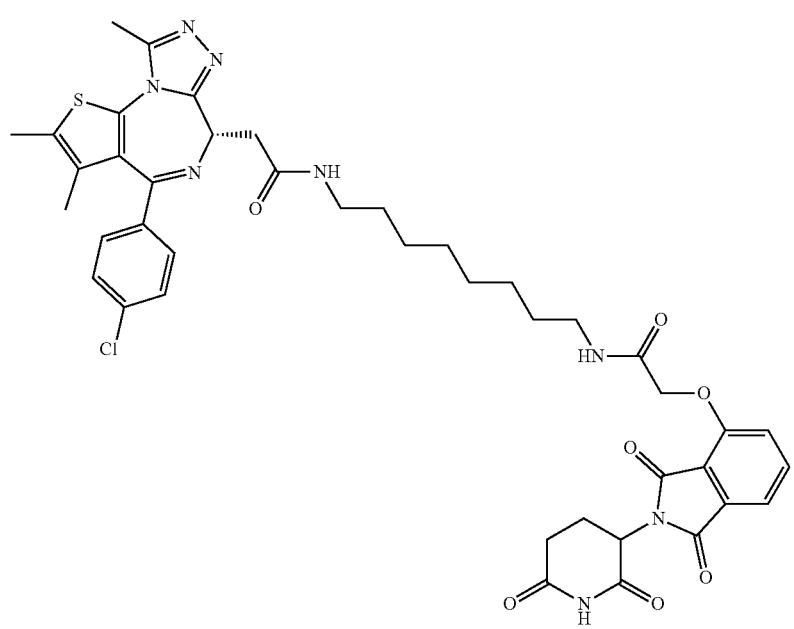

(dBET6)

Example 13: Lenalidomide Assay

Compounds in Atto565-Lenalidomide displacement assay were dispensed in a 384-well microplate (Corning, 4514) using D300e Digital Dispenser (HP) normalized to 1% DMSO into 10 nM Atto565-Leanlidomide, 100 nM DDB1ΔB-CRBN, 50 mM Tris pH 7.5, 200 mM NaCl, 0.1% Pluronic® F-68 solution (Sigma). Compound titrations were incubated for 60 min at RT. The change in fluorescence polarization was monitored using a PHERAstar® FS microplate reader (BMG Labtech) for 1 h in 120 s cycles. Data from three independent replicates (n=3) was used to estimate $IC_{50}$ values using variable slope equation in GraphPad Prism 7.

The results are shown in FIG. 3A-FIG. 3D. Compounds 9, 10, and 11 are potent binders of CRBN with $IC_{50}$ comparable to FDA approved lenalidomide, while being inactive in degradation of IKZF1 [FIG. 1A-FIG. 1-D].

TABLE 1

| | CRBN Binding | | | |
|---|---|---|---|---|
| Compound | Structure | CRBN Binding ($IC_{50}$ μM) | CRBN Binding (Ki μM) | MM1.S Cell Proliferation ($IC_{50}$ μM) |
| 9 | | 2.6 | 0.7 | ~21.53 |
| 10 | | 3.5 | 0.98 | — |
| 11 | | 11.4 | 3.2 | — |

Example 14: Analysis of Change to Cellular Protein Abundance in Response to Treatment with Compounds 1 and 2

Kelly cells were treated with DMSO control (biological triplicates) or 1 µM of inventive compound 1 or compound 2 for 6 hours (biological singlicate). Lysis buffer (8 M Urea, 50 mM NaCl, 50 mM 4-(2hydroxyethyl)-1-piperazineethanesulfonic acid (EPPS) pH 8.5, Protease and Phosphatase inhibitors from Roche) was added to the cell pellets and homogenized by 20 passes through a 21 gauge (1.25 in. long) needle to achieve a cell lysate with a protein concentration between 1-4 mg mL$^{-1}$. A Micro BCA™ assay (Pierce™) was used to determine the final protein concentration in the cell lysate. 200 µg of protein for each sample were reduced and alkylated as previously described.

Proteins were precipitated using methanol/chloroform/water (4:1:3). In brief, four volumes of methanol were added to the cell lysate, followed by one volume of chloroform, and finally three volumes of water. The mixture was vortexed and centrifuged to separate the chloroform phase from the aqueous phase. The precipitated protein was washed with three volumes of methanol, centrifuged and the resulting washed precipitated protein was allowed to air dry. Precipitated protein was resuspended in 4 M Urea, 50 mM 4-(2-hydroxyethyl)-1-piperazineethanesulfonic acid (HEPES) pH 7.4, followed by dilution to 1 M urea with the addition of 200 mM EPPS, pH 8. Proteins were first digested with LysC (1:50; enzyme:protein) for 12 hours at room temperature. The LysC digestion was diluted to 0.5 M Urea with 200 mM EPPS pH 8 followed by digestion with trypsin (1:50; enzyme:protein) for 6 hours at 37° C. Tandem mass tag (TMT) reagents (Thermo Fisher Scientific) were dissolved in anhydrous acetonitrile (ACN) according to manufacturer's instructions. Anhydrous ACN was added to each peptide sample to a final concentration of 30% v/v, and labeling was induced with the addition of TMT reagent to each sample at a ratio of 1:4 peptide:TMT label. The 10-plex labeling reactions were performed for 1.5 hours at room temperature and the reaction quenched by the addition of hydroxylamine to a final concentration of 0.3% for 15 minutes at room temperature. The sample channels were combined at a 1:1:1:1:1:1:1:1:1:1 ratio, desalted using C$_{18}$ solid phase extraction cartridges (Waters) and analyzed by LC-MS for channel ratio comparison. Samples were then combined using the adjusted volumes determined in the channel ratio analysis and dried down in a speed vacuum. The combined sample was then resuspended in 1% formic acid, and acidified (pH 2-3) before being subjected to desalting with C18 SPE (Sep-Pak®, Waters). Samples were then offline fractionated into 96 fractions by high pH reverse-phase HPLC (Agilent LC1260) through an aeris peptide xb-c18 column (phenomenex) with mobile phase A containing 5% acetonitrile and 10 mM NH$_4$HCO$_3$ in LC-MS grade H$_2$O, and mobile phase B containing 90% acetonitrile and 10 mM NH$_4$HCO$_3$ in LC-MS grade H$_2$O (both pH 8.0). The 96 resulting fractions were then pooled in a non-continuous manner into 24 fractions and these fractions were used for subsequent mass spectrometry analysis.

Data were collected using an Orbitrap Fusion™ Lumos™ mass spectrometer (Thermo Fisher Scientific, San Jose, CA, USA) coupled with a Proxeon EASY-nLC™ 1200 LC pump (Thermo Fisher Scientific). Peptides were separated on a 75 µM inner diameter microcapillary column packed with ~50 cm of Accucore™ C18 resin (1.8 µM, 100 Å, Thermo Fisher Scientific). Peptides were separated using a 190 min gradient of 6-27% acetonitrile in 1.0% formic acid with a flow rate of 400 nL/min. Each analysis used an MS3-based TMT method as described previously. The data were acquired using a mass range of m z 340-1350, resolution 120,000, automatic gain control (AGC) target 5×10$^5$, maximum injection time 100 ms, dynamic exclusion of 70 seconds for the peptide measurements in the Orbitrap™. Data dependent MS2 spectra were acquired in the ion trap with a normalized collision energy (NCE) set at 35%, AGC target set to 1.8×10$^4$ and a maximum injection time of 120 ms. MS3 scans were acquired in the Orbitrap™ with a higher-energy collisional dissociation (HCD) collision energy set to 55%, AGC target set to 2×10$^5$, maximum injection time of 150 ms, resolution at 50,000 and with a maximum synchronous precursor selection (SPS) precursors set to 10.

Proteome Discoverer™ 2.2 (Thermo Fisher Scientific) was used for RAW file processing and controlling peptide and protein level false discovery rates, assembling proteins from peptides, and protein quantification from peptides. MS/MS spectra were searched against a Uniprot human database (September 2016) with both the forward and reverse sequences. Database search criteria are as follows: tryptic with two missed cleavages, a precursor mass tolerance of 10 ppm, fragment ion mass tolerance of 0.6 Da, static alkylation of cysteine (57.02146 Da), static TMT labelling of lysine residues and N-termini of peptides (229.16293 Da), variable phosphorylation of serine, threonine and tyrosine (79.996 Da), deamidation of asparagine and glutamine (0.984) and variable oxidation of methionine (15.99491 Da). TMT reporter ion intensities were measured using a 0.003 Da window around the theoretical m z for each reporter ion in the MS3 scan. Peptide spectral matches with poor quality MS3 spectra were excluded from quantitation (summed signal-to-noise across 10 channels <200 and precursor isolation specificity <0.5), and resulting data was filtered to include only proteins that had a minimum of 3 unique peptides identified. Reporter ion intensities were normalised and scaled using in-house scripts in the R framework. Statistical analysis was carried out using the LIMMA package within the R framework.

Figure 4A:
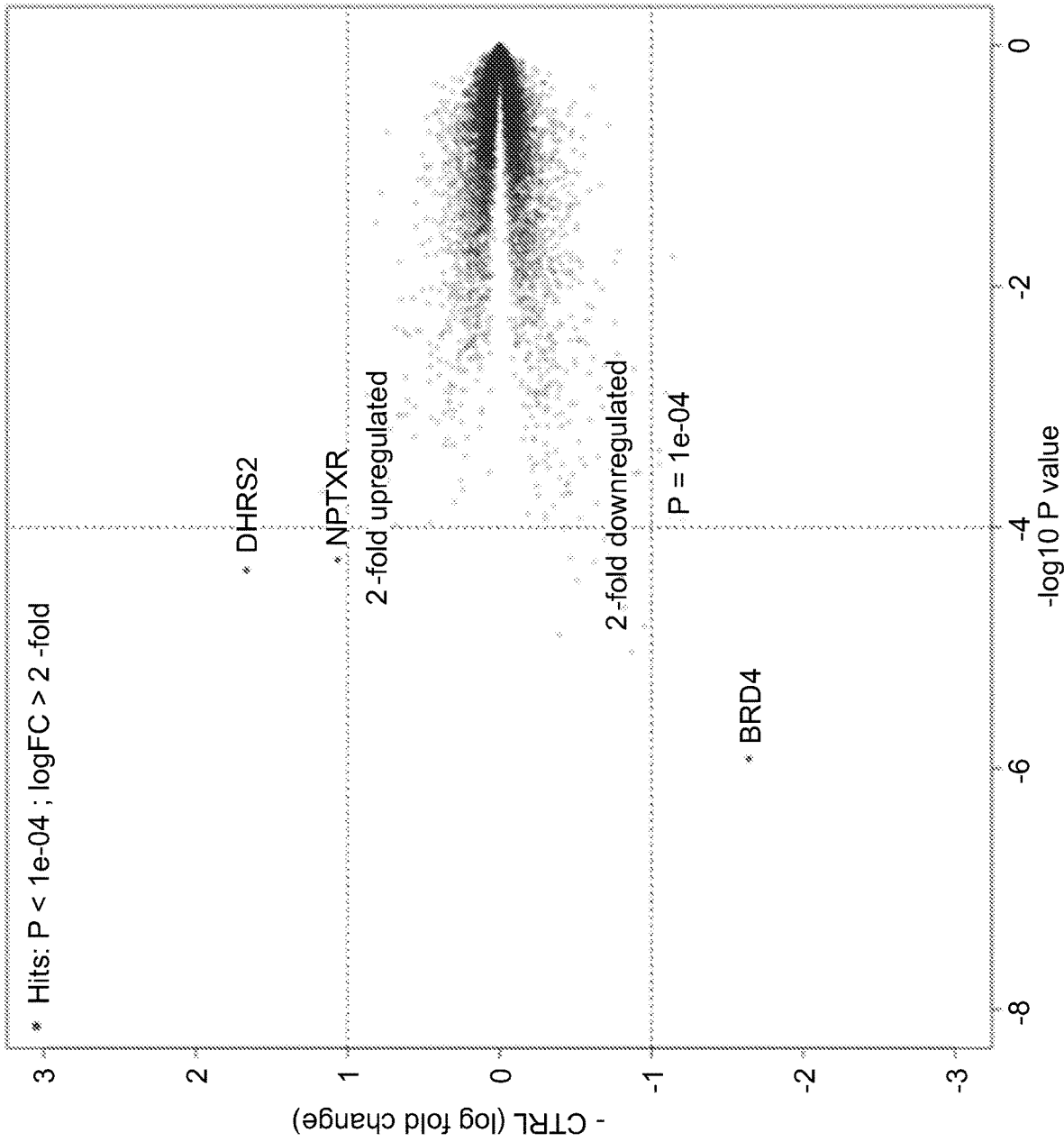
FIG. 4A-FIG. 4B are plots that show the change in relative protein abundance with treatment of inventive bifunctional compounds 1 and 2.
Figure 4B:
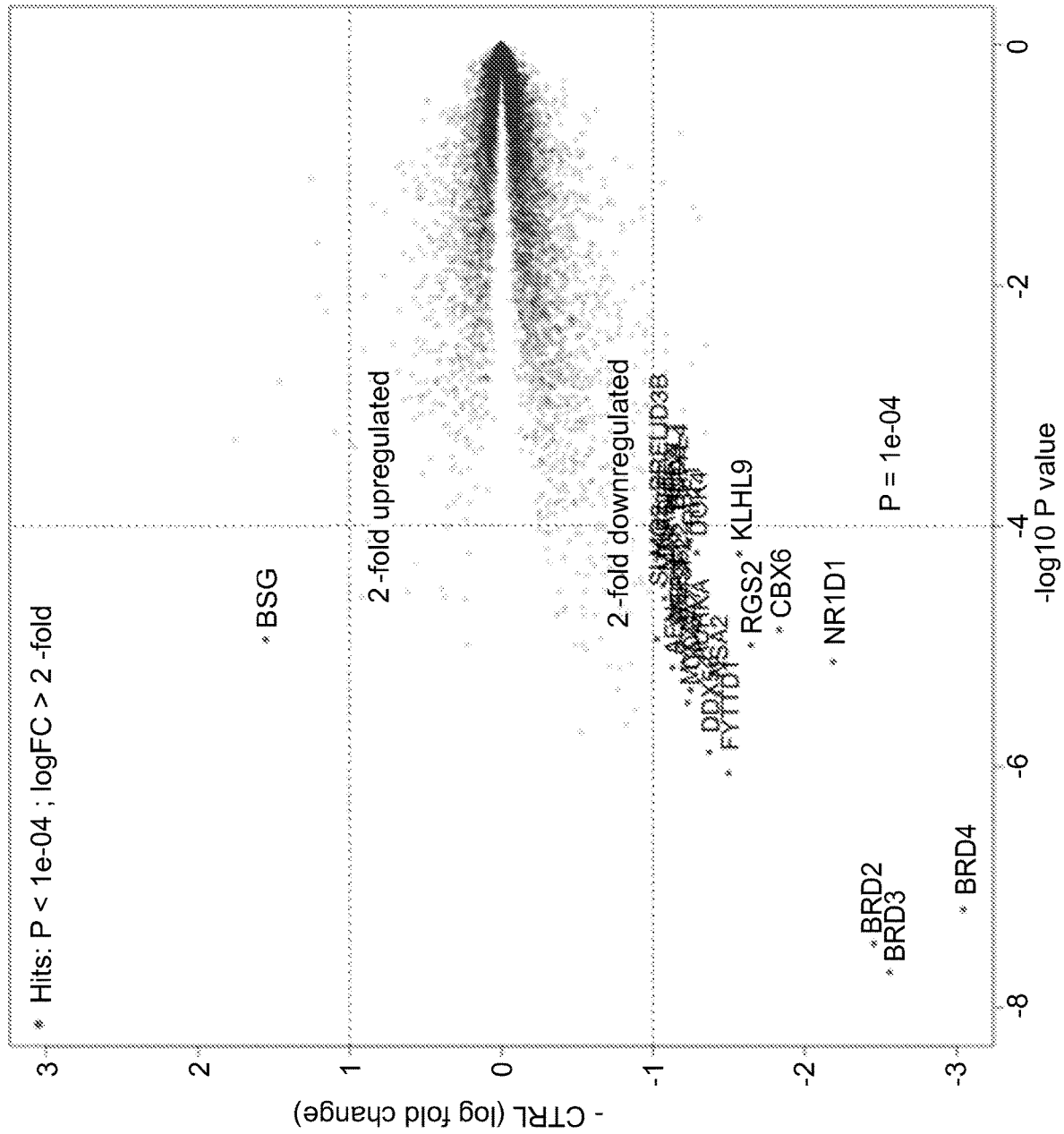

The results are illustrated in FIG. 4A-FIG. 4B. FIG. 4A demonstrates compound 1-mediated downregulation of bromodomain proteins BRD4. These results confirm that heterobifunctional compound 1 was capable of inducing selective degradation of endogenous BRD4 protein in cells. The tricyclic ring structure of the cereblon binder did not induce degradation of common IMiD-dependent off-targets.

FIG. 4B demonstrates compound 2-mediated downregulation of bromodomain proteins BRD2, 3 and 4. These results confirm that heterobifunctional compound 2 was capable of inducing degradation of endogenous bromodomain family of proteins in cells. The tricyclic ring structure of the cereblon binder did not induce degradation of common IMiD-dependent off-targets.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

What is claimed is:

1. A compound having a structure represented by formula (I):

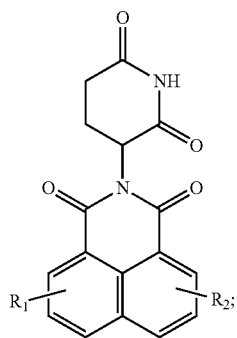

wherein $R_1$ and $R_2$ independently represent H, halo, hydroxyl, optionally substituted C1-C5 alkyl, optionally substituted C1-C5 alkoxy, or optionally substituted amine, optionally substituted amide, acyl, or

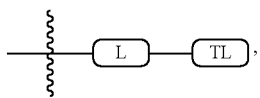

provided that one of $R_1$ and $R_2$ represents

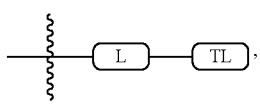

wherein the targeting ligand (TL) has a structure represented by:

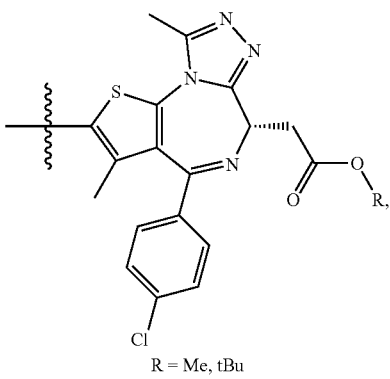

R = Me, tBu

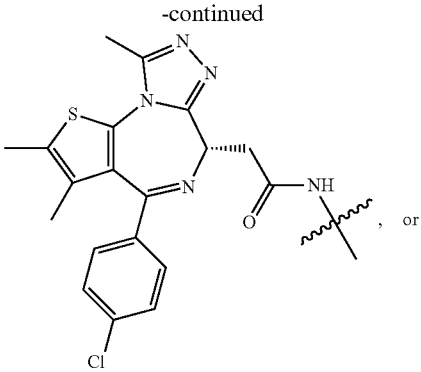

, or

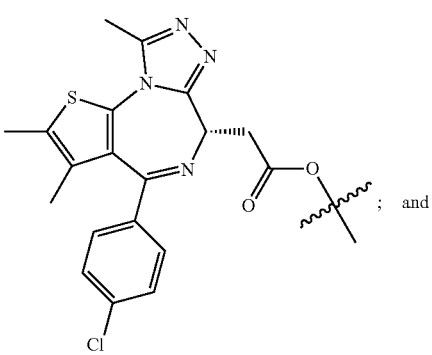

; and the linker (L) comprises an alkylene chain or a polyethylene glycol chain, either of which may be interrupted by, and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different, or a pharmaceutically acceptable salt or stereoisomer thereof.

2. The compound of claim 1, wherein $R_1$ represents

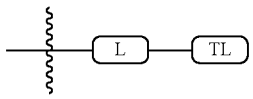

and $R_2$ represents H, halo, hydroxyl, optionally substituted C1-C5 alkyl, optionally substituted C1-C5 alkoxy, optionally substituted amine, optionally substituted amide, or acyl.

3. The compound of claim 2, wherein $R_2$ represents H.

4. The compound of claim 1, wherein $R_2$ represents

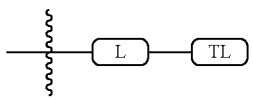

and $R_1$ represents H, halo, hydroxyl, optionally substituted C1-C5 alkyl, optionally substituted C1-C5 alkoxy, optionally substituted amine, optionally substituted amide, or acyl.

5. The compound of claim 4, wherein $R_2$ represents H.

6. The compound of claim 1, wherein the targeting ligand (TL) has a structure represented by:

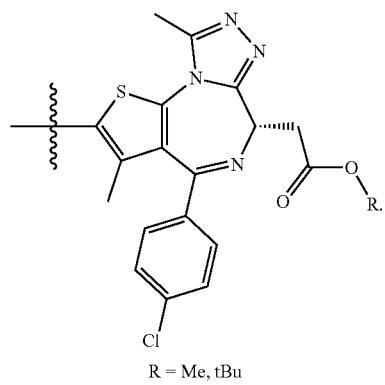

R = Me, tBu

7. The compound of claim 6, wherein the targeting ligand binds bromodomain-containing-protein 2, 3, 4 and bromodomain testis-specific protein.

8. The compound of claim 1, wherein the linker has a structure represented by any one of:

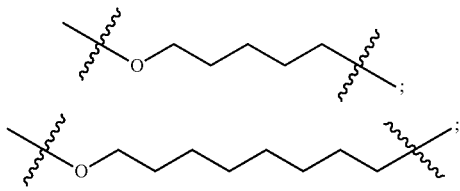

-continued

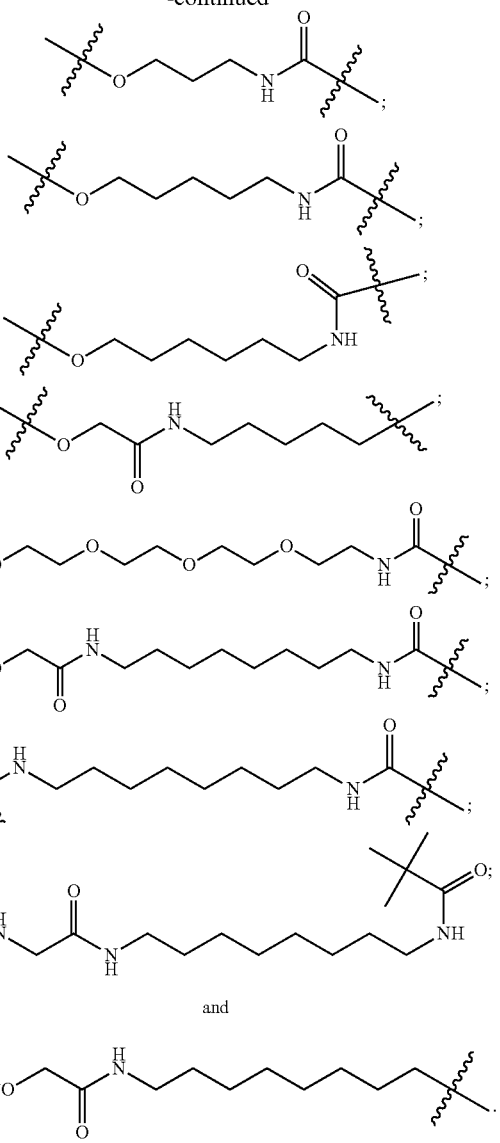

9. The compound of claim 1, which has a structure as follows:

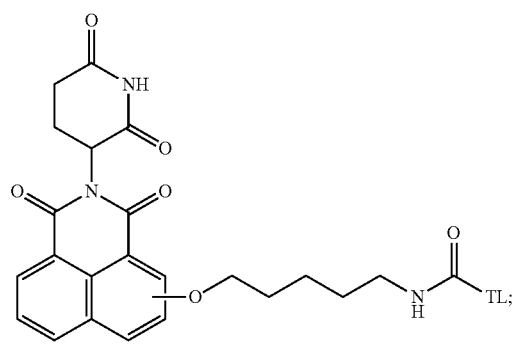

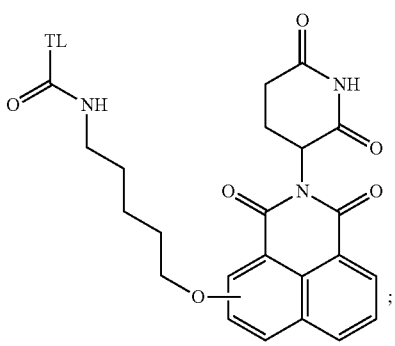

91
92
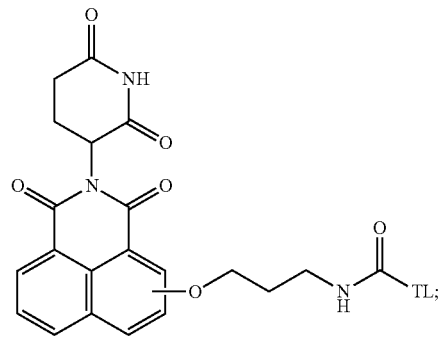
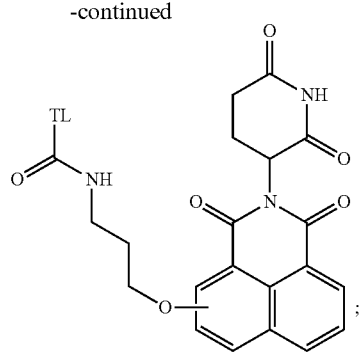
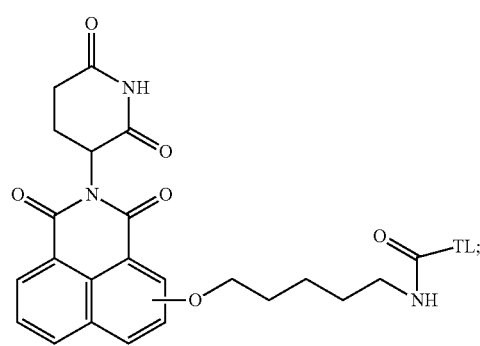
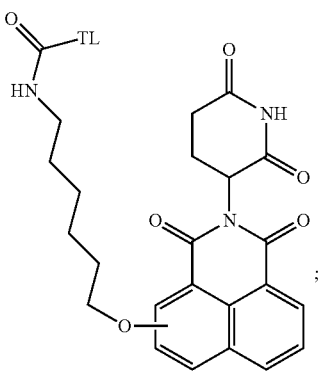
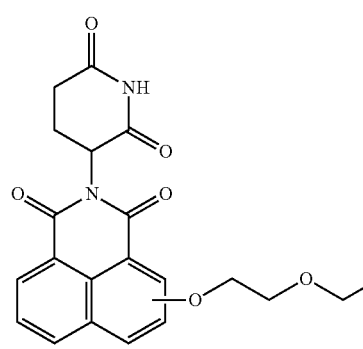
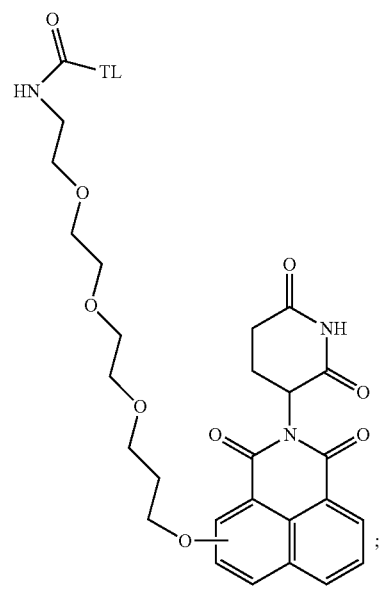

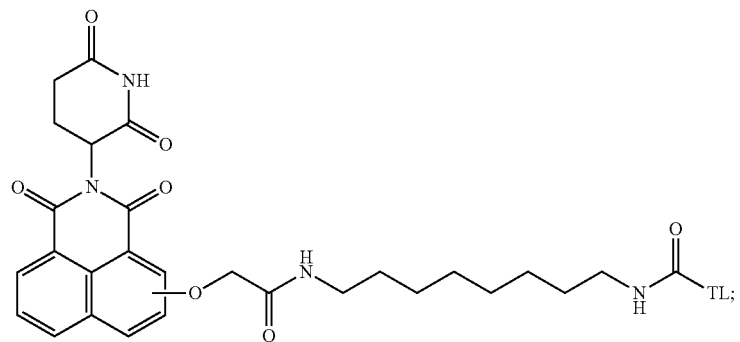
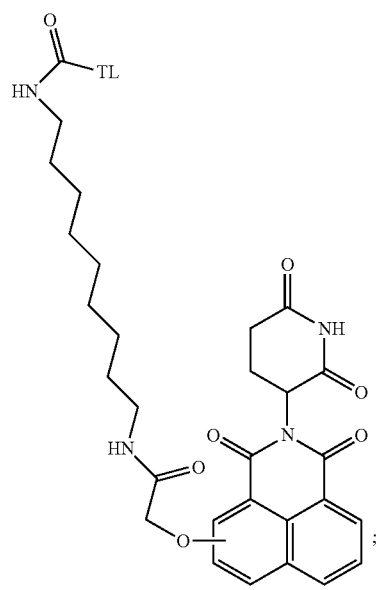
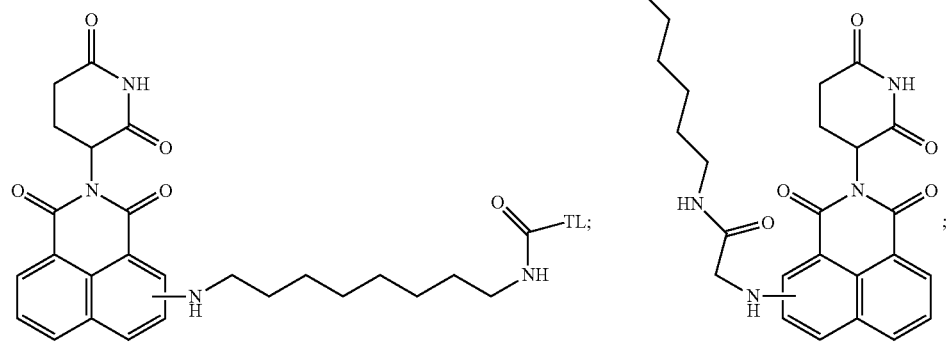
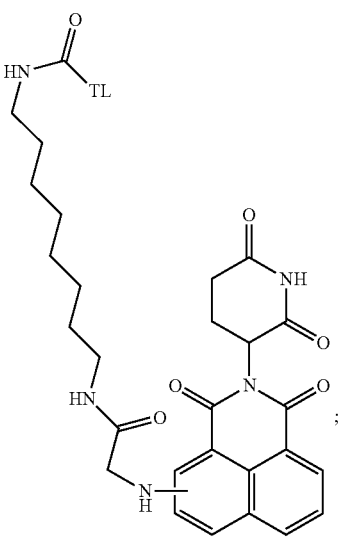
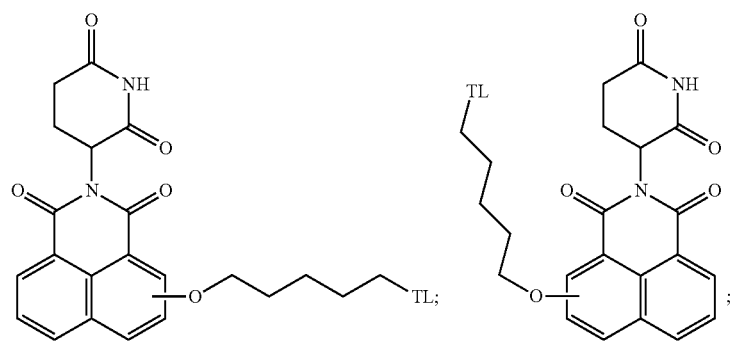

-continued
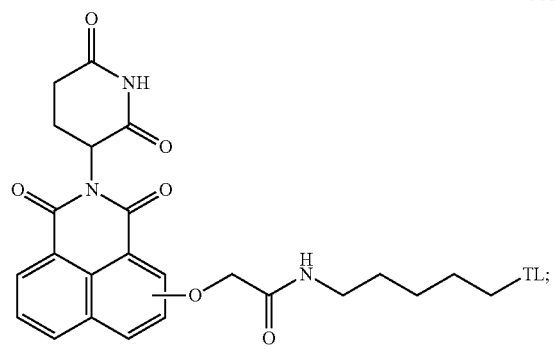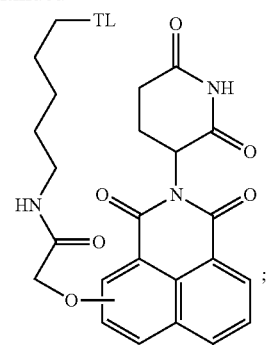
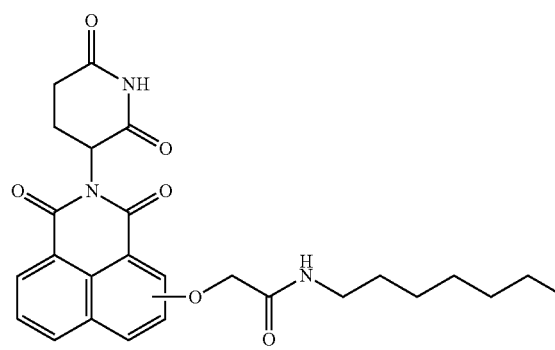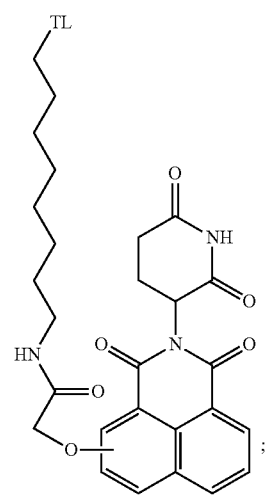
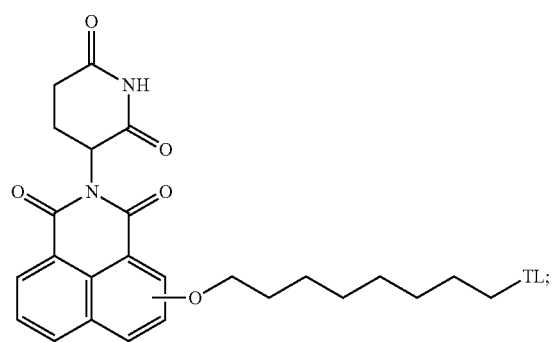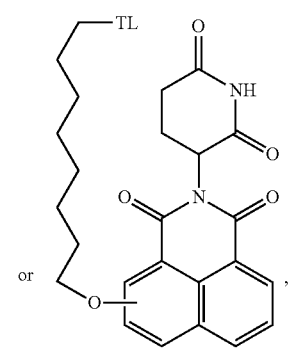

or a pharmaceutically acceptable salt or stereoisomer thereof.
10. The compound of claim 1, which has a structure as follows:
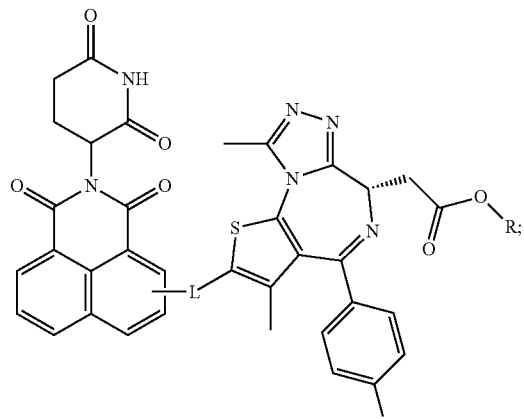
R = Me, tBu
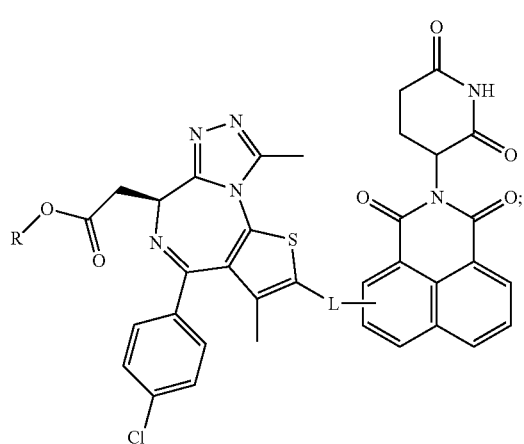
R = Me, tBu
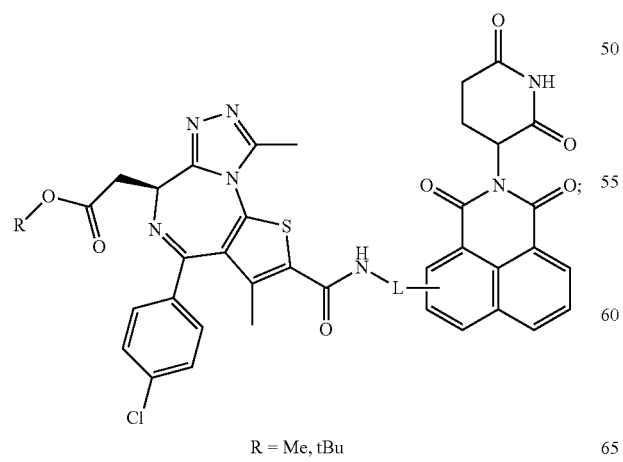
R = Me, tBu
-continued
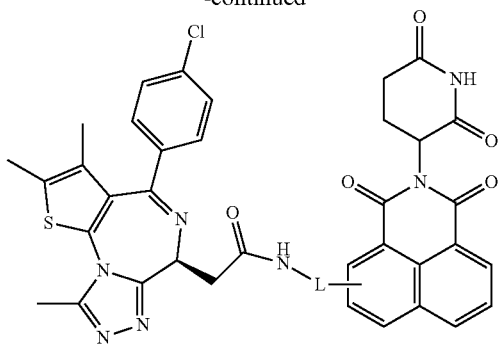
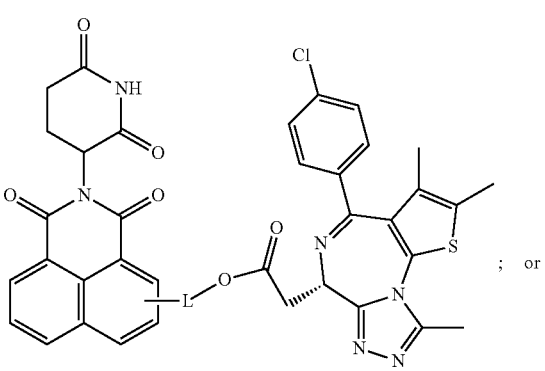
; or
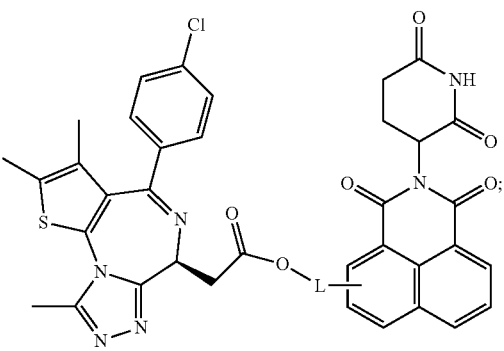
or a pharmaceutically acceptable salt or stereoisomer thereof.

11. The compound of claim 1, which is:
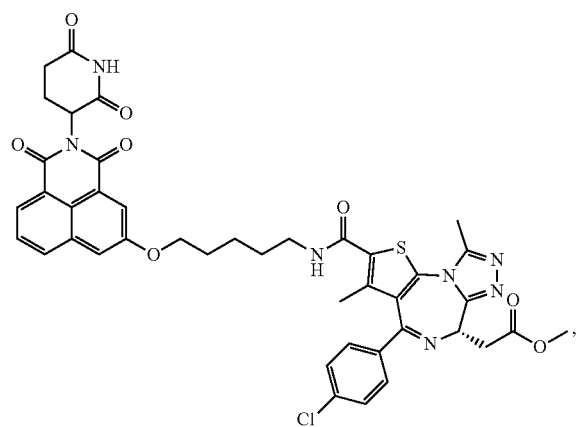
(1)
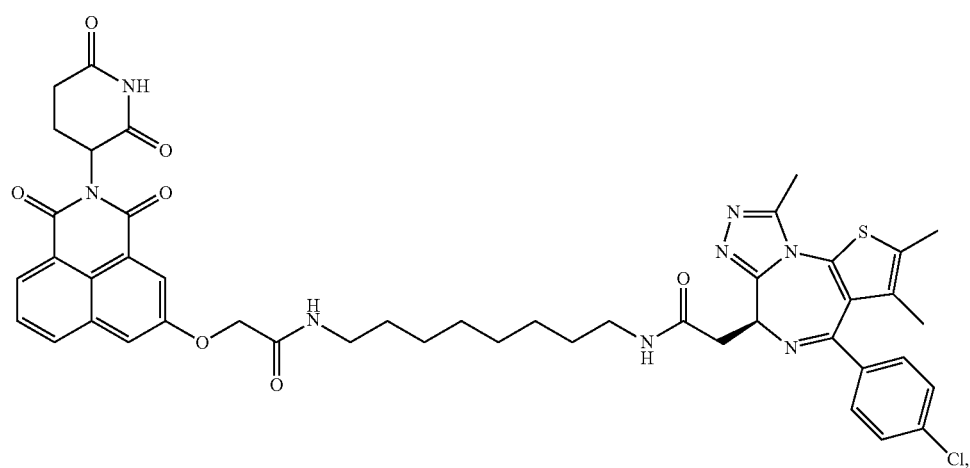
(2)
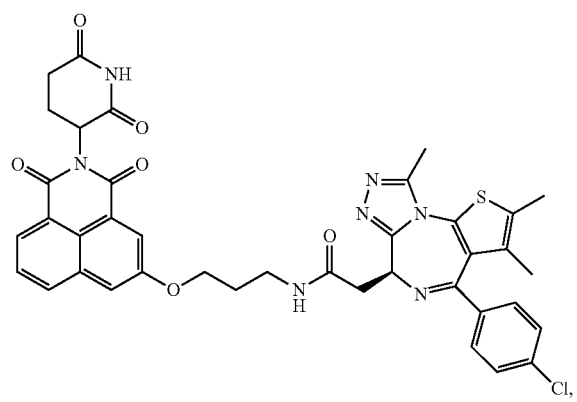
(3)
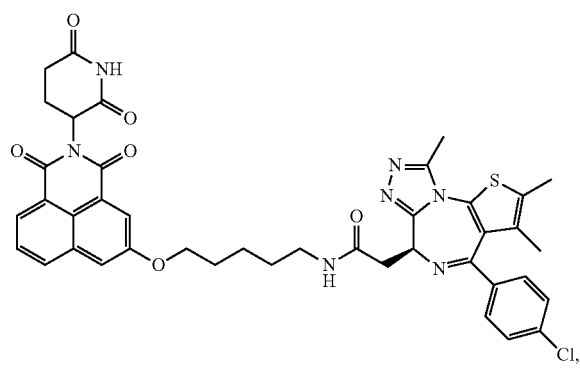
(4)

(5)
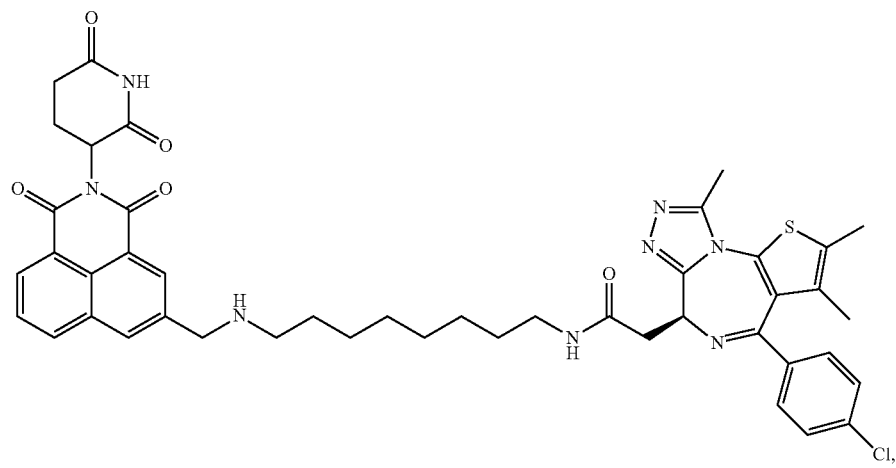
(6)
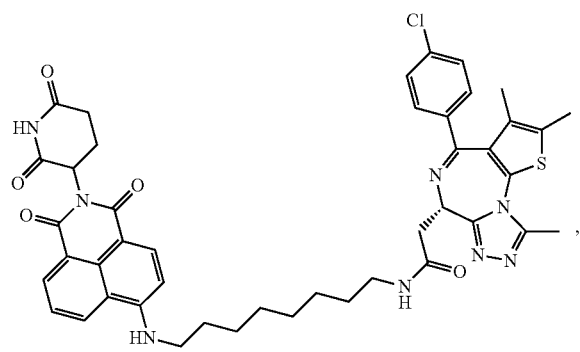
(7)
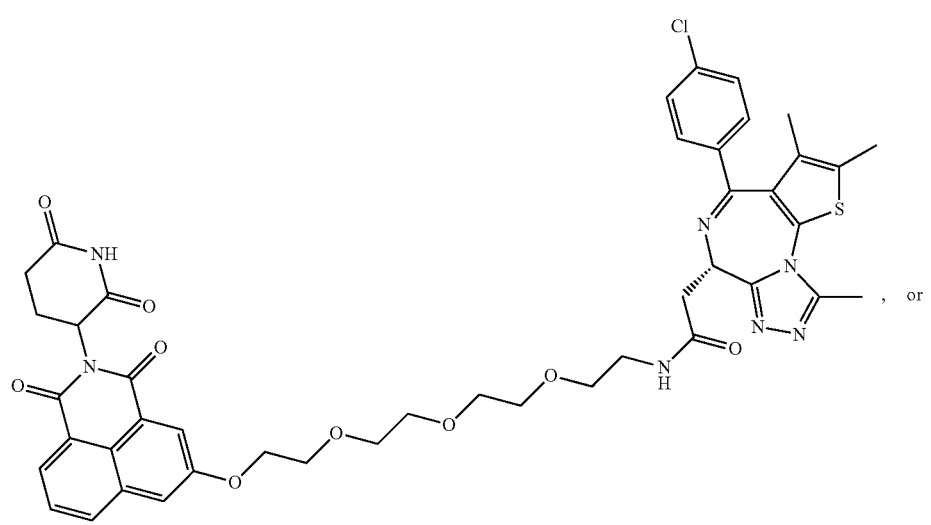

-continued

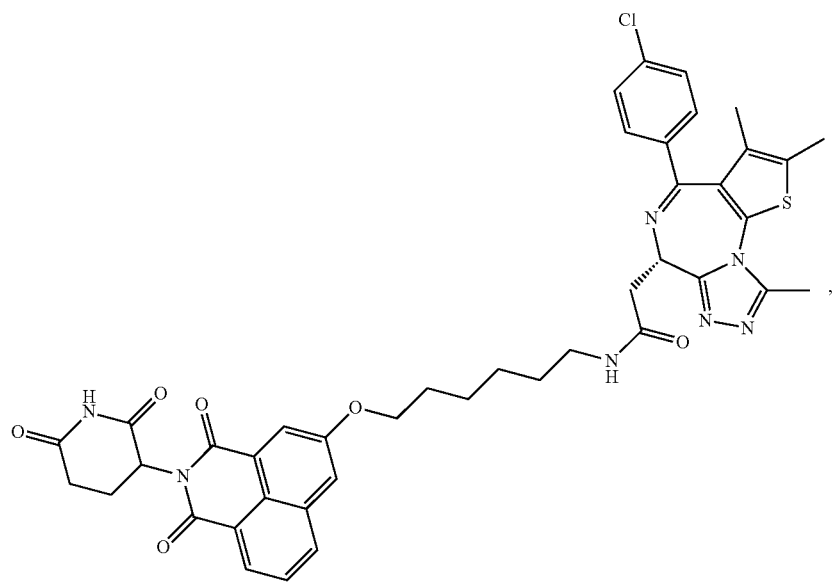

(8)

or a pharmaceutically acceptable salt or stereoisomer thereof.

12. A pharmaceutical composition, comprising a therapeutically effective amount of the compound of claim 1 or pharmaceutically acceptable salt or stereoisomer thereof, and a pharmaceutically acceptable carrier.

13. The pharmaceutical composition of claim 12, which is in the form of a capsule.

14. A method of treating cancer, wherein the cancer is leukemia or multiple myeloma, comprising administering to a subject in need thereof a therapeutically effective amount of the compound of claim 1 or pharmaceutically acceptable salt or stereoisomer thereof.

15. The method of claim 14, wherein the cancer is multiple myeloma.

16. The compound of claim 1, which is:

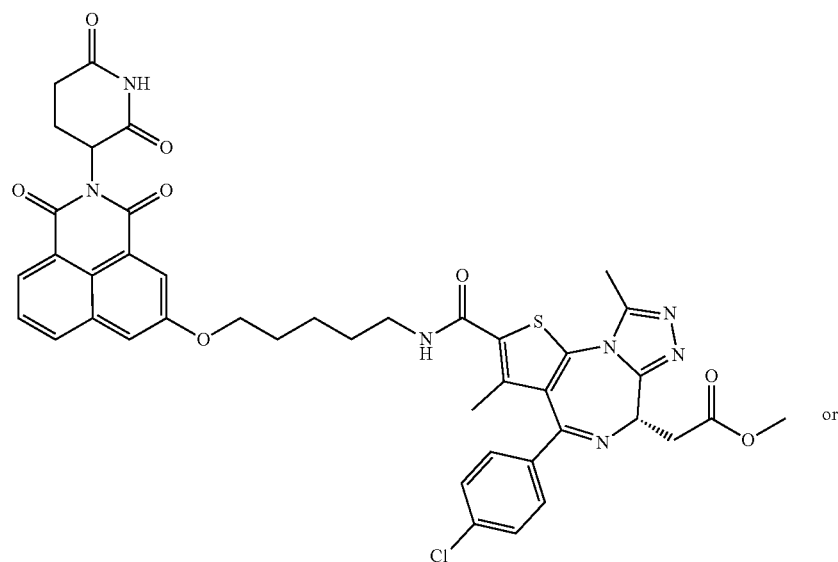

(1)

or

-continued

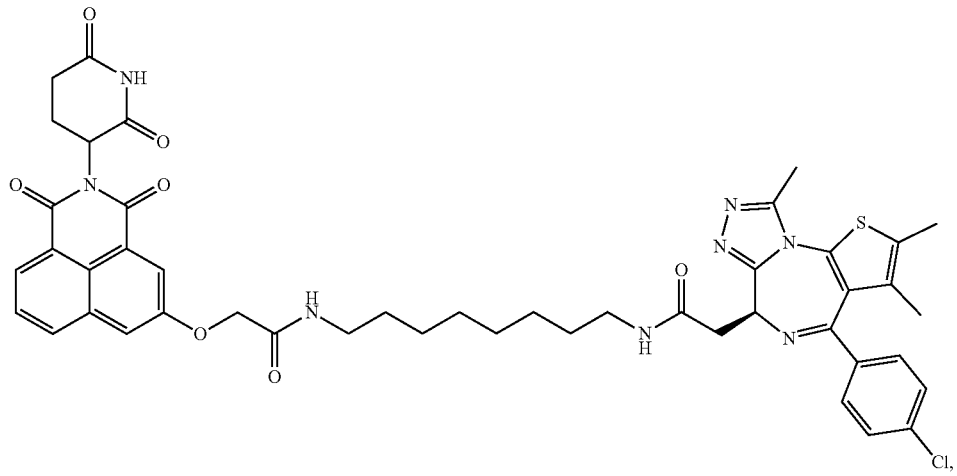

or a pharmaceutically acceptable salt or stereoisomer thereof.

17. A pharmaceutical composition, comprising a therapeutically effective amount of the compound of claim 16 or pharmaceutically acceptable salt or stereoisomer thereof, and a pharmaceutically acceptable carrier.

18. The compound of claim 1, wherein the targeting ligand (TL) has a structure represented by:

19. The compound of claim 1, wherein the targeting ligand (TL) has a structure represented by:

(2)

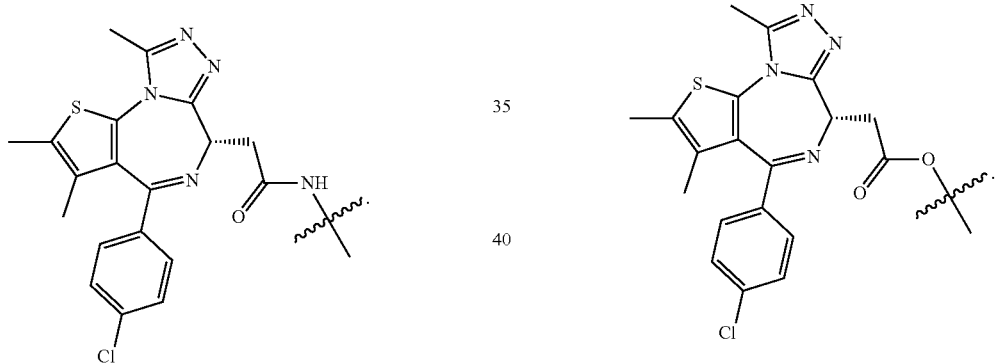

* * * * *